US008338101B2

(12) United States Patent
Van Baelen et al.

(10) Patent No.: US 8,338,101 B2
(45) Date of Patent: Dec. 25, 2012

(54) METHOD FOR DESIGNING A DRUG REGIME FOR HIV-INFECTED PATIENTS

(75) Inventors: Kurt Van Baelen, Westerlo (BE); Lieven Jozef Stuyver, Herzele (BE); Kevin Karel Florentina Ariën, Nazareth (BE)

(73) Assignee: VIRCO BVBA, Mechelen (BE)

(*) Notice: Subject to any disclaimer, the term of this patent is extended or adjusted under 35 U.S.C. 154(b) by 395 days.

(21) Appl. No.: 12/524,120

(22) PCT Filed: Jan. 23, 2008

(86) PCT No.: PCT/EP2008/050778
§ 371 (c)(1), (2), (4) Date: Jul. 22, 2009

(87) PCT Pub. No.: WO2008/090185
PCT Pub. Date: Jul. 31, 2008

(65) Prior Publication Data

US 2010/0099078 A1 Apr. 22, 2010

(30) Foreign Application Priority Data

Jan. 23, 2007 (EP) .................................... 07101037
Feb. 15, 2007 (EP) .................................... 07102423

(51) Int. Cl.
*C12Q 1/00* (2006.01)
*C12Q 1/70* (2006.01)
*C12Q 1/68* (2006.01)

(52) U.S. Cl. ................ 435/6.13; 435/4; 435/5; 435/6.1; 435/6.12

(58) Field of Classification Search ........................ None
See application file for complete search history.

(56) References Cited

U.S. PATENT DOCUMENTS

| | | | | |
|---|---|---|---|---|
| 5,674,680 | A | 10/1997 | Saksela et al. | |
| 6,800,463 | B1 | 10/2004 | Larder et al. | |
| 2003/0124514 | A1* | 7/2003 | Vingerhoets et al. ............. | 435/5 |

FOREIGN PATENT DOCUMENTS

| | | |
|---|---|---|
| WO | WO 9727319 A1 * | 7/1997 |
| WO | WO 01/79540 | 10/2001 |
| WO | WO 01/81624 | 11/2001 |
| WO | WO 02/23186 | 3/2002 |
| WO | WO 02/33402 | 4/2002 |
| WO | WO 2007/118849 | 10/2007 |
| WO | WO 2008/090185 | 7/2008 |

OTHER PUBLICATIONS

Maguire et al. Changes in Human Immunodeficiency Virus Type 1 Gag at Positions L449 and P453 are Linked to I50V Protease Mutants In Vivo and Cause Reduction of Sensitivity to Amprenavir and Improved Viral Fitness in Vitro. Journal of Virology 2002, vol. 76(15), pp. 7398-7406.*
Ratner et al. Complete nucleotide sequence of the AIDS virus, HTLV-III. Nature 1985, vol. 313, p. 277-284.*
Buck et al. Design strategies and performance of custom DNA sequencing primers. BioTechniques 1999, vol. 27, pp. 528-536.*
Fikkert, Valery et al. "Development of Resistance Against Diketo Derivatives of Human Immunodeficiency Virus Type 1 by Progressive Accumulation of Integrase Mutations". Journal of Virology, vol. 77, No. 21, Nov. 2003, pp. 11459-11470, XP002462285.
Hertogs, et al. "A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs". Antimicrobial Agents and Chemotherapy, American Society for Microbiology, Washington, D.C. vol. 42, No. 2, Feb. 1998, pp. 269-276, XP002137814.
Petropoulos, C.J. et al. "A Novel Phenotypic Drug Susceptibility Assay for Human Immunodeficiency Virus Type 1". Antimicrobial Agents and Chemotherapy, American Society for Microbiology, Washington, D.C., vol. 44, No. 4, Apr. 2000, pp. 920-928, XP002962272.
Lee, Deborah, J. et. al. "Human Immunodeficiency virus Type 1 (HIV-1) Integrase: Resistance to Diketo Acid Integrase Inhibitors Impairs HIV-1 Replication and Integratin and Confers Cross-Resistance to L-Chicoric Acid". Journal of Virology, vol. 78, No. 11, Jun. 2004, pp. 5835-5847, XP002462286.
Shafer, R.W. et al. "Human Immunodeficiency Virus Reverse Transcriptase and Protease Sequence Database". Nucleic Acids Research, Oxford University Press, Surrey, GB, vol. 27, No. 1, Jan. 1, 1999, pp. 348-352, XP002202303.
Boom et al., "Rapid and simple method for purification of nucleic acids", J. Clin. Microbiol., Mar. 1990, 28(3), 495-503.
GenBank Accession No. K03455, "Human immunodeficiency virus type 1 (HXB2), complete gnome", Oct. 21, 2002, 8 pages.
Kellam et al., "Recombinant virus assay: a rapid, phenotypic assay for assessment of drug susceptibility of human immunodeficiency virus type 1 isolates", Antimicrob. Agents Chemother., 1994, 38(1), 23-30.
Pauwels et al., "Rapid and automated tetrazolium-based colorimetric assay for the detection of anti-HIV compounds", J. Virol. Methods, 1988, 20, 309-321.

* cited by examiner

*Primary Examiner* — Louise Humphrey
(74) *Attorney, Agent, or Firm* — Woodcock Washburn LLP

(57) ABSTRACT

The instant disclosure describes a novel genotype and phenotype assay to elucidate and/or evaluate new potential HIV integrase inhibitors, but also currently approved and experimental compounds that target protease, reverse transcriptase, and RNaseH. This assay allows studying linked mutations and mutational patterns that occur under HAART and experimental therapies.

1 Claim, 25 Drawing Sheets

*Vector : Delta[Gag-Pol]*
*FIG. 1A. Digest pUC18 with PstI and EcoRI*
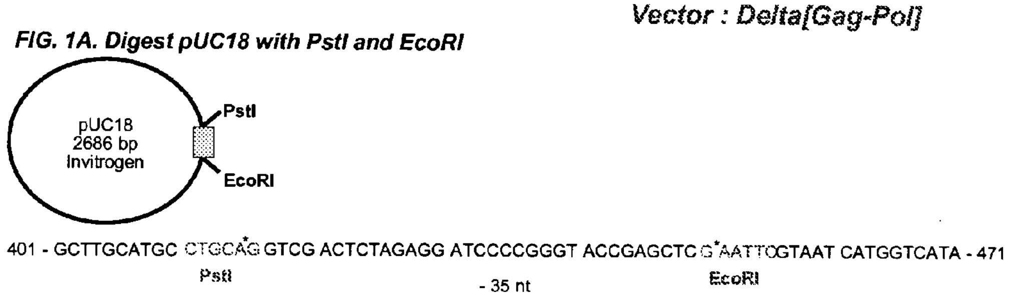
*FIG 1B. Ligate linker into pUC18*
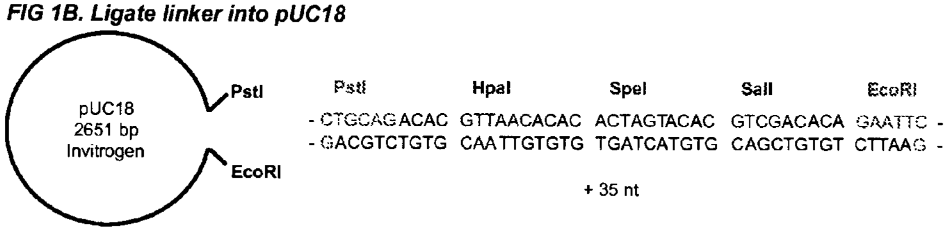
*FIG. 1C. Digest pUC18-LINK with HpaI and SalI*
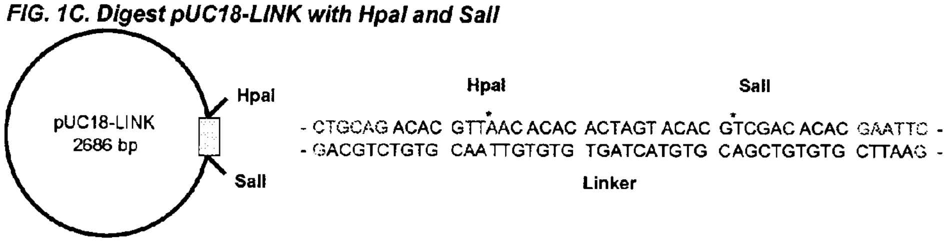
*FIG. 1D. Ligate fragment A into pUC18-LINK*
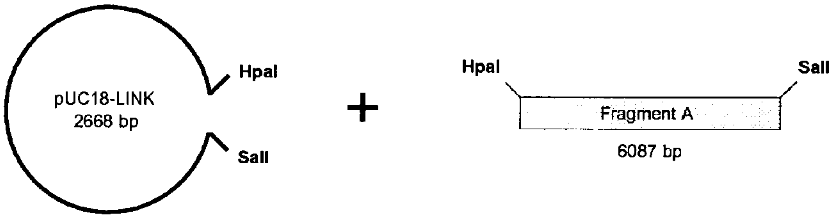

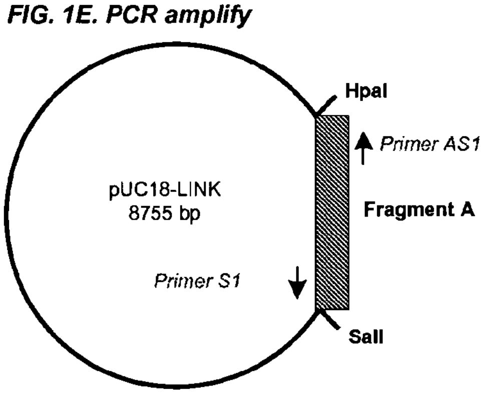
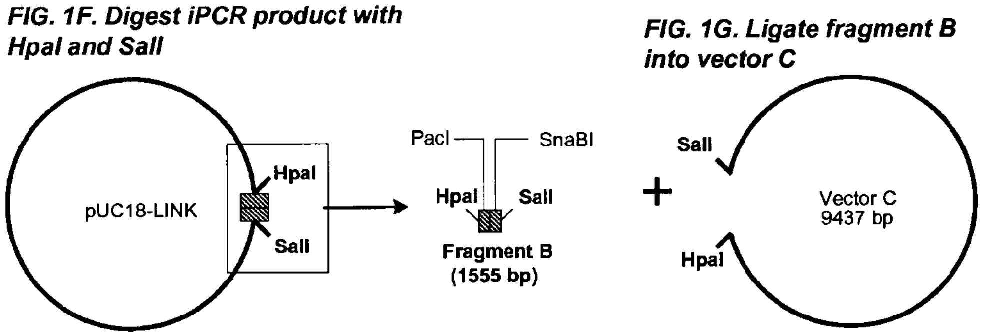
Figure 1: Creation of delta[GAG-POL] backbone based on the HXB2D_eGFP HIV-1 vector.

Detail of steps 1E, 1F, and 1G
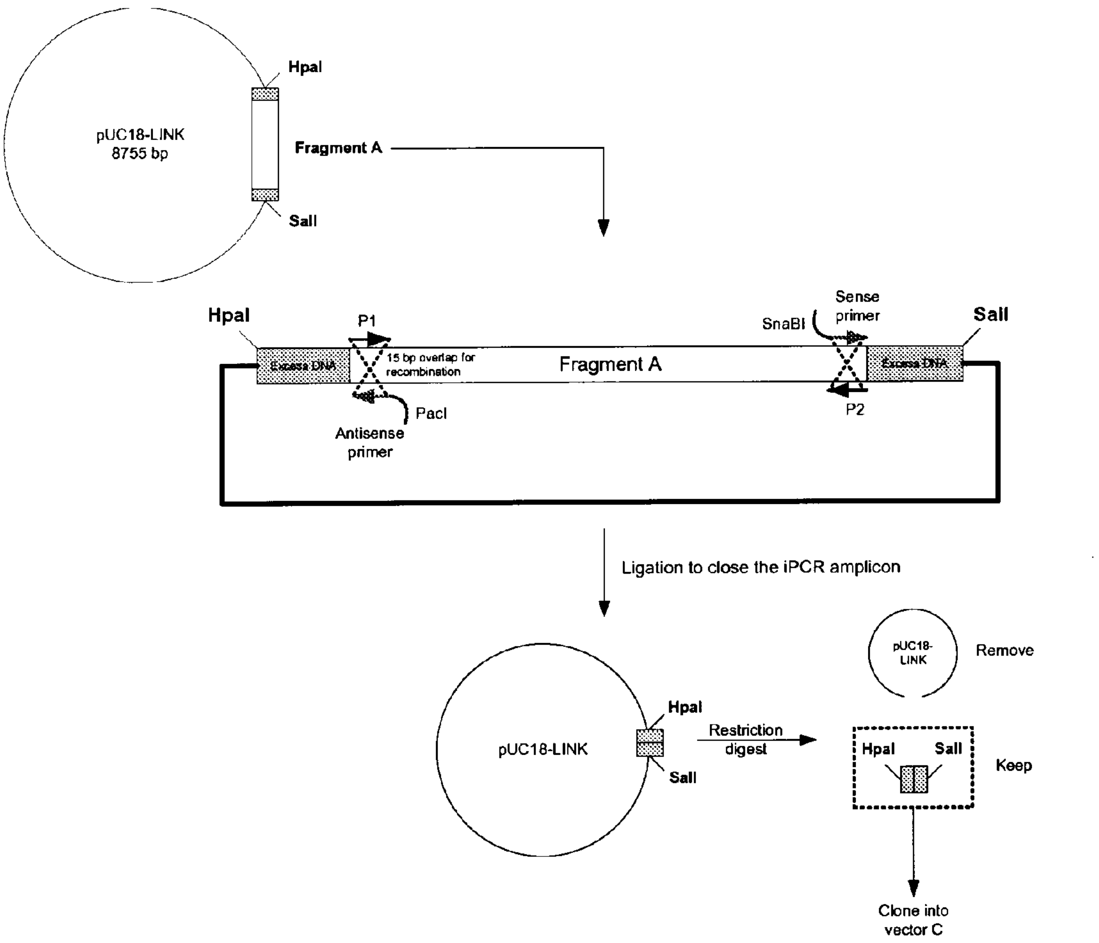
Figure 2: Detailed description of the 'inverse PCR' reaction.

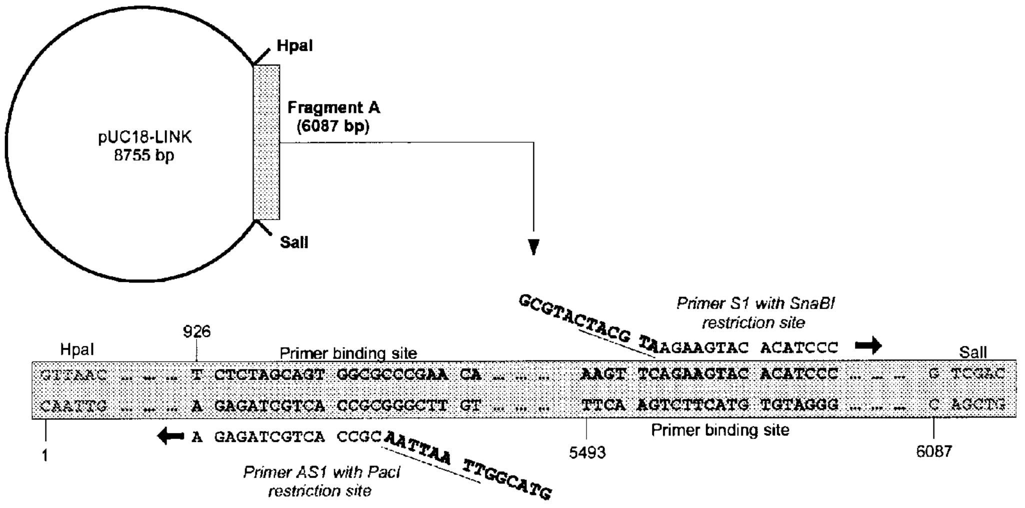
Figure 3 : Primers for 'inverse PCR' containing the PacI and SnaBI restriction sites.

Vector : Delta[RT-INT]
FIG. 4A. Digest pUC18 with PstI and EcoRI
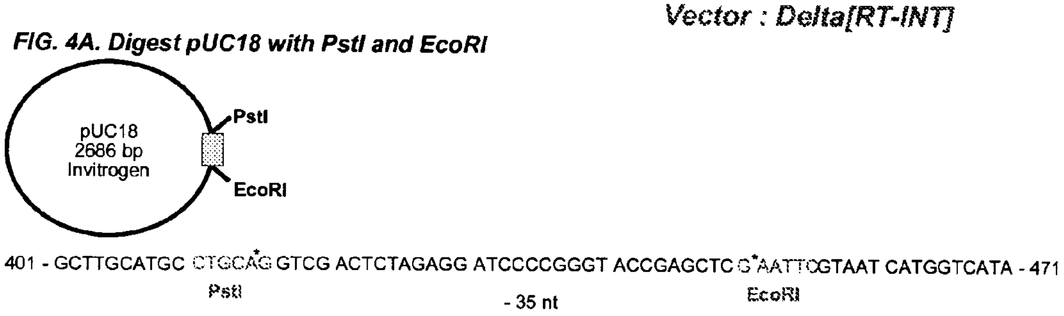
FIG 4B. Ligate linker into pUC18
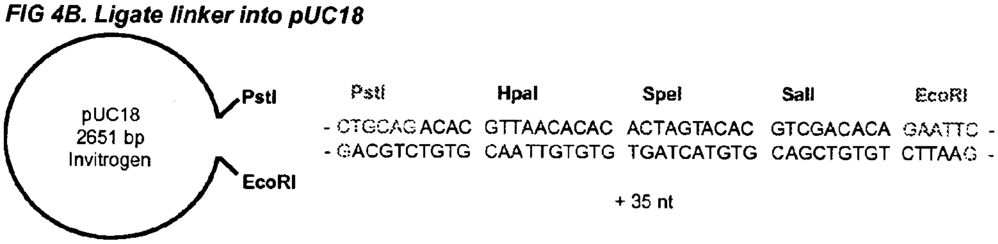
FIG. 4C. Digest pUC18-LINK with SpeI and SalI
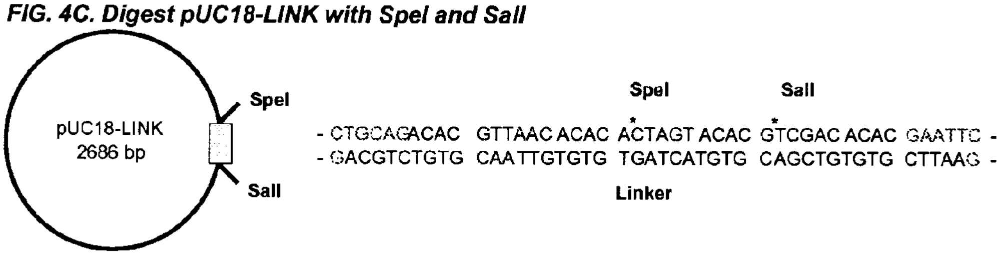
FIG. 4D. Ligate fragment X into pUC18-LINK
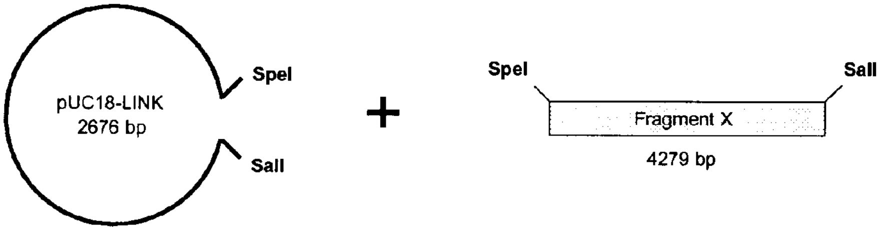

*FIG. 4E. PCR amplify*
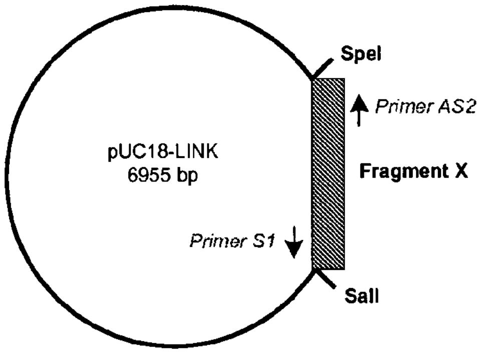
*FIG. 4F. Digest iPCR product with SpeI and SalI*
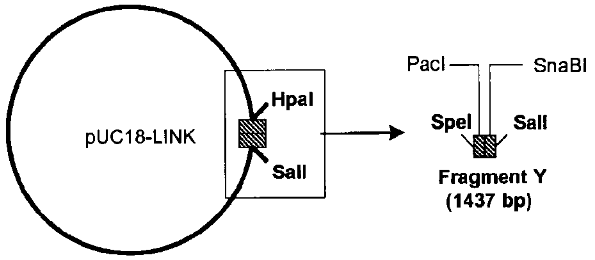
*FIG. 4G. Ligate fragment Y into vector Z*
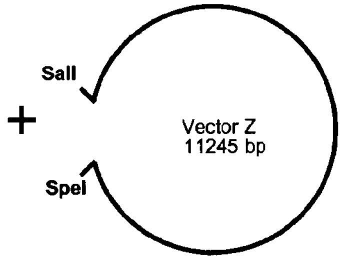
Figure 4: Creation of delta[RT-INT] backbone based on the HXB2D_eGFP HIV-1 vector.

Detail of steps 4E, 4F, and 4G
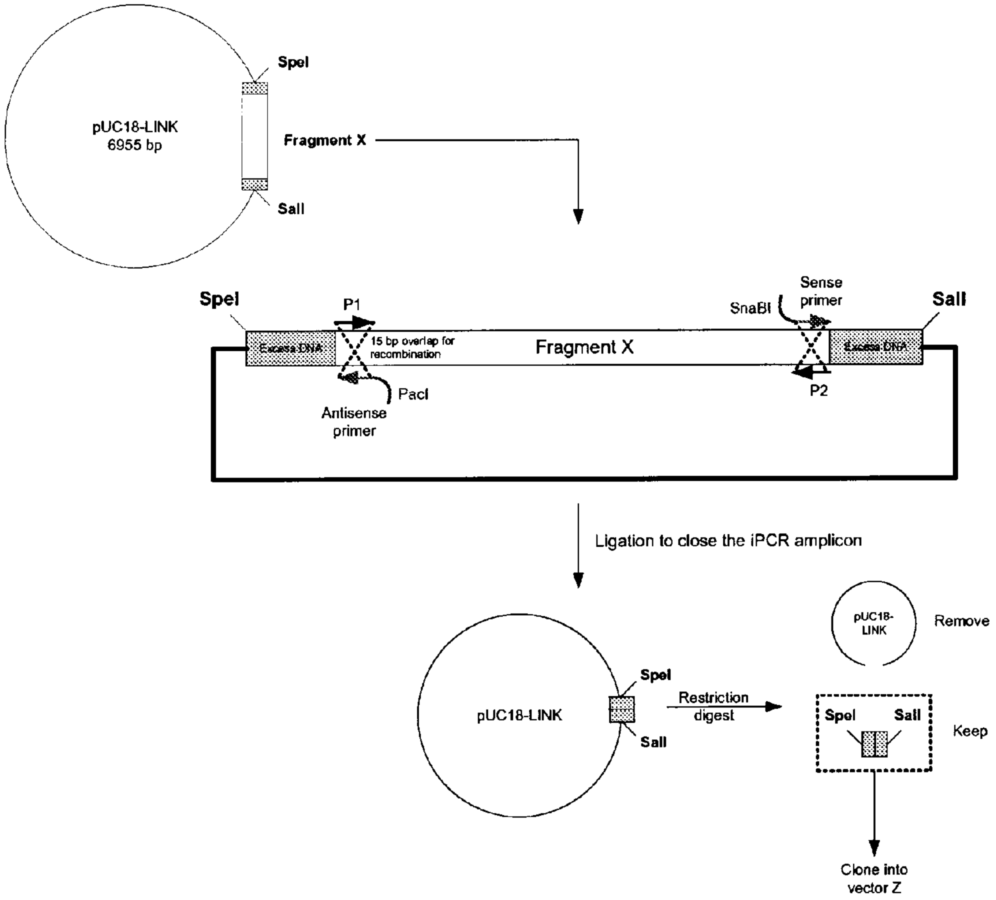
Figure 5: Dctailed description of the 'inverse PCR' reaction.

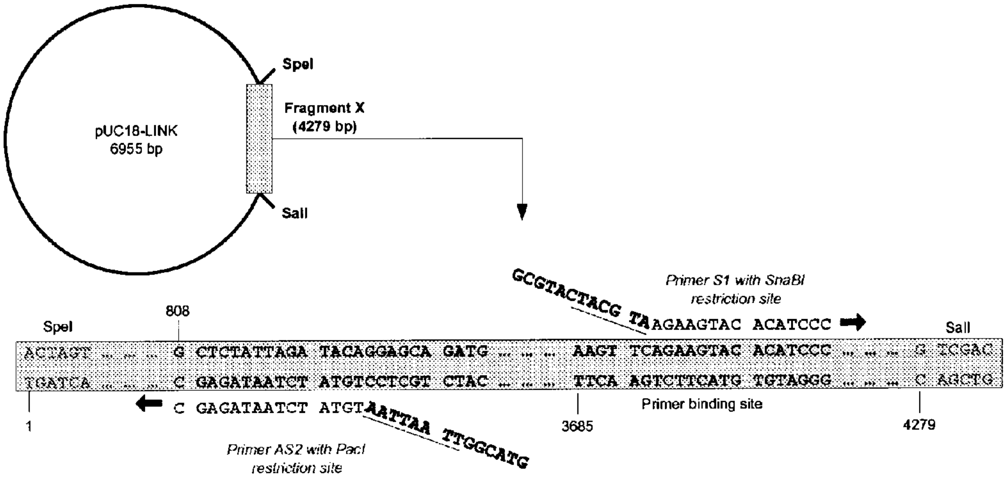
Figure 6: Primers for 'inverse PCR' containing the PacI and SnaBI restriction sites

*Vector : Delta[Gag-Pr]*
*FIG. 7A. Digest pUC18 with PstI and EcoRI*
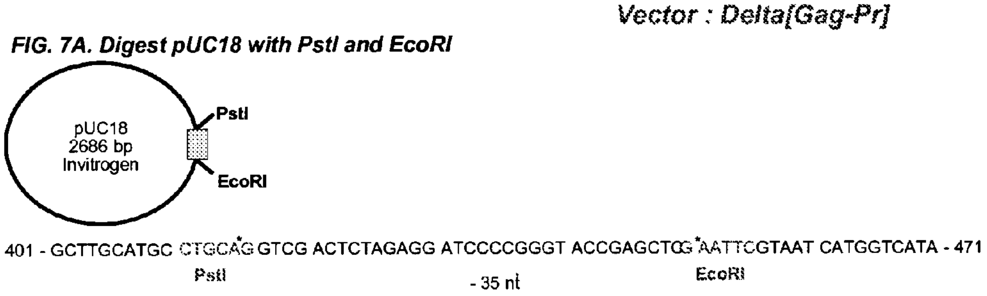
*FIG 7B. Ligate linker into pUC18*
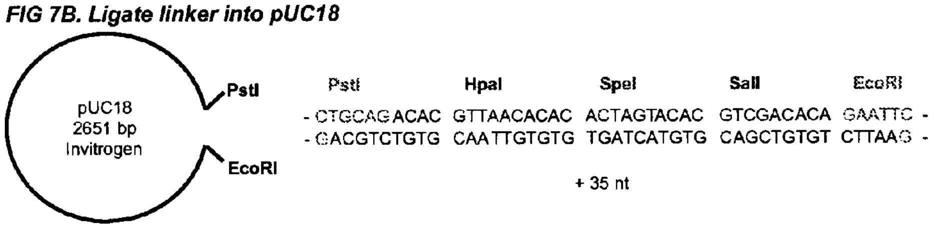
*FIG. 7C. Digest pUC18-LINK with HpaI and SalI*
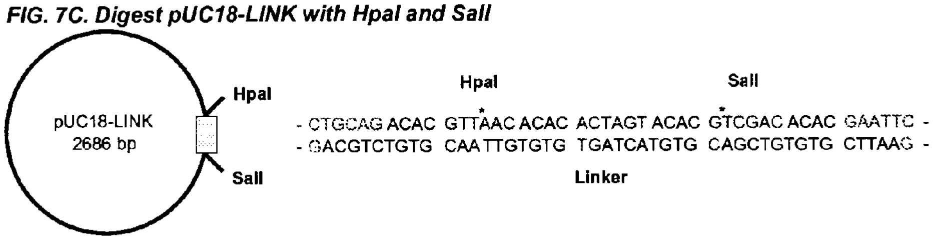
*FIG. 7D. Ligate fragment A into pUC18-LINK*
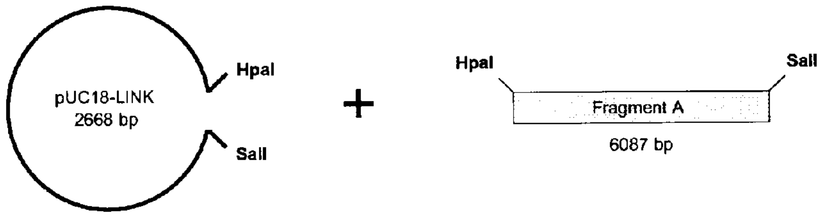

*FIG. 7E. PCR amplify*
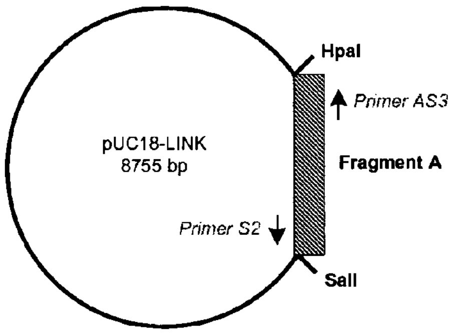
*FIG. 7F. Digest iPCR product with HpaI and SalI*
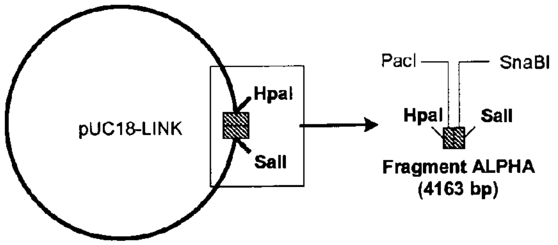
*FIG. 7G. Ligate fragment ALPHA into vector C*
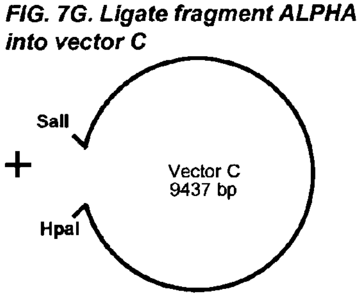
Figure 7: Creation of delta[GAG-PR] backbone based on the HXB2D_eGFP HIV-1 vector.

Detail of steps 7E, 7F, and 7G
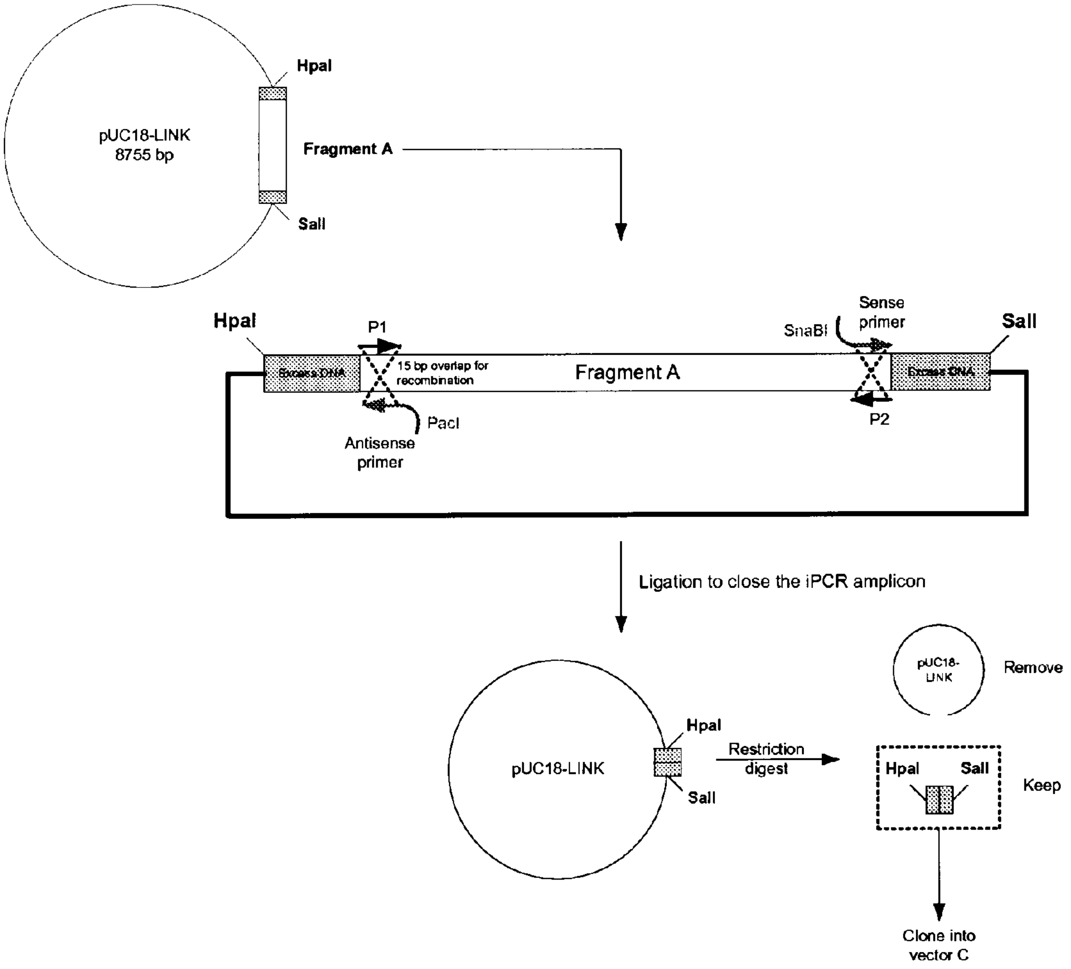
Figure 8: Detailed description of the 'inverse PCR' reaction.

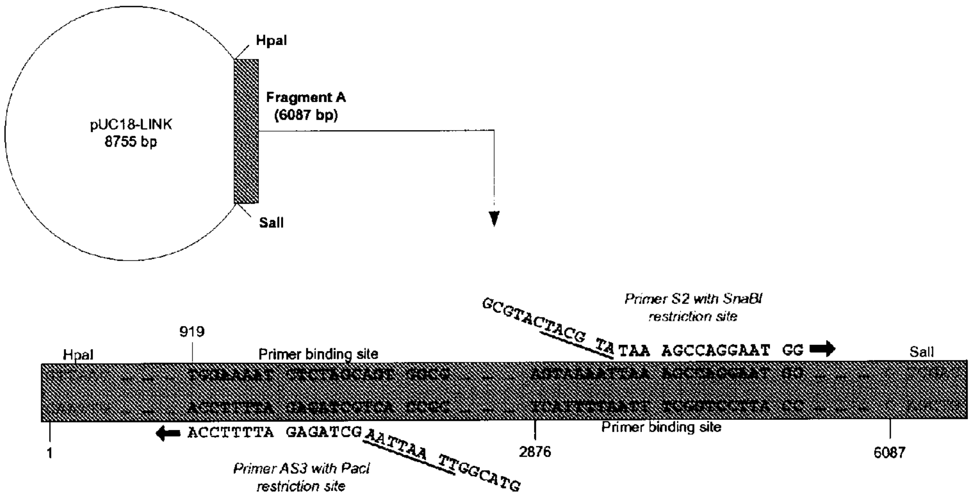
Figure 9 : Primers for 'inverse PCR' containing the PacI and SnaBI restriction sites

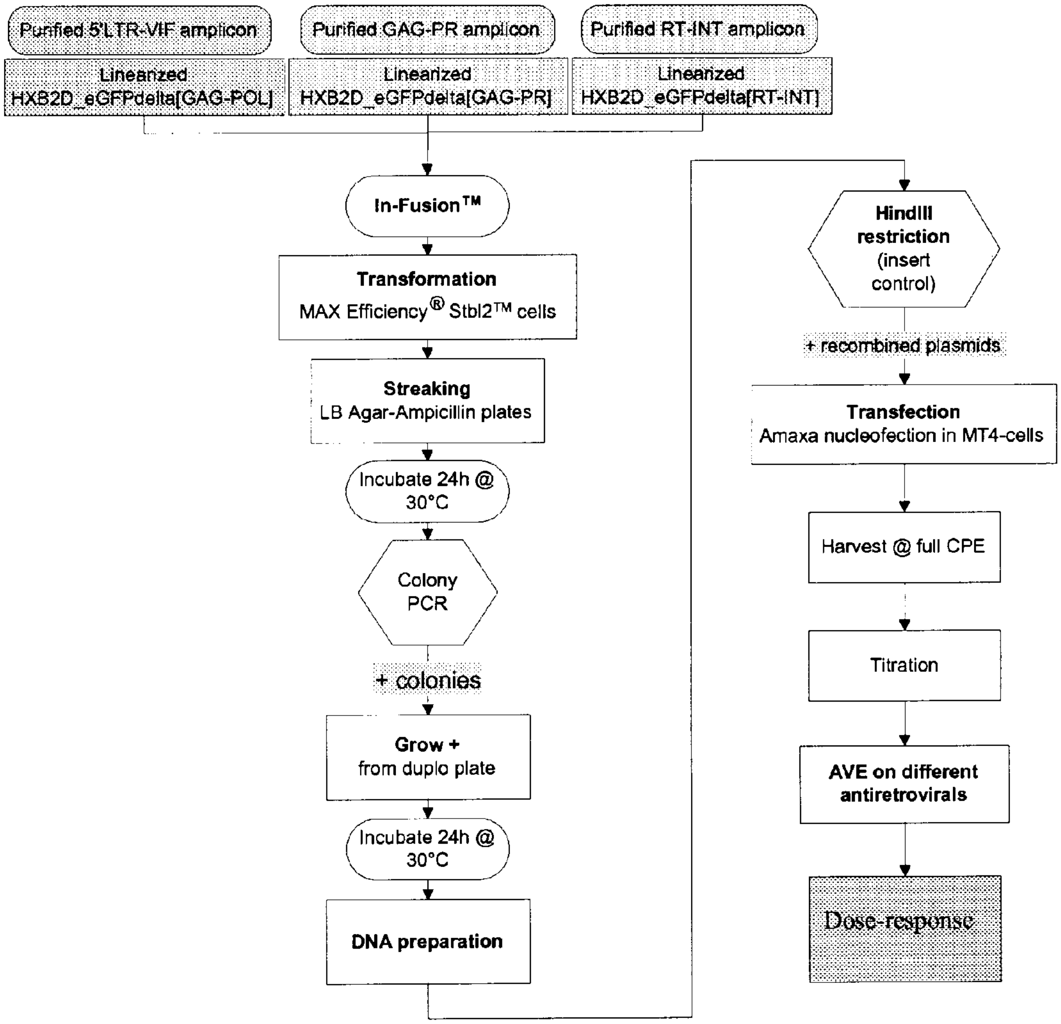
Figure 10: Phenotypic process flow

Figure 11: Dose-response curves for 1 GAG-POL recombinant virus stock.

Tenofovir

Efavirenz

Atazanavir

Saquinavir

PA457

Indinavir

Ritonavir

Nevirapine

Nelfinavir

Lamivudine

Tipranavir

Abacavir

Lopinavir

GS9137

Zidovudine

Amprenavir

Merck L870,810

Merck L731,988

Vector : Delta[Pol]
*FIG. 12A. Digest pUC18 with PstI and EcoRI*
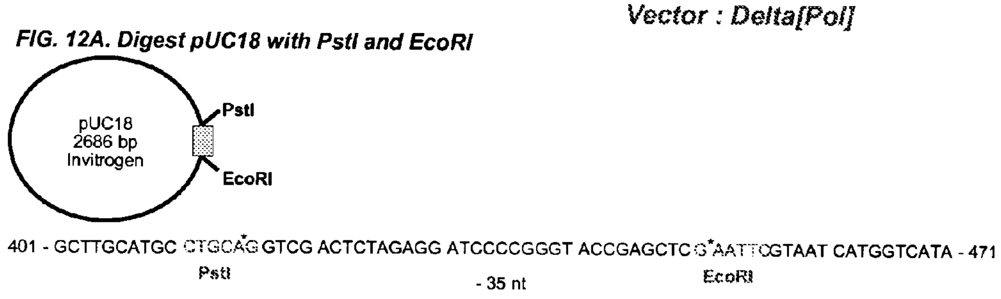
*FIG 12B. Ligate linker into pUC18*
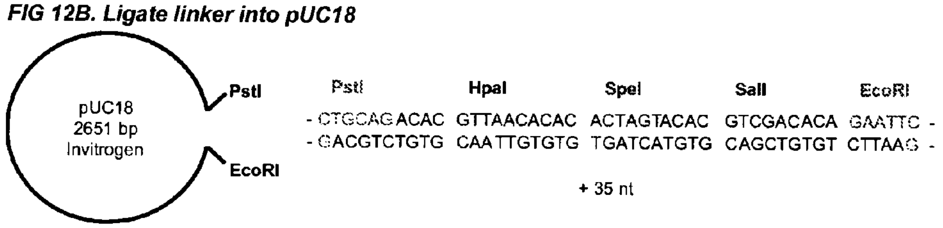
*FIG. 12C. Digest pUC18-LINK with HpaI and SalI*
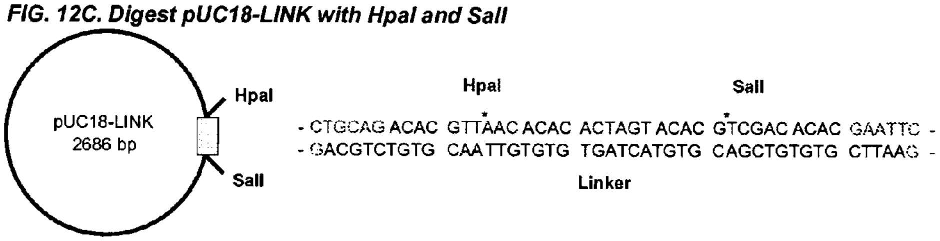
*FIG. 12D. Ligate fragment A into pUC18-LINK*
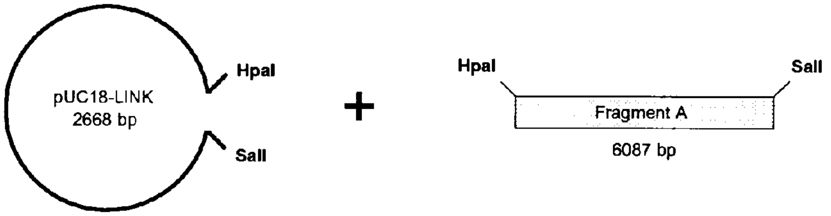

*FIG. 12E. PCR amplify*
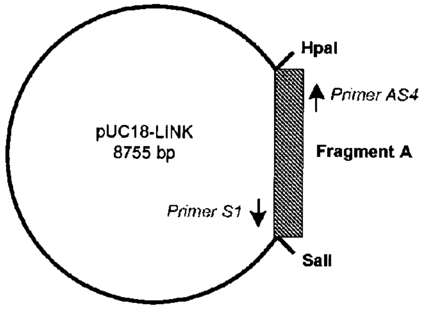
*FIG. 12F. Digest iPCR product with HpaI and SalI*
*FIG. 12G. Ligate fragment ALPHA into vector C*
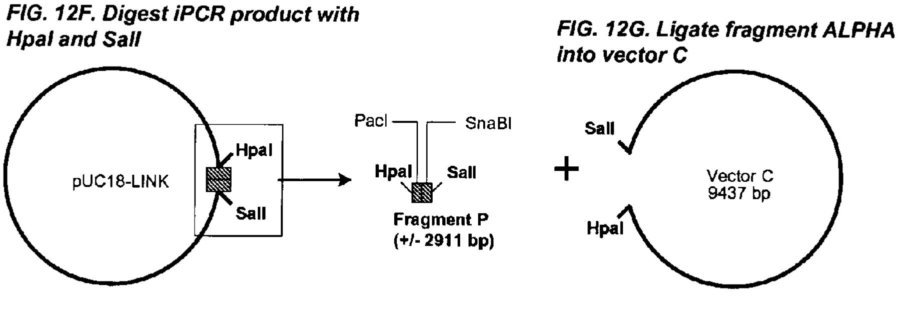
Figure 12: Creation of delta[POL] backbone based on the HXB2D_eGFP HIV-1 vector.

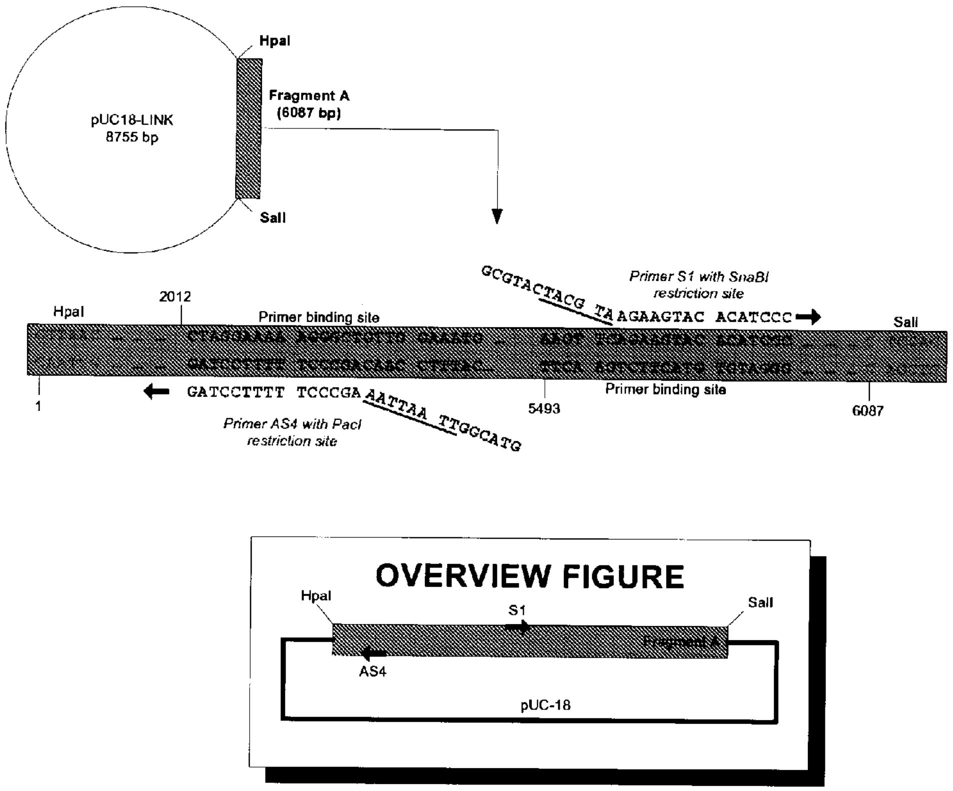
Figure 13. Primers for 'inverse PCR' containing the PacI and SnaBI restriction sites.

METHOD FOR DESIGNING A DRUG REGIME FOR HIV-INFECTED PATIENTS

CROSS REFERENCE TO RELATED APPLICATIONS

This application is the national stage of PCT Application No. PCT/EP2008/050778 filed Jan. 23, 2008, which claims priority from European Patent Application No. 07102423.6, filed Feb. 15, 2007, and European Patent Application No. 07101037.5, filed 23 Jan. 2007, the entire disclosures of which are hereby incorporated in their entirety.

Millions and millions of people have been infected with the human immunodeficiency virus ("HIV"), the causative agent of acquired immune deficiency syndrome ("AIDS"), since the early 1980s. HIV/AIDS is now the leading cause of death in sub-Saharan Africa, and is the fourth biggest killer worldwide. At the end of 2001, an estimated 40 million people were living with HIV globally.

Currently, five classes of antiretroviral drugs are used to treat infection by Human Immunodeficiency Virus (HIV), i.e. protease inhibitors (PIs), two classes of reverse transcriptase inhibitors (nucleoside reverse transcriptase inhibitors abbreviated as N-RTI and non-nucleoside reverse transcriptase inhibitors abbreviated as NN-RTI), entry inhibitors (fusion inhibitors (FIs) and co-receptor antagonists), and intergrase inhibitors (INIs). Integrase inhibitors are a promising new class of antiretrovirals interfering with HIV replication by blocking the ability of the virus to integrate into the genetic material of human cells.

Modern anti-HIV drugs target different stages of the HIV life cycle and a variety of enzymes essential for HIV's replication and/or survival. Amongst the drugs that have so far been approved for AIDS therapy are nucleoside reverse transcriptase inhibitors ("NRTIs") such as AZT, ddl, ddC, d4T, 3TC, and abacavir; nucleotide reverse transcriptase inhibitors such as tenofovir; non-nucleoside reverse transcriptase inhibitors ("NNRTIs") such as nevirapine, efavirenz, and delavirdine; protease inhibitors ("PIs") such as darunavir, saquinavir, ritonavir, indinavir, nelfinavir, amprenavir, lopinavir and atazanavir; fusion inhibitors, such as enfuvirtide, co-receptor antagonists such as maraviroc and integrase inhibitors such as raltegravir.

Nonetheless, in the vast majority of subjects none of the antiviral drugs currently approved, either alone or in combination, proves effective either to prevent eventual progression of chronic HIV infection to AIDS or to treat acute AIDS. This phenomenon is due, in part, to the high mutation rate of HIV and the rapid emergence of mutant HIV that are resistant to antiviral therapeutics upon administration of such drugs to infected individuals.

The integrase protein thus represents an interesting target for HIV inhibitor research. HIV integrase is required for integration of the viral genome into the genome of the host cell, a step in the replicative cycle of the virus. HIV integrase is a protein of about 32 KDa encoded by the pol gene, and is produced in vivo by protease cleavage of the gag-pol precursor protein during the production of viral particles. The integration process takes place following reverse transcription of the viral RNA. First, the viral integrase binds to the viral DNA and removes two nucleotides from the 3' end of the viral long-terminal repeat (LTR) sequences on each strand. This step is called 3' end processing and occurs in the cytoplasm within a nucleoprotein complex termed the pre-integration complex (PIC). Second, in a process called strand transfer, the two strands of the cellular DNA into which the viral DNA will be inserted, the target DNA, is cleaved in a staggered fashion.

The 3' ends of the viral DNA are ligated to the 5' ends of the cleaved target DNA. Finally, host enzymes probably repair remaining gaps.

With the increasing number of available anti-HIV compounds as mentioned above, the number of potential treatment protocols for HIV infected patients will continue to increase. Many of the currently available compounds are administered as part of a combination therapy. The high complexity of treatment options coupled with the ability of the virus to develop resistance to HIV inhibitors requires the frequent assessment of treatment strategies. The ability to accurately monitor the replicative capacity of virus in patients with a drug regimen and to use that data to modify the doses or combinations of inhibitors allows physicians to effectively reduce the formation of drug resistant virus and provide an optimal, tailored treatment for each patient. Accordingly, as new drugs targeting new HIV polypeptides become available, phenotypic and genotypic assays for determining resistance or susceptibility of HIV infecting a patient to such new anti-HIV drugs are highly needed.

While phenotyping and genotyping assays have been developed and marketed for reverse transcriptase and protease genes, protocols and assays for evaluation of drug resistance against the integrase gene have not been successfully developed.

For instance, the amplicon used in the marketed Antivirogram® contains the gag cleavage sites (p1/p7 and p1/p6), PR (codon 1-99) and RT (codon 1-400) coding sequences respectively, leaving the rest of the relevant HIV reverse transcriptase gene and more importantly the HIV integrase gene undetected.

The instant disclosure describes a novel genotype and phenotype assay to elucidate and/or evaluate new HIV integrase inhibitors, but also currently approved and experimental compounds that target maturation, protease, reverse transcriptase, and RNaseH. This assay allows studying linked mutations and mutational patterns that occur under HAART and experimental therapies. The selection of the primers used for the preparation of the appropriate amplicon is, due to the mutations and mutational patterns present in the HIV sequence, of the utmost importance to further develop a reliable and sensitive genotype and phenotype assay.

BRIEF DESCRIPTION OF THE DRAWINGS

FIG. 1 shows a schematic representation for creating the GAG-POL vector backbone based on the HXB2D_eGFP HIV-1 vector. Subparts A-D, F and G illustrate certain digestion/ligation vector manipulations, while subpart E depicts PCR amplification of Fragment A.

FIG. 2 provides a more detailed schematic representation of the inverse PCR described for creating the GAG-POL vector backbone based on the HXB2D_eGFP HIV-1 vector.

FIG. 3 depicts the primer binding sites for the inverse PCR described for creating the GAG-POL vector backbone based on the HXB2D_eGFP HIV-1 vector.

FIG. 4 shows a schematic representation for creating the RT-INT vector backbone based on the HXB2D_eGFP HIV-1 vector. Subparts A-D, F and G illustrate certain digestion/ligation vector manipulations, while subpart E depicts PCR amplification of Fragment X.

FIG. 5 provides a more detailed schematic representation of the inverse PCR described for creating the RT-INT vector backbone based on the HXB2D_eGFP HIV-1 vector.

FIG. 6 depicts the primer binding sites for the inverse PCR described for creating the RT-INT vector backbone based on the HXB2D_eGFP HIV-1 vector.

FIG. 7 shows a schematic representation for creating the GAG-PR vector backbone based on the HXB2D_eGFP HIV-1 vector. Subparts A-D, F and G illustrate certain digestion/ligation vector manipulations, while subpart E depicts PCR amplification of Fragment A.

FIG. 8 provides a more detailed schematic representation of the inverse PCR described for creating the GAG-PR vector backbone based on the HXB2D_eGFP HIV-1 vector.

FIG. 9 depicts the primer binding sites for the inverse PCR described for creating the GAG-PR vector backbone based on the HXB2D_eGFP HIV-1 vector.

FIG. 10 is a flow chart summarizing an experimental process for determining the phenotype of viruses produced using a GAG-POL, GAG-PR or RT-INT vector.

FIG. 12 shows a schematic representation for creating the delta[POL] vector backbone based on the HXB2D_eGFP HIV-1 vector. Subparts A-D, F and G illustrate certain digestion/ligation vector manipulations, while subpart E depicts PCR amplification of Fragment A.

FIG. 13 depicts the primer binding sites for the inverse PCR described for creating the delta[POL] vector backbone based on the HXB2D_eGFP HIV-1 vector.

Figure 11A:
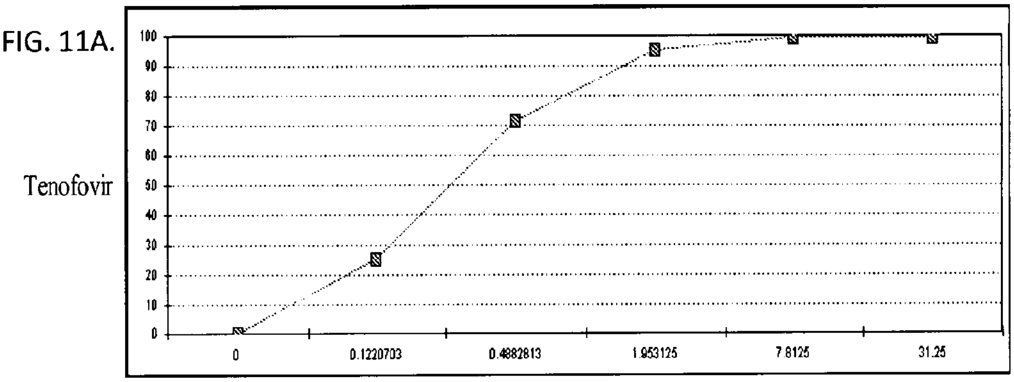
FIG. 11(A-R) shows the dose-response curves for one GAG-POL recombinant virus stock for all drugs tested.

In contrast to the amplicon mentioned above as used in the Antivirogram, the amplicon described in the instant invention and referred to as 5' LTR-Vif fragment contains the complete gag and complete pol (PR-RT-INT) coding region (4588 bp in HXB2D, GenBank accession number K03455). Gag is the Group-specific Antigen protein, encoding the structural capsid proteins. The proteins are produced as a GAG precursor polyprotein, which is processed by the viral protease. Other amplicons used in the current invention are the amplicon spanning the Gag cleavage sites p1/p7 and p1/p6, PR, RT, RNaseH and INT (3202 bp), referred to as Pol fragment, the amplicon containing the Gag and PR coding sequence (1980 bp), referred to as Gag-PR fragment, and the amplicon containing the complete RT, RNaseH and INT coding sequence (2898 bp), named RT-INT fragment.

The current disclosure describes an in vitro method for designing a drug regimen for an HIV-infected patient by determining the phenotypic susceptibility of HIV to at least one drug, comprising:

i) using at least one sample comprising HIV RNA from a patient, wherein the sample comprises the complete HIV gag-pol coding region;

ii) reverse-transcribing and amplifying the HIV RNA with primers specific for the complete HIV gag-pol coding region to obtain at least one amplicon comprising the complete HIV gag-pol coding region, wherein at least one primer is selected from SEQ ID NO: 1-4;

iii) generating a plasmid comprising a reference HIV sequence with a deletion of the complete HIV gag-pol coding region;

iv) preparing at least one recombinant virus by recombination or ligation between at least one amplicon obtained in step ii) and the plasmid comprising the reference HIV sequence with a deletion of the complete HIV gag-pol coding region obtained in step iii), and v) monitoring the at least one recombinant virus in the presence of the at least one drug to determine the phenotypic susceptibility of HIV to at least one drug, wherein said susceptibility is determined by the cytopathogenicity of said recombinant virus to cells or by determining the replicative capacity of said recombinant virus in the presence of at least one drug.

The instant disclosure describes an in vitro method for designing a drug regimen for an HIV-infected patient by determining the phenotypic susceptibility of HIV to at least one drug, comprising:

i) using at least one sample comprising HIV RNA from a patient, wherein the sample comprises the region spanning the HIV gag-protease coding sequence;

ii) reverse-transcribing and amplifying the HIV RNA with primers specific for the region spanning the HIV gag-protease coding sequence to obtain at least one amplicon comprising the region spanning the HIV gag-protease coding sequence, wherein at least one primer is selected from SEQ ID NO: 1 and SEQ ID NO: 8-10;

iii) generating a plasmid comprising a reference HIV sequence with a deletion of the region spanning the HIV gag-protease coding sequence;

iv) preparing at least one recombinant virus by recombination or ligation between at least one amplicon obtained in step ii) and the plasmid comprising the reference HIV sequence with a deletion of the region spanning the HIV gag-protease coding sequence obtained in step iii), and v) monitoring the at least one recombinant virus in the presence of the at least one drug to determine the phenotypic susceptibility of HIV to at least one drug, wherein said susceptibility is determined by the cytopathogenicity of said recombinant virus to cells or by determining the replicative capacity of said recombinant virus in the presence of at least one drug.

Furthermore the present disclosure also comprises an in vitro method for designing a drug regimen for an HIV-infected patient by determining the phenotypic susceptibility of HIV to at least one drug, comprising:

i) using at least one sample comprising HIV RNA from a patient, wherein the sample comprises the complete HIV reverse transcriptase-integrase coding sequence;

ii) reverse-transcribing and amplifying the HIV RNA with primers specific for the complete HIV reverse transcriptase-integrase coding sequence to obtain at least one amplicon comprising the complete HIV reverse transcriptase-integrase coding sequence, wherein at least one primer is selected from SEQ ID NO: 4-7;

iii) generating a plasmid comprising a reference HIV sequence with a deletion of the complete HIV reverse transcriptase-integrase coding sequence;

iv) preparing at least one recombinant virus by recombination or ligation between at least one amplicon obtained in step ii) and the plasmid comprising the reference HIV sequence with a deletion of the complete HIV reverse transcriptase-integrase coding sequence obtained in step iii), and v) monitoring the at least one recombinant virus in the presence of the at least one drug to determine the phenotypic susceptibility of HIV to at least one drug, wherein said susceptibility is determined by the cytopathogenicity of said recombinant virus to cells or by determining the replicative capacity of said recombinant virus in the presence of at least one drug.

The current invention also applies to an in vitro method for designing a drug regimen for an HIV-infected patient by determining the phenotypic susceptibility of HIV to at least one drug, comprising:

i) using at least one sample comprising HIV DNA, wherein the sample comprises the complete HIV gag-pol coding region;

ii) amplifying the HIV DNA with primers specific for the complete HIV gag-pol coding region to obtain at least one amplicon comprising the complete HIV gag-pol coding region, wherein at least one primer is selected from SEQ ID NO: 1-4;

iii) generating a plasmid comprising a reference HIV sequence with a deletion of the complete HIV gag-pol coding region;

iv) preparing at least one recombinant virus by recombination or ligation between at least one amplicon obtained in step ii) and the plasmid comprising the reference HIV sequence with a deletion of the complete HIV gag-pol coding region obtained in step iii), and v) monitoring the at least one recombinant virus in the presence of the at least one drug to determine the phenotypic susceptibility of HIV to at least one drug, wherein said susceptibility is determined by the cytopathogenicity of said recombinant virus to cells or by determining the replicative capacity of said recombinant virus in the presence of at least one drug.

In addition the disclosure describes an in vitro method for designing a drug regimen for an HIV-infected patient by determining the phenotypic susceptibility of HIV to at least one drug, comprising:

i) using at least one sample comprising HIV DNA, wherein the sample comprises the region spanning the HIV gag-protease coding sequence;

ii) amplifying the HIV DNA with primers specific for the region spanning the HIV gag-protease coding sequence to obtain at least one amplicon comprising the region spanning the HTV gag-protease coding sequence, wherein at least one primer is selected from SEQ ID NO: 1 and SEQ ID NO: 8-10;

iii) generating a plasmid comprising a reference HIV sequence with a deletion of the region spanning the HIV gag-protease coding sequence;

iv) preparing at least one recombinant virus by recombination or ligation between at least one amplicon obtained in step ii) and the plasmid comprising the reference HIV sequence with a deletion of the region spanning the HIV gag-protease coding sequence obtained in step iii), and v) monitoring the at least one recombinant virus in the presence of the at least one drug to determine the phenotypic susceptibility of HIV to at least one drug, wherein said susceptibility is determined by the cytopathogenicity of said recombinant virus to cells or by determining the replicative capacity of said recombinant virus in the presence of at least one drug.

The disclosure also comprises an in vitro method for designing a drug regimen for an HIV-infected patient by determining the phenotypic susceptibility of HIV to at least one drug, comprising:

i) using at least one sample comprising HIV DNA, wherein the sample comprises the complete HIV reverse transcriptase-integrase coding sequence;

ii) amplifying the HIV DNA with primers specific for the complete HIV reverse transcriptase-integrase coding sequence to obtain at least one amplicon comprising the complete HIV reverse transcriptase-integrase coding sequence, wherein at least one primer is selected from SEQ ID NO: 4-7;

iii) generating a plasmid comprising a reference HIV sequence with a deletion of the complete HIV reverse transcriptase-integrase coding sequence;

iv) preparing at least one recombinant virus by recombination or ligation between at least one amplicon obtained in step ii) and the plasmid comprising the reference HIV sequence with a deletion of the complete HIV reverse transcriptase-integrase coding sequence obtained in step iii), and v) monitoring the at least one recombinant virus in the presence of the at least one drug to determine the phenotypic susceptibility of HIV to at least one drug, wherein said susceptibility is determined by the cytopathogenicity of said recombinant virus to cells or by determining the replicative capacity of said recombinant virus in the presence of at least one drug.

A further embodiment of the invention is an in vitro method for determining the phenotypic susceptibility of HIV to at least one drug, comprising:

i) using at least one sample comprising HIV RNA from a patient, wherein the sample comprises the complete HIV gag-pol coding region;

ii) reverse-transcribing and amplifying said HIV RNA with primers specific for the complete HIV gag-pol coding region to obtain an amplicon comprising the complete HIV gag-pol coding region, wherein at least one primer is selected from SEQ ID NO: 1-4;

iii) determining the nucleotide sequence of the amplicon or a portion thereof as obtained in step ii), and iv) comparing the nucleotide sequence of the amplicon with the sequence of sequences whose phenotypic susceptibility is known to estimate the phenotypic susceptibility of HIV to at least one drug, wherein said susceptibility is determined by the cytopathogenicity of said recombinant virus to cells or by determining the replicative capacity of said recombinant virus in the presence of at least one drug.

Part of the invention is also wherein the embodiment is an in vitro method for determining the phenotypic susceptibility of HIV to at least one drug, comprising:

i) using at least one sample comprising HIV RNA from a patient, wherein the sample comprises the region spanning the HIV gag-protease coding sequence;

ii) reverse-transcribing and amplifying said HIV RNA with primers specific for the region spanning the HIV gag-protease coding sequence to obtain an amplicon comprising the region spanning the HIV gag-protease coding region, wherein at least one primer is selected from SEQ ID NO: 1 and SEQ ID NO: 8-10;

iii) determining the nucleotide sequence of the amplicon or a portion thereof as obtained in step ii), and iv) comparing the nucleotide sequence of the amplicon with the sequence of sequences whose phenotypic susceptibility is known to estimate the phenotypic susceptibility of HIV to at least one drug, wherein said susceptibility is determined by the cytopathogenicity of said recombinant virus to cells or by determining the replicative capacity of said recombinant virus in the presence of at least one drug.

In addition the invention relates to an in vitro method for determining the phenotypic susceptibility of HIV to at least one drug, comprising:

i) using at least one sample comprising HIV RNA from a patient, wherein the sample comprises the complete HIV reverse transcriptase-integrase coding sequence;

ii) reverse-transcribing and amplifying said HIV RNA with primers specific for the complete HIV reverse transcriptase-integrase coding sequence to obtain an amplicon comprising the complete HIV reverse transcriptase-integrase coding region, wherein at least one primer is selected from SEQ ID NO: 4-7;

iii) determining the nucleotide sequence of the amplicon or a portion thereof as obtained in step ii), and iv) comparing the nucleotide sequence of the amplicon with the sequence of sequences whose phenotypic susceptibility is known to estimate the phenotypic susceptibility of HIV to at least one drug, wherein said susceptibility is determined by the cytopathogenicity of said recombinant virus to cells or by determining the replicative capacity of said recombinant virus in the presence of at least one drug.

To the invention also belongs an in vitro method for determining the phenotypic susceptibility of HIV to at least one drug, comprising:

i) using at least one sample comprising HIV DNA wherein the sample comprises the complete HIV gag-pol coding region;

ii) amplifying said HIV DNA with primers specific for the complete HIV gag-pol coding region to obtain an amplicon comprising the complete HIV gag-pol coding region, wherein at least one primer is selected from SEQ ID NO: 1-4;

iii) determining the nucleotide sequence of the amplicon or a portion thereof as obtained in step ii), and iv) comparing the nucleotide sequence of the amplicon with the sequence of sequences whose phenotypic susceptibility is known to estimate the phenotypic susceptibility of HIV to at least one drug, wherein said susceptibility is determined by the cytopathogenicity of said recombinant virus to cells or by determining the replicative capacity of said recombinant virus in the presence of at least one drug.

The above embodiment of the invention can be extended to an in vitro method for determining the phenotypic susceptibility of HIV to at least one drug using at least one sample comprising HIV DNA wherein the sample comprises the region spanning the HIV gag-protease coding sequence using the appropriate primers SEQ ID NO: 1 and SEQ ID NO: 8-10 or wherein the sample comprises the complete HIV reverse transcriptase-integrase coding region using the appropriate primers selected from SEQ ID NO 4-7 respectively.

Part of the invention is also an in vitro method for designing a drug regimen for an HIV-infected patient by determining the phenotypic susceptibility of HIV to at least one drug, comprising:

i) using at least one sample comprising HIV RNA from a patient, wherein the sample comprises the complete HIV pol coding region;

ii) reverse-transcribing and amplifying the HIV RNA with primers specific for the complete HIV pol coding region to obtain at least one amplicon comprising the complete HIV pol coding region, wherein at least one primer is selected from SEQ ID NO's: 2, 4, 53 and 54;

iii) generating a plasmid comprising a reference HIV sequence with a deletion of the complete HIV pol coding region;

iv) preparing at least one recombinant virus by recombination or ligation between at least one amplicon obtained in step ii) and the plasmid comprising the reference HIV sequence with a deletion of the complete HIV pol coding region obtained in step iii), and v) monitoring at least one recombinant virus in the presence of at least one drug to determine the phenotypic susceptibility of HIV to at least one drug, wherein said susceptibility is determined by the cytopathogenicity of said recombinant virus to cells or by determining the replicative capacity of said recombinant virus in the presence of at least one drug.

In addition also to the invention belongs an in vitro method for designing a drug regime for an HIV-infected patient by determining the phenotypic susceptibility of HIV to at least one drug, comprising:

i) using at least one sample comprising HIV DNA, wherein the sample comprises the complete HIV pol coding region;

ii) amplifying the HIV DNA with primers specific for the complete HIV pol coding region to obtain at least one amplicon comprising the complete HIV pol coding region, wherein at least one primer is selected from SEQ ID NO: 2, 4, 53 and 54;

iii) generating a plasmid comprising a reference HIV sequence with a deletion of the complete HIV pol coding region;

iv) preparing at least one recombinant virus by recombination or ligation between at least one amplicon obtained in step ii) and the plasmid comprising the reference HIV sequence with a deletion of the complete HIV pol coding region obtained in step iii), and v) monitoring at least one recombinant virus in the presence of at least one drug to determine the phenotypic susceptibility of HIV to at least one drug, wherein said susceptibility is determined by the cytopathogenicity of said recombinant virus to cells or by determining the replicative capacity of said recombinant virus in the presence of at least one drug The disclosure further describes a method of constructing a genotypic and phenotypic database of HIV sequences, comprising:

i) using samples of HIV RNA from a patient comprising the complete HIV gag-pol coding region;

ii) reverse-transcribing and amplifying said HIV RNA with primers specific for the complete HIV gag-pol coding region to obtain an amplicon comprising the complete HIV gag-pol coding region, wherein at least one primer is selected from SEQ ID NO: 1-4;

iii) determining the nucleotide sequence of the amplicon or portions thereof as obtained in step ii);

iv) generating a plasmid comprising a reference HIV sequence with a deletion of the complete HIV gag-pol coding region;

v) preparing recombinant virus by recombination or ligation between the amplicon obtained in step ii) and the plasmid comprising the reference HIV sequence with a deletion of the complete HIV gag-pol coding region obtained in step iv);

vi) determining the relative replicative capacity of the recombinant virus in the presence of anti-HIV drugs compared to an HIV with a reference complete HIV gag-pol coding region.

The disclosure also comprises an in vitro method of constructing a genotypic and phenotypic database of HIV sequences, comprising:

i) using samples of HIV DNA comprising the complete HIV gag-pol coding region;

ii) amplifying said HIV DNA with primers specific for the complete HIV gag-pol coding region to obtain an amplicon comprising the complete HIV gag-pol coding region, wherein at least one primer is selected from SEQ ID NO: 1-4;

iii) determining the nucleotide sequence of the amplicon or portions thereof as obtained in step ii);

iv) generating a plasmid comprising a reference HIV sequence with a deletion of the complete HIV gag-pol coding region;

v) preparing recombinant virus by recombination or ligation between the amplicon obtained in step ii) and the plasmid comprising the reference HIV sequence with a deletion of the complete HIV gag-pol coding region obtained in step iv);

vi) determining the relative replicative capacity of the recombinant virus in the presence of anti-HIV drugs compared to an HIV virus with a reference complete HIV gag-pol coding region.

The above embodiments of the invention of constructing a genotypic and phenotypic database of HIV sequences can be extended to using at least one sample comprising either HIV RNA or DNA wherein the sample comprises the region spanning the HIV gag-protease coding sequence using the appropriate primers SEQ ID NO: 1 and SEQ ID NO: 8-10 or wherein the sample comprises the complete HIV reverse transcriptase-integrase coding region using the appropriate primers selected from SEQ ID NO 4-7 respectively.

Part of the invention is also a method of constructing a genotypic and phenotypic database of HIV sequences, comprising:

i) using samples of HIV RNA from a patient comprising the complete HIV pol coding region;

ii) reverse-transcribing and amplifying said HIV RNA with primers specific for the complete HIV pol coding region to obtain an amplicon comprising the complete HIV pol coding region, wherein at least one primer is selected from SEQ ID NO: 2, 4, 53 and 54;

iii) determining the nucleotide sequence of the amplicon or portions thereof as obtained in step ii);

iv) generating a plasmid comprising a reference HIV sequence with a deletion of the complete HIV pol coding region;

v) preparing recombinant virus by recombination or ligation between the amplicon obtained in step ii) and the plasmid comprising the reference HIV sequence with a deletion of the complete HIV pol coding region obtained in step iv);

vi) determining the relative replicative capacity of the recombinant virus in the presence of anti-HIV drugs compared to an HIV with a reference complete HIV pol coding region.

In addition to the invention also belongs an in vitro method of constructing a genotypic and phenotypic database of HIV sequences, comprising:

i) using samples of HIV DNA comprising the complete HIV pol coding region;

ii) amplifying said HIV DNA with primers specific for the complete HIV pol coding region to obtain an amplicon comprising the complete HIV pol coding region, wherein at least one primer is selected from SEQ ID NO: 2, 4, 53 and 54;

iii) determining the nucleotide sequence of the amplicon or portions thereof as obtained in step ii);

iv) generating a plasmid comprising a reference HIV sequence with a deletion of the complete HIV pol coding region;

v) preparing recombinant virus by recombination or ligation between the amplicon obtained in step ii) and the plasmid comprising the reference HIV sequence with a deletion of the complete HIV pol coding region obtained in step iv);

vi) determining the relative replicative capacity of the recombinant virus in the presence of anti-HIV drugs compared to an HIV virus with a reference complete HIV pol coding region.

The present invention also comprises the plasmids or sometimes called vectors described in the experimental part and the use of these plasmids or vectors in the methods described herein. The HIV sequence incorporated in the plasmid or vector may be based on the K03455 sequence. The complete HIV sequence may be incorporated or only part thereof. A suitable plasmid backbone may be selected from the group including pUC, pSV or pGEM.

To prepare vectors containing recombinant HIV gag-pol coding sequences, the patient derived gag-pol RNA was reverse transcribed and amplified by the polymerase chain reaction (PCR), then inserted into a vector containing the wild type HIV genome sequence but lacking a complete gag-pol coding region. Different primer combinations were initially used to obtain the amplified DNA sequences from patient samples. The 5' to 3' sequences and the primers identified as SEQ ID's NO: 1-10, more specifically SEQ ID NO's: 1-4 were successfully used to reverse transcribe and PCR amplify gag-pol coding region are listed below in Table 7.

To prepare a vector containing recombinant HIV gag-protease coding sequence, the patient derived gag-protease RNA was reverse transcribed and amplified by the polymerase chain reaction (PCR), then inserted into a vector containing the wild type HIV genome sequence but lacking gag-protease coding region. Different primer combinations were initially used to obtain the amplified DNA sequences from patient samples. The 5' to 3' sequences and the primers identified as SEQ ID's NO: 1-10, more specifically SEQ ID NO: 1 and SEQ ID NO's 8-10 were successfully used to reverse transcribe and PCR amplify gag-protease coding region are listed below in Table 7.

To prepare a vector containing recombinant HIV reverse transcriptase-integrase coding sequence, the patient derived reverse transcriptase-integrase RNA was reverse transcribed and amplified by the polymerase chain reaction (PCR), then inserted into a vector containing the wild type HIV genome sequence but lacking reverse transcriptase-integrase coding region. Different primer combinations were initially used to obtain the amplified DNA sequences from patient samples. The 5' to 3' sequences and the primers identified as SEQ ID's NO: 1-10, more specifically SEQ ID NO: 4-7 were successfully used to reverse transcribe and PCR amplify reverse transcriptase-integrase coding region are listed below in Table 7.

To prepare a vector containing recombinant HIV pol coding sequences, the patient derived pol RNA was reverse transcribed and amplified by the polymerase chain reaction (PCR), then inserted into a vector containing the wild type HIV genome sequence but lacking a complete pol coding region. Different primer combinations were initially used to obtain the amplified DNA sequences from patient samples. The 5' to 3' sequences and the primers identified as SEQ ID's NO: 2, 4, 53 and 54 were successfully used to reverse transcribe and PCR amplify pol coding region and are listed below in Table 7.

Reverse transcription and amplification may be performed with a single set of primers. Alternatively, more than one set of primers may be used in a hemi-nested approach to reverse transcribe and amplify the genetic material. Particularly, more than one set of primer is used in a nested approach. Following the generation of the recombinant construct, the chimeric virus may be grown and the viral titer determined (expressed as 50% cell culture infectious dose, CCID50) before proceeding to the determination of the phenotypic susceptibility.

"Chimeric" means a construct comprising nucleic acid material from different origin such as for example a combination of wild type HIV with a laboratory HIV virus, a combination of wild type HIV sequence and patient derived HIV sequence. The indicator gene, encoding a signal indicative of replication of the virus in the presence of a drug or indicative of the susceptibility of the virus in the presence of a drug may be present in the culturing cells such as MT-4 cells. In addition, said indicator gene may be incorporated in the chimeric construct introduced into the culturing cells or may be introduced separately. Suitable indicator genes encode fluorescent proteins, particularly green fluorescent protein (GFP) or mutants thereof such as eGFP (enhanced GFP).

Genetic material may be introduced into the cells using a variety of techniques known in the art including, calcium phosphate precipitation, liposomes, viral infection, and electroporation. The monitoring may be performed in high throughput.

A human immunodeficiency virus (HIV), as used herein refers to any HIV including laboratory HIV strains, wild type HIV strains, mutant HIV strains and any biological sample comprising HIV such as a HIV clinical isolate. HIV strains compatible with the present invention are those strains capable of infecting mammals, particularly humans such as HIV-1 and HIV-2. A patient may have HIV in his body with different mutations in the integrase (IN) gene. It is to be understood that a sample may contain a variety of different HIV containing different mutational profiles in the IN gene. A sample may be obtained for example from an individual, from cell cultures, or generated using recombinant technology, or cloning. Viral strains used for obtaining a plasmid are preferably HIV wild-type sequences, such as LAI or HXB2D. LAI, also known as IIIB, is a wild type HIV strain. One particular clone thereof, this means one sequence, is HXB2D. This sequence may be incorporated into a plasmid.

Instead of viral RNA, HIV DNA, e.g. proviral DNA, may be used for the methods described herein. In case RNA is used, reverse transcription into DNA by a suitable reverse transcriptase is needed. The protocols describing the analysis of RNA are also amenable for DNA analysis. However, if a protocol starts from DNA, the person skilled in the art will know that no reverse transcription is needed. The primers designed to amplify the RNA strand, also anneal to, and amplify DNA. Reverse transcription and amplification may be performed with a single set of primers. Suitably a hemi-nested and more suitably a nested approach may be used to reverse transcribe and amplify the genetic material.

Nucleic acid may be amplified by techniques such as polymerase chain reaction (PCR), nucleic acid sequence based amplification (NASBA), self-sustained sequence replication (3SR), transcription-based amplification (TAS), ligation chain reaction (LCR). Preferably the polymerase chain reaction is used.

Any type of patient sample may be used to obtain the integrase gene, such as serum or tissue. Viral RNA may be isolated using known methods such as described in Boom, R. et al. (J. Clin. Microbiol. 28(3): 495-503 (1990)). Alternatively, a number of commercial methods such as the QIAAMP® viral RNA kit (Qiagen, Inc.) or EasyMag RNA extraction platform (Biomérieux, Boxtel, the Netherlands) may be used to obtain viral RNA from bodily fluids such as plasma, serum, or cell-free fluids. DNA may be obtained by procedures known in the art (e.g. Maniatis, 1989) and commercial procedures (e.g. Qiagen).

According to the instant invention, for instance, the complete HIV gag and complete pol (Protease-reverse transcriptase-integrase) coding region (4588 bp) is used to prepare an amplicon.

"Amplicon" refers to the amplified, and where necessary, reverse transcribed complete gag-protease-reverse transcriptase-integrase sequence.

It should be understood that this complete gag-protease-reverse transcriptase-integrase sequence may be of diverse origin including plasmids and patient material. Suitably, the amplicon is obtained from patient material.

For the purpose of the present invention the amplicon is sometimes referred to as "DNA construct". A viral sequence may contain one or multiple mutations versus the consensus reference sequence given by HXB2D, GenBank accession number K03455. Said sequence, K03455, is present in Genbank and available through the Internet. A single mutation or a combination of mutations may correlate to a change in drug efficacy. This correlation may be indicative of an altered i.e. decreased or increased susceptibility of the virus for a drug. Said mutations may also influence the viral fitness.

A "drug" means any agent such as a chemotherapeutic, peptide, antibody, antisense, ribozyme and any combination thereof. Examples of drugs include protease inhibitors including darunavir, ritonavir, amprenavir, nelfinavir; reverse transcriptase inhibitors such as nevirapine, delavirdine, AZT, zidovudine, didanosine; integrase inhibitors; agents interfering with envelope (such as T-20).

Treatment or treatment regimen refers to the therapeutic management of an individual by the administration of drugs. Different drug dosages, administration schemes, administration routes and combinations may be used to treat an individual.

An alteration in viral drug sensitivity is defined as a change in susceptibility of a viral strain to said drug. Susceptibilities are generally expressed as ratios of $EC_{50}$ or $EC_{90}$ values (the $EC_{50}$ or $EC_{90}$ value being the drug concentration at which 50% or 90% respectively of the viral population is inhibited from replicating) of a viral strain under investigation compared to the wild type strain. Hence, the susceptibility of a viral strain towards a certain drug can be expressed as a fold change in susceptibility, wherein the fold change is derived from the ratio of for instance the $EC_{50}$ values of a mutant viral strain compared to the wild type $EC_{50}$ values. In particular, the susceptibility of a viral strain or population may also be expressed as resistance of a viral strain, wherein the result is indicated as a fold increase in $EC_{50}$ as compared to wild type $IC_{50}$.

The $IC_{50}$ is the drug concentration at which 50% of the enzyme activity is inhibited.

The susceptibility of HIV to a drug is tested by either determining the cytopathogenicity of the recombinant virus to cells or by determining the replicative capacity of the recombinant virus in the presence of at least one drug, relative to the replicative capacity of a wild type or reference HIV.

In the context of this invention, the cytopathogenic effect means the viability of the cells in culture in the presence of chimeric viruses. The cells may be chosen from T cells, monocytes, macrophages, dendritic cells, Langerhans cells, hematopoetic stem cells or precursor cells, MT4 cells and PM-1 cells. The cytopathogenicity may, for example, be followed microscopically, or replication might be monitored by the presence of any reporter molecule including reporter genes. A reporter gene is defined as a gene whose product has reporting capabilities. Suitable reporter molecules include tetrazolium salts, green fluorescent proteins, beta-galactosidase, chloramfenicol transferase, alkaline phophatase, and luciferase. Several methods of cytopathogenic testing including phenotypic testing are described in the literature comprising the recombinant virus assay (Kellam and Larder, Antimicrob. Agents Chemotherap. 1994, 38, 23-30, Hertogs et al. Antimicrob. Agents Chemotherap. 1998, 42, 269-276; Pauwels et al. J. Virol Methods 1988, 20, 309-321)

The susceptibility of HIV to a drug may also be determined by the replicative capacity of the recombinant virus in the presence of at least one drug, relative to the replicative capacity of a reference or wild type HIV. Replicative capacity means the ability of the virus or chimeric construct to grow under culturing conditions. This is sometimes referred to as viral fitness. The culturing conditions may contain triggers that influence the growth of the virus, examples of which are drugs. The methods for determining the susceptibility may be useful for designing a treatment regimen for an HIV-infected patient. For example, a method may comprise determining the replicative capacity of a clinical isolate of a patient and using said replicative capacity to determine an appropriate drug regime for the patient.

The phenotyping assays of the present invention can be performed at high throughput using, for example, a microtiter plate containing a variety of anti-HIV drugs. The present assays may be used to analyze the influence of changes at the HIV gag-pol gene to any type of drug useful to treat HIV. Examples of anti-HIV drugs that can be tested in this assay include, nucleoside and non-nucleoside reverse transcriptase inhibitors, nucleotide reverse transcriptase inhibitors, protease inhibitors, maturation inhibitors, RNaseH inhibitors and integrase inhibitors, but those of skill in the art will appreciate that other types of antiviral compounds may also be tested. The results may be monitored by several approaches including but not limited to morphology screening, microscopy, and optical methods, such as, for example, absorbance and fluorescence. An $IC_{50}$ value for each drug may be obtained in these assays and used to determine viral replicative capacity in the presence of the drug. Apart from $IC_{50}$ also e.g. $IC_{90}$ can be used. The replicative capacity of the viruses may be compared to that of a wild-type HIV virus to determine a relative replicative capacity value. Data from phenotypic assays may further be used to predict the behaviour of a particular HIV isolate to a given drug based on its genotype.

The assays of the present invention may be used for therapeutic drug monitoring. Said approach includes a combination of susceptibility testing, determination of drug level and assessment of a threshold. Said threshold may be derived from population based pharmacokinetic modelling (WO 02/23186). The threshold is a drug concentration needed to obtain a beneficial therapeutic effect in vivo. The in vivo drug level may be determined using techniques such as high performance liquid chromatography, liquid chromatography, mass spectroscopy or combinations thereof. The susceptibility of the virus may be derived from phenotyping or interpretation of genotyping results i.e. virtual phenotyping (WO 01/79540).

The assays of the present invention may be useful to discriminate an effective drug from an ineffective drug by establishing cut-offs i.e. biological cut-offs (see e.g. WO 02/33402). A biological cut-off is drug specific. These cut-offs are determined following phenotyping a large population of individuals containing wild type viruses. The cut-off is derived from the distribution of the fold increase in resistance of the virus for a particular drug.

The genotype of the patient-derived gag-pol coding region may be determined directly from the amplified DNA, i.e. the DNA construct by performing DNA sequencing. Alternatively, the sequence may be obtained after sub-cloning into a suitable vector. A variety of commercial sequencing enzymes and equipment may be used in this process. The efficiency may be increased by determining the sequence of the gag-pol coding region in several parallel reactions, each with a different set of primers. Such a process could be performed at high throughput on a multiple-well plate, for example. Commercially available detection and analysis systems may be used to determine and store the sequence information for later analysis.

The nucleotide sequence may be obtained using several approaches including sequencing nucleic acids. This sequencing may be performed using techniques including gel based approaches, mass spectroscopy and hybridisation. However, as more resistance related mutations are identified, the sequence at particular nucleic acids, codons or short sequences may be obtained. If a particular resistance associated mutation is known, the nucleotide sequence may be determined using hybridisation assays (including Biochips, LipA-assay), mass spectroscopy, allele specific PCR, or using probes or primers discriminating between mutant and wild-type sequence. A selected set of sequencing primers includes SEQ ID No's: 11-44 and 55-58 respectively (Table 10). This particular selection has the advantage that it enables the sequencing of the complete HIV gag-pol coding sequence. Consequently, using this set of primers all possible mutations that may occur in the HIV gag or pol gene may be detected.

The patient gag-pol genotype provides an additional means to determine drug susceptibility of a virus strain. Phenotyping is a lengthy process often requiring 2 or more weeks to accomplish. Therefore, systems have been developed which enable the prediction of the phenotype based on the genotypic results. The results of genotyping may be interpreted in conjunction with phenotyping and eventually be subjected to database interrogation. A suitable system is virtual phenotyping (WO 01/79540). In the virtual phenotyping process the complete gag-pol genes may be used. Alternatively, portions of the genes may be used. Also combinations of mutations, preferentially mutations indicative of a change in drug susceptibility, may be used. A combination of mutations is sometimes referred to as a hot-spot (see e.g. WO 01/79540). Briefly, in the process of virtual phenotyping, the genotype of a patient derived gag-pol sequence may be correlated to the phenotypic response of said patient derived gag-pol sequence. If no phenotyping is performed, the sequence may be screened towards a collection of sequences present in a database. Identical sequences are retrieved and the database is further interrogated to identify if a corresponding phenotype is known for any of the retrieved sequences. In this latter case a virtual phenotype may be determined. A report may be prepared including the $IC_{50}$ of the viral strain for one or more therapies, the sequence of the strain under investigation, and the biological cut-offs.

According to the methods described herein a database may be constructed comprising genotypic and phenotypic data of the HIV gag-pol sequences, wherein the database further provides a correlation between genotypes and phenotypes, wherein the correlation is indicative of efficacy of a given drug regimen. A database of gag-pol sequences may be created and used as described in WO 01/79540. For example, such a database may be analyzed in combination with gag, pol, protease, reverse transcriptase or integrase sequence information and the results used in the determination of appropriate treatment strategies. Said database containing a collection of genotypes, phenotypes and samples for which the combined genotype/phenotype are available, may be used to determine the virtual phenotype (see supra). In addition, instead of interrogating the complete gag-pol sequences, particular codons correlating to a change in drug susceptibility of the virus may be interrogated in such database.

A primer may be chosen from SEQ ID N° 1-10, 53 and 54. A particular set of primers is SEQ ID 1-4 and 53 and 54. Primers specific for the gag-pol region of the HIV genome such as the primers described herein and their homologs are disclosed to perform the assay according to the invention. The primer sequences listed herein may be labelled. Suitably, this label may be detected using fluorescence, luminescence or absorbance. The primer for creating a deletion construct may contain a portion that does not anneal to the HIV sequence. That portion may be used to introduce a unique restriction site. Interestingly, primers may be designed in which the unique restriction site is partially present in the HIV sequence. The primers are chosen from those listed herein or have at least 80% homology as determined by methods known by the person skilled in the art such BLAST or FASTA. Specifically, the homology is at least 90%, more specifically, at least 95%. In addition, primers located in a region of 50 nucleotides (nt) upstream or downstream from the sequences given herein constitute part of the invention. Especially, said region is 20 nucleotides up or downstream from the position in the HIV genome of the primer sequences given herein. Alternatively, primers comprising at least 8 consecutive bases present in either of the primers described here constitute one embodiment of the invention. Interestingly, the primers comprise at least 12 consecutive bases present in either of the primers described herein.

EXAMPLES

General Outline

An amplicon was generated from patient-derived plasma viral RNA by RT-PCR and nested PCR. This amplicon, further referred to as 5'LTR-Vif fragment, contains the complete Gag and complete Pol (PR-RT-INT) coding region (4588 bp). Sequence primers across the 5' end of HIV-1 allow for nucleotide sequence determination and genotypic drug resistance analysis.

A delta[Gag-Pol] backbone (SEQ ID NO: 49) was made starting from an HIV-1 vector that contains eGFP in the Nef coding region. In vitro cloning (using BD In-Fusion™, Clontech Laboratories Inc.) between the PCR-generated amplicon and the delta[Gag-Pol] backbone resulted in a fully replication-competent HIV-1 that was used in experiments to evaluate phenotypic drug resistance.

Further, an amplicon spanning the Gag cleavage sites p1/p7 and p1/p6, PR, RT, RNaseH and INT (3202 bp), referred to as Pol fragment, was evaluated together with an amplicon containing the Gag and PR coding sequence (1980 bp), referred to as Gag-PR fragment, and an amplicon containing the complete RT, RNaseH and INT coding sequence (2898 bp), named RT-INT fragment.

For phenotypic evaluation delta[Pol] (SEQ ID NO: 52) delta[Gag-PR] (SEQ ID NO: 50) and delta[RT-INT] HIV-1 (SEQ ID NO: 51) backbones, also containing eGFP (enhanced Green Fluorescent protein) in Nef, were designed respectively.

Protocol for amplification of 5'LTR-VIF fragment Starting from freshly prepared patient-derived RNA, 5 μl was mixed with 0.2 μM forward outer primer (5LTR_IF1=SEQ ID NO: 1) and 0.2 μM reverse outer primer (VIF_R2=SEQ ID NO: 2), 1× Superscript™ reaction buffer (containing 0.4 mM of each dNTP and 2.5 mM $MgSO_4$) and 0.5 μl Superscript™ III HIFI enzyme mix in a total volume of 25 μl (Table 1). The reverse transcription reaction was performed @ 53° C. for 30 min, followed by an initial denaturation @ 94° C. for 2 min. This was followed by 30 cycles of [denaturation @ 92° C. for 15 sec, annealing @ 55° C. for 30 sec and elongation @ 68° C. for 5 min]. The final elongation step was 10 min @ 68° C. (Table 2).

Subsequently, 1 μl of outer PCR product was mixed with 0.304 μM forward inner primer (5LTR_F2=SEQ ID NO: 3) and 0.304 μM reverse inner primer (VIF_R5=SEQ ID NO: 4), 1× Expand™ HIFI reaction buffer, 0.2 μl dNTP's (0.2 mM) and 0.3 μl Expand™ HIFI enzyme mix (=1.05 U) in a total volume of 25 μl (Table 1).

The inner PCR reaction consists of an initial denaturation @ 94° C. for 2 min, followed by 35 cycles of [denaturation @ 94° C. for 15 sec, annealing @ 61° C. for 30 sec and elongation @ 68° C. for 5 min]. The final elongation step was 10 min @ 68° C. (Table 2).

All reaction mixtures and samples were kept on ice during preparation. The outer and inner primers used to generate this amplicon can be found in Table 7.

Finally, 4 μl PCR product was mixed with 2 μl loading dye, loaded on a 1% agarose gel and stained with ethidium bromide for visualization.

TABLE 1

Composition of the RT-outer PCR mix and inner PCR mix for amplification of the 5'LTR-VIF fragment.

| component | volume/sample (μl) |
|---|---|
| RT-outer PCR mix | |
| DEPC•water | 6.5 |
| 2 × reaction buffer | 12.5 |
| 5LTR_IF1 primer (20 μM) | 0.25 |
| VIF_R2 primer (20 μM) | 0.25 |
| Superscript III HiFi | 0.5 |
| RNA | 5 |
| total volume (μl) | 25 |
| inner PCR mix | |
| DEPC•water | 20.24 |
| 10 × reaction buffer | 2.5 |
| 5LTR_F2 primer (20 μM) | 0.38 |
| VIF_R5 primer (20 μM) | 0.38 |
| dNTP's (25 mM) | 0.2 |
| Expand HiFi (3.5 U/μl) | 0.3 |
| OUT_sample | 1 |
| total volume (μl) | 25 |

TABLE 2

Thermal cycling conditions for the outer and inner PCR for amplification of the 5'LTR-VIF fragment.

| outer PCR 5'LTR-VIF fragment | | | | inner PCR 5'LTR-VIF fragment | | | |
|---|---|---|---|---|---|---|---|
| step | temperature (° C.) | time | cycles | step | temperature (° C.) | time | cycles |
| 1 | 53 | 30 min | | 1 | 94 | 2 min | |
| 2 | 94 | 2 min | | 2 | 94 | 15 s | 35 |
| 3 | 92 | 15 s | 30 | 3 | 61 | 30 s | |
| 4 | 55 | 30 s | | 4 | 68 | 5 min | |
| 5 | 68 | 5 min | | 5 | 68 | 10 min | |
| 6 | 68 | 10 min | | 6 | 4 | hold | |
| 7 | 4 | hold | | | | | |

Protocol for Amplification of Pol Fragment

Starting from freshly prepared patient-derived RNA, 5 μl was mixed with 0.2 μM forward outer primer (5'OUT=SEQ ID NO: 53) and 0.2 μM reverse outer primer (VIF_R2=SEQ ID NO: 2), 1× Superscript™ reaction buffer (containing 0.4 mM of each dNTP and 2.5 mM $MgSO_4$) and 0.5 μl Superscript™ III HIFI enzyme mix in a total volume of 25 μl (Table 12). The reverse transcription reaction was performed @ 53° C. for 30 min, followed by an initial denaturation @ 94° C. for 2 min. This was followed by 30 cycles of [denaturation @ 92° C. for 15 sec, annealing @ 55° C. for 30 sec and elongation @ 68° C. for 3 min 30 sec]. The final elongation step was 10 min @ 68° C. (Table 13).

Subsequently, 1 μl of outer PCR product was mixed with 0.304 μM forward inner primer (5'IN=SEQ ID NO: 54) and 0.304 μM reverse inner primer (VIF_R5=SEQ ID NO: 4), 1× Expand™ HIFI reaction buffer, 0.2 μl dNTP's (0.2 mM) and 0.3 μl Expand™ HIFI enzyme mix (=1.05 U) in a total volume of 25 μl (Table 12). The inner PCR reaction consists of an initial denaturation @ 94° C. for 2 min, followed by 35 cycles of [denaturation @ 94° C. for 15 sec, annealing @ 58° C. for 30 sec and elongation @ 68° C. for 3 min 30 sec]. The final elongation step was 10 min @ 68° C. (Table 13).

All reaction mixtures and samples were kept on ice during preparation. The outer and inner primers used to generate this amplicon can be found in Table 7.

Finally, 4 μl PCR product was mixed with 2 μl loading dye, loaded on a 1% agarose gel and stained with ethidium bromide for visualization.

TABLE 12

Composition of the RT-outer PCR mix and inner PCR mix for amplification of the Pol fragment.

| component | volume/sample (μl) |
|---|---|
| **RT-outer PCR mix** | |
| DEPC•water | 6.5 |
| 2 × reaction buffer | 12.5 |
| 5LTR_IF1 primer (20 μM) | 0.25 |
| VIF_R2 primer (20 μM) | 0.25 |
| Superscript III HiFi | 0.5 |
| RNA | 5 |
| total volume (μl) | 25 |
| **inner PCR mix** | |
| DEPC•water | 20.24 |
| 10 × reaction buffer | 2.5 |
| 5LTR_F2 primer (20 μM) | 0.38 |
| VIF_R5 primer (20 μM) | 0.38 |
| dNTP's (25 mM) | 0.2 |
| Expand HiFi (3.5 U/μl) | 0.3 |
| OUT_sample | 1 |
| total volume (μl) | 25 |

TABLE 13

Thermal

| outer PCR Pol fragment | | | | inner PCR Pol fragment | | | |
|---|---|---|---|---|---|---|---|
| step | temperature (° C.) | time | cycles | step | temperature (° C.) | time | cycles |
| 1 | 53 | 30 min | | 1 | 94 | 2 min | |
| 2 | 94 | 2 min | | 2 | 94 | 15 s | 35 |
| 3 | 92 | 15 s | 30 | 3 | 58 | 30 s | |
| 4 | 55 | 30 s | | 4 | 68 | 3 min 30 sec | |
| 5 | 68 | 3 min 30 sec | | 5 | 68 | 10 min | |
| 6 | 68 | 10 min | | 6 | 4 | hold | |
| 7 | 4 | hold | | | | | |

Protocol for Amplification of RT-INT Fragment

Starting from freshly prepared patient-derived RNA, 5 μl was mixed with 0.2 μM forward outer primer (PR_F1=SEQ ID NO: 5) and 0.2 μM reverse outer primer (VIF_R3=SEQ ID NO: 6), 1× Superscript™ reaction buffer (containing 0.4 mM of each dNTP and 2.5 mM $MgSO_4$) and 0.5 μl Superscript™ III HIFI enzyme mix in a total volume of 25 μl (Table 3). The reverse transcription reaction was performed @ 56° C. for 30 min, followed by an initial denaturation @ 94° C. for 2 min. This was followed by 30 cycles of [denaturation @ 92° C. for 15 sec, annealing @ 62° C. for 30 sec and elongation @ 68° C. for 3 min 30 sec]. The final elongation step was 10 min @ 68° C. (Table 4).

Subsequently, 1 μA of outer PCR product was mixed with 0.304 μM forward inner primer (PR_F3=SEQ ID NO: 7) and 0.304 μM reverse inner primer (VIF_R5=SEQ ID NO: 4), 1× Expand™ HIFI reaction buffer, 0.2 μl dNTP's (0.2 mM) and 0.3 μl Expand™ HIFI enzyme mix (=1.05 U) in a total volume of 25 μl (Table 3). The inner PCR reaction consists of an initial denaturation @ 94° C. for 2 min, followed by 35 cycles of [denaturation @ 94° C. for 15 sec, annealing @ 60° C. for 30 sec and elongation @ 68° C. for 3 min]. The final elongation step was 10 min @ 68° C. (Table 4).

All reaction mixtures and samples were kept on ice during preparation. The outer and inner primers used to generate this amplicon can be found in Table 7.

Finally, 4 μl PCR product was mixed with 2 μl loading dye, loaded on a 1% agarose gel and stained with ethidium bromide for visualization.

TABLE 3

Composition of the RT-outer PCR mix and inner PCR mix for amplification of the RT-INT fragment.

| component | volume/sample (μl) |
|---|---|
| **RT-outer PCR mix** | |
| DEPC•water | 6.5 |
| 2 × reaction buffer | 12.5 |
| PR_F1 (20 μM) | 0.25 |
| VIF_R3 (20 μM) | 0.25 |
| Superscript III HiFi | 0.5 |
| RNA | 5 |
| total volume (μl) | 25 |
| **inner PCR mix** | |
| DEPC•water | 20.24 |
| 10 × reaction buffer | 2.5 |
| PR_F3 (20 μM) | 0.38 |
| VIF_R5 (20 μM) | 0.38 |
| dNTP's (25 mM) | 0.2 |
| Expand HiFi (3.5 U/μl) | 0.3 |
| OUT_sample | 1 |
| total volume (μl) | 25 |

TABLE 4

Thermal cycling conditions for the outer and inner PCR for amplification of the RT-INT fragment.

| outer PCR RT-INT fragment | | | | inner PCR RT-INT fragment | | | |
|---|---|---|---|---|---|---|---|
| step | temperature (° C.) | time | cycles | step | temperature (° C.) | time | cycles |
| 1 | 53 | 30 min | | 1 | 94 | 2 min | |
| 2 | 94 | 2 min | | 2 | 94 | 15 s | 35 |
| 3 | 92 | 15 s | 30 | 3 | 60 | 30 s | |
| 4 | 55 | 30 s | | 4 | 68 | 3 min | |
| 5 | 68 | 3 min 30 s | | 5 | 68 | 10 min | |
| 6 | 68 | 10 min | | 6 | 4 | hold | |
| 7 | 4 | hold | | | | | |

Protocol for Amplification of GAG-PR Fragment

Starting from freshly prepared patient-derived RNA, 5 μl was mixed with 0.2 μM forward outer primer (EF1=SEQ ID NO: 8) and 0.2 μM reverse outer primer (Gaprout-R3=SEQ ID NO: 9), 1× Superscript™ reaction buffer (containing 0.4 mM of each dNTP and 2.5 mM $MgSO_4$) and 0.5 ml Superscript™ III HIFI enzyme mix in a total volume of 25 μl (Table 5). The reverse transcription reaction was performed @ 53° C. for 30 min, followed by an initial denaturation @ 94° C. for 2 min. This was followed by 30 cycles of [denaturation @ 92° C. for 15 sec, annealing @ 55° C. for 30 sec and elongation @ 68° C. for 2 min 30 sec]. The final elongation step was 10 min @ 68° C. (Table 6).

Subsequently, 1 ml of outer PCR product was mixed with 0.304 μM forward inner primer (5LTR_IF1=SEQ ID NO:1) and 0.304 μM reverse inner primer (Gaprout-R1=SEQ ID NO: 10), 1× Expand™ HIFI reaction buffer, 0.2 μl dNTP's (0.2 mM) and 0.3 ml Expand™ HIFI enzyme mix (=1.05 U) in a total volume of 25 μl (Table 5). The inner PCR reaction consists of an initial denaturation @ 94° C. for 2 min, followed by 35 cycles of [denaturation @ 94° C. for 15 sec, annealing @ 60° C. for 30 sec and elongation @ 72° C. for 2 min]. The final elongation step was 10 min @ 72° C. (Table 6). All reaction mixtures and samples were kept on ice during preparation. The outer and inner primers used to generate this amplicon can be found in Table 7.

Finally, 4 μl PCR product was mixed with 2 μl loading dye, loaded on a 1% agarose gel and stained with ethidium bromide for visualization.

TABLE 5

Composition of the RT-outer PCR mix and inner PCR mix for amplification of the GAG-PR fragment.

| component | volume/sample (μl) |
|---|---|
| RT-outer PCR mix | |
| DEPC•water | 6.5 |
| 2 × reaction buffer | 12.5 |
| EF1 (20 μM) | 0.25 |
| Gaprout-R3 (20 μM) | 0.25 |
| Superscript III HiFi | 0.5 |
| RNA | 5 |
| total volume (μl) | 25 |
| Inner PCR mix | |
| DEPC•water | 20.24 |
| 10 × reaction buffer | 2.5 |
| 5LTR_IF1 (20 μM) | 0.38 |
| Gaprout-R1 (20 μM) | 0.38 |
| dNTP's (25 mM) | 0.2 |
| Expand HiFi (3.5 U/μl) | 0.3 |
| OUT_sample | 1 |
| total volume (μl) | 25 |

TABLE 6

Thermal cycling conditions for the outer and inner PCR for amplification of the GAG-PR fragment.

| outer PCR Gag-PR fragment | | | | inner PCR Gag-PR fragment | | | |
|---|---|---|---|---|---|---|---|
| step | temperature (° C.) | time | cycles | step | temperature (° C.) | time | cycles |
| 1 | 53 | 30 min | | 1 | 94 | 2 min | |
| 2 | 94 | 2 min | | 2 | 94 | 15 s | 35 |
| 3 | 92 | 15 s | 30 | 3 | 60 | 30 s | |
| 4 | 55 | 30 s | | 4 | 72 | 2 min | |
| 5 | 68 | 2 min 30 s | | 5 | 72 | 10 min | |
| 6 | 68 | 10 min | | 6 | 4 | hold | |
| 7 | 4 | hold | | | | | |

TABLE 7

Primer sequences of all amplification primers and their position on the HXB2 reference.

| primer name | primer sequence from 5' to 3' | position on HXB2 |
|---|---|---|
| EF1 | CAA GTA GTG TGT GCC CGT CTG T | 550-571 |
| 5LTR_IF1 | TGG AAA ATC TCT AGC AGT GGC G | 619-640 |
| 5LTR_F2 | TCT CTA GCA GTG GCG CCC GAA CA | 626-648 |
| PR_F1 | CCC TCA AAT CAC TCT TTG GCA ACG AC | 2252-2277 |
| PR_F3 | GCT CTA TTA GAT ACA GGA GCA GAT G | 2316-2340 |
| VIF_R2 | AGT GGG ATG TGT ACT TCT GAA C | 5195-5216 |
| VIF_R3 | CTC CTG TAT GCA GAC CCC AAT ATG | 5243-5266 |
| VIF_R5 | GGG ATG TGT ACT TCT GAA CTT | 5193-5213 |
| Gaprout-R3 | CCA TTG TTT AAC TTT TGG GCC ATC C | 2597-2621 |
| Gaprout-R1 | CCA TTC CTG GCT TTA ATT TTA CTG G | 2574-2598 |
| 5' OUT | GCC CCT AGG AAA AAG GGC TGT TGG | 2008-2031 |
| 5' IN | CTA GGA AAA AGG GCT GTT GGA AAT G | 2012-2036 |

SEQ ID NO 1: (5LTR_IF1) TGG AAA ATC TCT AGC AGT GGC G

SEQ ID NO 2: (VIF_R2) AGT GGG ATG TGT ACT TCT GAA C

SEQ ID NO 3: (5LTR_F2) TCT CTA GCA GTG GCG CCC GAA CA

SEQ ID NO 4: (VIF_R5) GGG ATG TGT ACT TCT GAA CTT

SEQ ID NO 5: (PR_F1) CCC TCA AAT CAC TCT TTG GCA ACG AC

SEQ ID NO 6: (VIF_R3) CTC CTG TAT GCA GAC CCC AAT ATG

SEQ ID NO 7: (PR_F3) GCT CTA TTA GAT ACA GGA GCA GAT G

SEQ ID NO 8: (EF1) CAA GTA GTG TGT GCC CGT CTG T

SEQ ID NO 9: (Gaprout-R3) CCA TTG TTT AAC TTT TGG GCC ATC C

SEQ ID NO 10: (Gaprout-R1) CCA TTC CTG GCT TTA ATT TTA CTG G

SEQ ID NO 53 (5'OUT) GCC CCT AGG AAA AAG GGC TGT TGG

SEQ ID NO 54 (5'IN) CTA GGA AAA AGG GCT GTT GGA AAT G

Sequencing Protocol for all Fragments Mentioned Before

Sequencing reactions were performed with the Big Dye Terminator Cycle Sequencing Kit v3.1 (Applied Biosystems). Each reaction mixture (11.5 μl) contained: the amplicon (1 μl), DNase RNase free water (3 μl), Big Dye terminator mix (1 μl), primer (4 μl, 4 μM) and 1× dilution buffer (1.0 M Tris HCL, 1.0 M $MgCl_2$ and $H_2O$) (Table 8). All primers used for nucleotide sequencing of the different fragments are listed in Table 10.

The PCR conditions were 25 cycles of [10 seconds at 96° C., 5 seconds at 50° C. and 4 minutes at 60° C.], followed by a final hold at 4° C. and using an ABI 9800 Fast Thermal Cycler (Applied Biosystems) (Table 9).

The purification of the sequencing reaction mixtures was performed using the DyeEX (Qiagen) purification kit according to the manufacturer's protocol. The sequencing was performed using an ABI3730 XL (Applied Biosystems) and the generated sequences were aligned and analyzed using SeqScape v2.5 software (Applied Biosystems).

TABLE 8

Composition of the sequencing reaction mixture.

| component | vol/sample (μl) |
|---|---|
| DEPC•water | 3 |
| 2.5 × dilution buffer | 2.5 |
| Big Dye terminator mix | 1 |
| primer (4 μM) | 4 |
| template | 1 |
| total volume (μl) | 11.5 |

Thermal Cycling Program

TABLE 9

Thermal cycling conditions for the sequencing reaction.

| step | temp. | time | # cycles |
|---|---|---|---|
| 1 | 96° C. | 10 s | 25 |
| 2 | 50° C. | 5 s | |

TABLE 9-continued

Thermal cycling conditions for the sequencing reaction.

| step | temp. | time | # cycles |
|---|---|---|---|
| 3 | 60° C. | 4 min | |
| 4 | 4° C. | hold | |

TABLE 10

Primer sequences of all sequencing primers and their position on the HXB2 reference.

| | Primer name | Nucleotide sequence (5' → 3') | Position on HXB2 |
|---|---|---|---|
| *Forward Primers* | | | |
| SEQ ID NO 11 | 5'LTR_F_631 | AGCAGTGGCGCCCGAACAG | 631-649 |
| SEQ ID NO 12 | F0 gag | TTTGACTAGCGGGAGGCTAGAAG | 761-782 |
| SEQ ID NO 13 | GAG_F_1070 | TAAAAGACACCAAGGAAGC | 1070-1088 |
| SEQ ID NO 14 | F10 gag | AAGACACCAAGGAAGC | 1073-1088 |
| SEQ ID NO 15 | F3 gag | CATAGCAGGAACTACTAGTA | 1494-1513 |
| SEQ ID NO 16 | GAG_F_1602 | TAAAATAGTAAGAATGTATAGCCC | 1602-1625 |
| SEQ ID NO 17 | F5 gag | ATGACAGCATGTCAGGGAGT | 1828-1847 |
| SEQ ID NO 18 | F1 | GAGAGCTTCAGGTTTGGGG | 2170-2188 |
| SEQ ID NO 19 | F5 | CACTCTTTGGCAACGACCC | 2261-2279 |
| SEQ ID NO 20 | PR_F2376 | TGGAAACCAAAAATGATAGG | 2376-2395 |
| SEQ ID NO 21 | F2 | AATTGGGCCTGAAAATCC | 2696-2713 |
| SEQ ID NO 22 | F3 | CCTCCATTCCTTTGGATGGG | 3222-3241 |
| SEQ ID NO 23 | RT_F_3681 | GAAAGCATAGTAATATGGG | 3681-3699 |
| SEQ ID NO 24 | IN_F_4074 | CAACCAGATAAAAGTGAATCAG | 4074-4095 |
| SEQ ID NO 25 | IN_F_4540 | TAGCAGGAAGATGGCCAGT | 4540-4558 |
| SEQ ID NO 26 | Inseq3F | GTAGACATAATAGCAACAGAC | 4830-4850 |
| SEQ ID NO 55 | F7 | GTACTGGATGTGGGTGATGC | 2871-2890 |
| SEQ ID NO 56 | F8 | GTGGGAAAATTGAATTGGG | 3330-3348 |
| SEQ ID NO 57 | F3771 | GCCACCTGGATTCCTGAGTG | 3771-3790 |
| *Reverse primers* | | | |
| SEQ ID NO 27 | R8 gag | TCTTGTGGGGTGGCTCCTTC | 1337-1318 |
| SEQ ID NO 28 | GAG_R_1316 | TCTTGTGGGGTGGCTCCTTCTG | 1337-1316 |
| SEQ ID NO 29 | R3 gag | TCTACATAGTCTCTAAAGGG | 1682-1663 |
| SEQ ID NO 30 | GAG_R_1825 | ACTCCCTGACATGCTGTCATCAT | 1847-1825 |
| SEQ ID NO 31 | R7 gag | GTGGGGCTGTTGGCTCTGGT | 2164-2145 |
| SEQ ID NO 32 | PR_R_2382 | ATTCCCCCTATCATTTTTGG | 2401-2382 |
| SEQ ID NO 33 | R8 | GATAAAACCTCCAATTCC | 2414-2397 |
| SEQ ID NO 34 | R3 | CTTCCCAGAAGTCTTGAGTTC | 2817-2797 |
| SEQ ID NO 35 | R6 | GGAATATTGCTGGTGATCC | 3030-3012 |
| SEQ ID NO 36 | RT_R_3304 | TGTATGTCATTGACAGTCC | 3322-3304 |
| SEQ ID NO 37 | R5 | GGGTCATAATACACTCCATG | 3511-3492 |

TABLE 10-continued

Primer sequences of all sequencing primers and their position on the HXB2 reference.

| | Primer name | Nucleotide sequence (5' → 3') | Position on HXB2 |
|---|---|---|---|
| SEQ ID NO 38 | R1 | CTCCCACTCAGGAATCC | 3794-3778 |
| SEQ ID NO 39 | RT_R_3964 | CAGTCTTCTGATTTGTTG | 3981-3964 |
| SEQ ID NO 40 | RT_R_4150 | CTTTGTGTGCTGGTACCCATG | 4170-4150 |
| SEQ ID NO 41 | RT_R_4380a | GGACTACAGTCTACTTGTCCAATG | 4402-4380 |
| SEQ ID NO 42 | Inseq2R | CTGCCATTTGTACTGCTGTC | 4767-4748 |
| SEQ ID NO 43 | IN_R_5042 | ATCACCTGCCATCTGTTTTCCA | 5063-5042 |
| SEQ ID N0 44 | VIF_R_5193 | ATGTGTACTTCTGAACTT | 5210-5193 |
| | | Forward Primers | |
| SEQ ID NO 58 | IN_R_4348 | CTCCTTTTAGCTGACATTTATCAC | 4371-4348 |

Creation of the HXB2D_eGFP_delta[GAG-POL] Backbone (SEQ ID NO: 49)

This backbone contains all genetic elements of HIV-1, except the complete GAG and POL region. Recombination between this GAG-POL deletion backbone and the 5'LTR-VIF amplicon resulted in a fully functional HIV-1 viral vector, which was used in transfection/infection experiments.

First, pUC18 was digested with PstI and EcoRI restriction enzymes. Subsequently, a 35 bp synthetic linker containing the HpaI, SpeI, and SalI restriction sites was ligated into the PstI/EcoRI-linearized pUC 18 plasmid, creating pUC 18-LINK. Next, HXB2D_eGFP (original fully replication competent HIV-1 vector, containing eGFP in Nef) was digested with HpaI and SalI (termed vector C), cutting out the 5' part of the HIV-1 genome (5'LTR, GAG, POL, VIF) (from nucleotide 15223 to 5786 compared to the HXB2 reference), termed fragment A. Fragment A was then cloned into the HpaI/SalI-digested pUC18-LINK plasmid. PCR primers that are complementary to the 5' and 3' ends of the 5'LTR-Vif amplicon were designed and used in an 'inverse PCR' (iPCR) reaction to 're-create' the nucleotide sequence that was removed in excess during HpaI/SalI digestion (i.e. sequence between primer binding site and restriction site). These inverse PCR primers were extended with the nucleotide sequences of two restriction sites (i.e. PacI and SnaBI) for linearization of the backbone afterwards. Finally, HpaI/SalI digestion was performed on the iPCR product and the excised HpaI/SalI fragment (fragment B) was cloned back into the HpaI/SalI digested original HXB2D-eGFP vector (vector C) (see FIG. 1, 2, 3).

Creation of the HXB2D_eGFP_delta[POL] Backbone (SEQ ID NO: 52)

This backbone contains all genetic elements of HIV-1, except the complete Pol region. Recombination between this Pol deletion backbone and the Pol amplicon resulted in a fully functional HIV-1 viral vector, which was used in transfection/infection experiments.

First, pUC18 was digested with PstI and EcoRI restriction enzymes. Subsequently, a 35 bp synthetic linker containing the HpaI, SpeI, and SalI restriction sites was ligated into the PstI/EcoRI-linearized pUC18 plasmid, creating pUC18-LINK. Next, HXB2D_eGFP (original fully replication competent HIV-1 vector, containing eGFP in Nef) was digested with HpaI and Sail (termed vector C), cutting out the 5' part of the HIV-1 genome (5'LTR, GAG, POL, VIF) (from nucleotide 15223 to 5786 compared to the HXB2 reference), termed fragment A. Fragment A was then cloned into the HpaI/SalI-digested pUC18-LINK plasmid. PCR primers that are complementary to the 5' and 3' ends of the Pol amplicon were designed and used in an 'inverse PCR' (iPCR) reaction to 're-create' the nucleotide sequence that was removed in excess during HpaI/SalI digestion (i.e. sequence between primer binding site and restriction site). These inverse PCR primers were extended with the nucleotide sequences of two restriction sites (i.e. Pad and SnaBI) for linearization of the backbone afterwards. Finally, HpaI/SalI digestion was performed on the iPCR product and the excised HpaI/SalI fragment (fragment P) was cloned back into the HpaI/SalI digested original HXB2D-eGFP vector (vector C) (see FIGS. 12 and 13).

Creation of the HXB2D_eGFP_delta[RT-INT] Backbone (SEQ ID NO: 51)

This backbone contains all genetic elements of HIV-1, except the complete RT and INT region. Recombination between this RT-INT deletion backbone and the RT-INT amplicon resulted in a fully functional HIV-1 viral vector, which was used in transfection/infection experiments.

First, pUC18 was digested with PstI and EcoRI restriction enzymes. Subsequently, a 35 bp synthetic linker containing the HpaI, SpeI, and SalI restriction sites was ligated into the PstI/EcoRI-linearized pUC18 plasmid, creating pUC18-LINK. Next, HXB2D_eGFP (original fully replication competent HIV-1 vector, containing eGFP in Nef) was digested with SpeI and SalI (termed vector Z), cutting out the majority of POL and VIF of the HIV-1 genome (from nucleotide 1507 to 5786 compared to the HXB2 reference), termed fragment X. Fragment X was then cloned into the SpeI/SalI-digested pUC18-LINK plasmid. PCR primers that are complementary to the 5' and 3' ends of the RT-INT amplicon were designed and used in an 'inverse PCR' (iPCR) reaction to 're-create' the nucleotide sequence that was removed in excess during SpeI/SalI digestion (i.e. sequence between primer binding site and restriction site).

Finally, SpeI/SalI digestion was done on the iPCR product and the excised SpeI/SalI fragment (fragment Y) was cloned back into the SpeI/SalI digested original HXB2D-eGFP vector (vector Z) (see FIG. 4, 5, 6).

Creation of the HXB2D_eGFP_delta[GAG-PR] Backbone (SEQ ID NO: 50)

This backbone contains all genetic elements of HIV-1, except the complete GAG and PR region. Recombination between this GAG-PR deletion backbone and the GAG-PR amplicon resulted in a fully functional HIV-1 viral vector, which was used in transfection/infection experiments.

First, pUC18 was digested with PstI and EcoRI restriction enzymes. Subsequently, a 35 bp synthetic linker containing the HpaI, SpeI, and San restriction sites was ligated into the PstI/EcoRI-linearized pUC18 plasmid, creating pUC18-LINK. Next, HXB2D_eGFP (original fully replication competent HIV-1 vector, containing eGFP in Nef) was digested with HpaI and SalI (termed vector C), cutting out the 5' part of the HIV-1 genome (5'LTR, GAG, POL, VIF) (from nucleotide 15223 to 5786 compared to the HXB2 reference), termed fragment A. Fragment A was then cloned into the HpaI/SalI-digested pUC18-LINK plasmid. PCR primers that are complementary to the 5' and 3' ends of the GAG-PR amplicon were designed and used in an 'inverse PCR' (iPCR) reaction to 're-create' the nucleotide sequence that was removed in excess during HpaI/SalI digestion (i.e. sequence between primer binding site and restriction site). Finally, HpaI/SalI digestion was done on the iPCR product and the excised HpaI/SalI fragment (fragment ALPHA) was cloned back into the HpaI/SalI digested original HXB2D-eGFP vector (vector C) (see FIG. 7, 8, 9).

Phenotypic Assay Approach

After linearization of the Gag-Pol, Gag-PR and RT-INT HXB2D_eGFP_delta backbone described before, the respective purified amplicon was cloned in the appropriate backbone using the In-Fusion™ technology (Clontech, Mountain view, Calif.) and subsequently transformed into MAX Efficiency® Stb12™ cells (Invitrogen, Merelbeke, Belgium). After DNA preparation from either clones or the complete plate, full-length recombinant HIV genomes were transfected to MT4 cells. At full CPE, recombinant virus stocks were harvested, titrated and subjected to an antiviral experiment.

The 3 phenotyping assays (GAG-POL, GAG-PR and RT-INT) are described in the following section. The layout of the experiments is shown in FIG. 10.

The three backbones, HXB2D_eGFP_delta [GAG-POL] (SEQ ID NO: 49), HXB2D_eGFP_delta [GAG-PR] (SEQ ID NO: 50) and HXB2D_eGFP_delta [RT-INT] (SEQ ID NO: 51) were linearized by digestion with SnaBI and PacI. After purification, for each backbone, 100 ng linearized vector was recombined with three different PCR amplicons (3×5'LTR-VTF, 3×GAG-PR or 3×RT-INT amplicons) in vector/insert molar ratio of 1/10 using In-Fusion reagents. Thereafter, In-Fusion mixes were transformed to MAX Efficiency Stb12 cells and incubated for 24 h at 30° C. The day after, colonies were screened for the presence of the full recombinant plasmid by a duplex colony PCR using the primers shown in Table 11 (SEQ ID NO's: 45-48).

As an example, full recombinants generate two fragments (493 bp and 217 bp), while recircularized vectors containing no inserts, generate only one fragment (300 bp for delta [GAG-POL], 200 bp for delta_[GAG-PR] and 500 bp for delta [RT-INT]). In general full-length HIV recombinants were obtained for all backbones and for all amplicons tested.

For the GAG-POL assay, two full recombinants were obtained for sample 1 and 2, and three recombinants for sample 3.

For the GAG-PR backbone, two recombinants were generated for sample 1, one recombinant for sample 2 and eight recombinants for sample 3.

For the RT-INT backbone, five full recombinants for sample 1, eleven recombinants for sample 2 and two for sample 3 were generated.

Figure 11B:
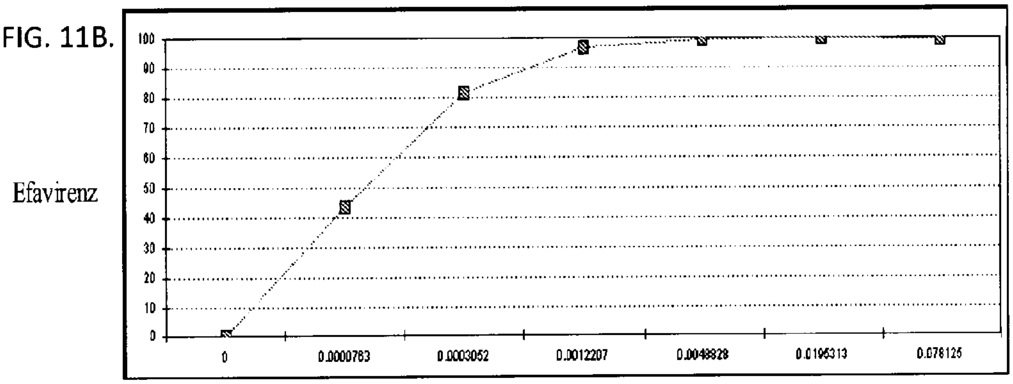
Figure 11C:
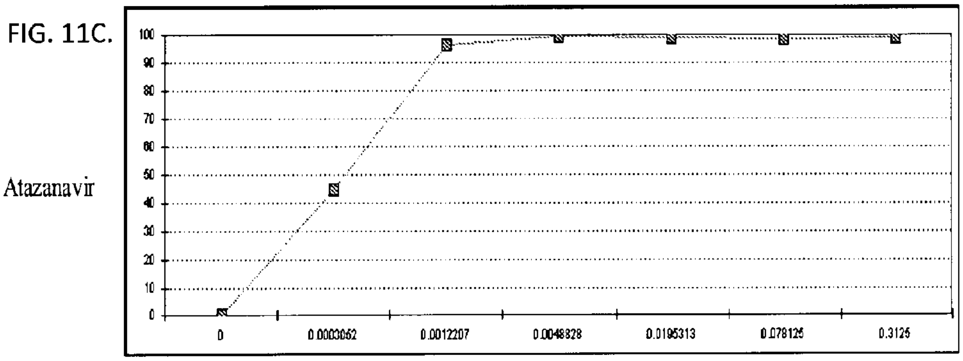
Figure 11D:
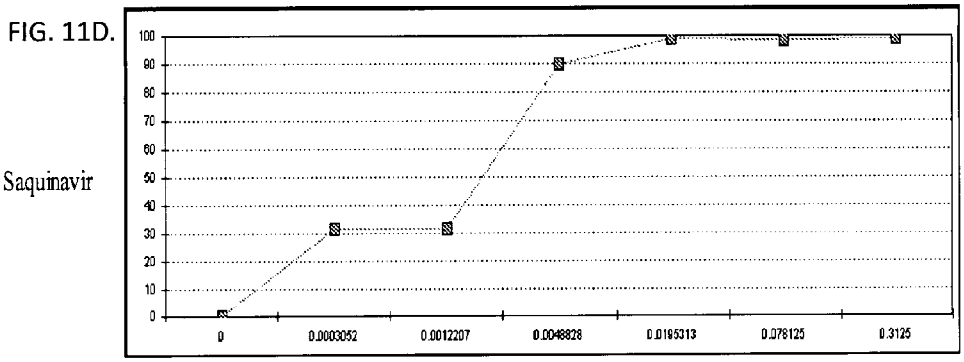
Figure 11E:
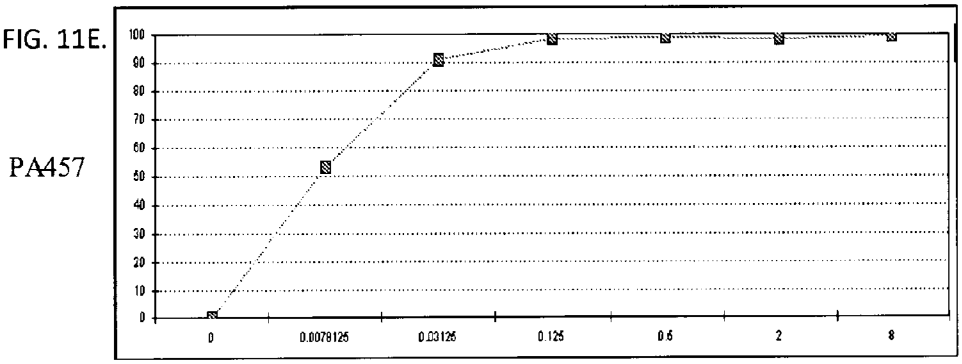
Figure 11F:
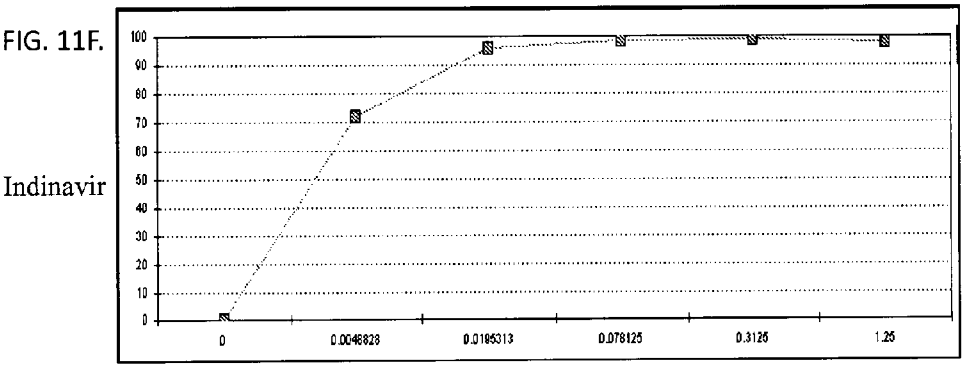
Figure 11G:
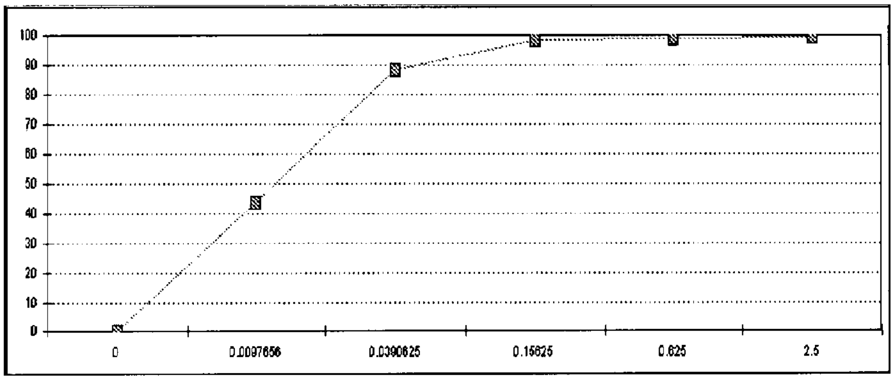
Figure 11H:
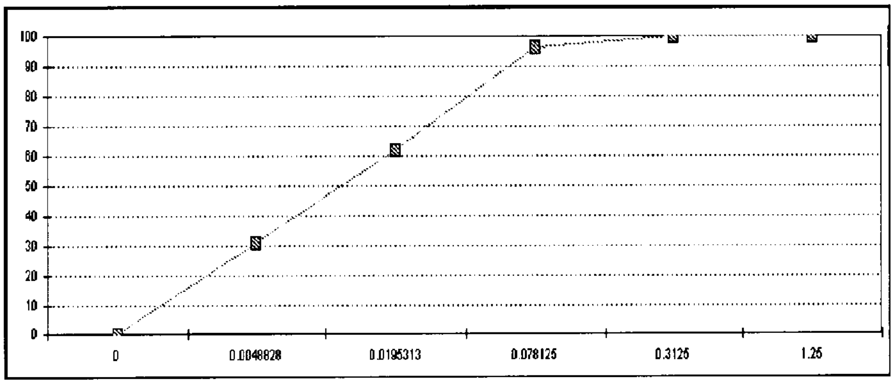
Figure 11I:
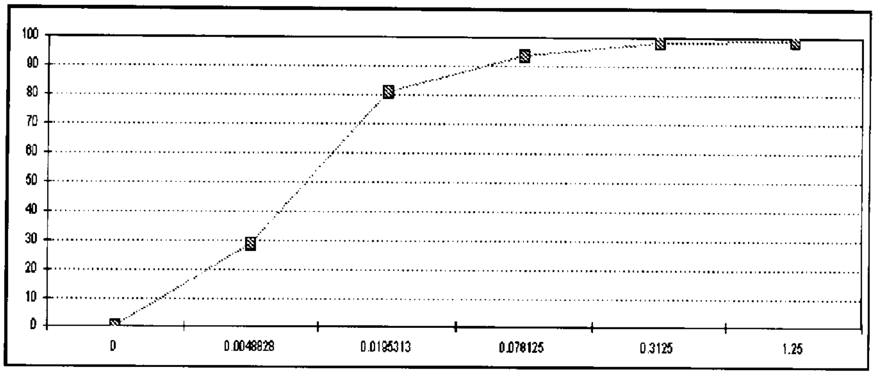
Figure 11J:
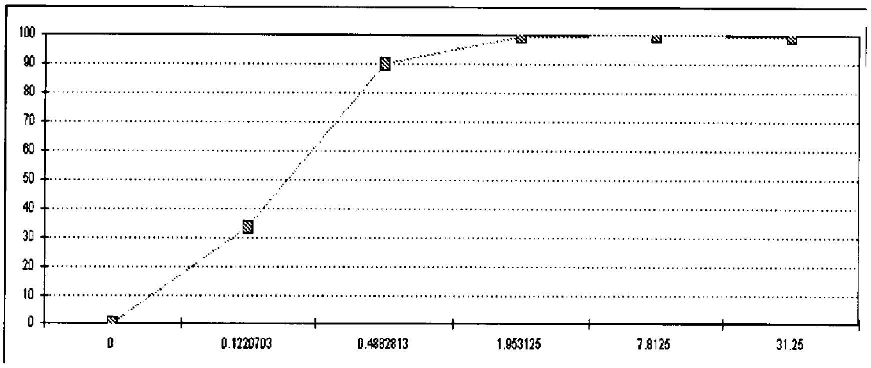
Figure 11K:
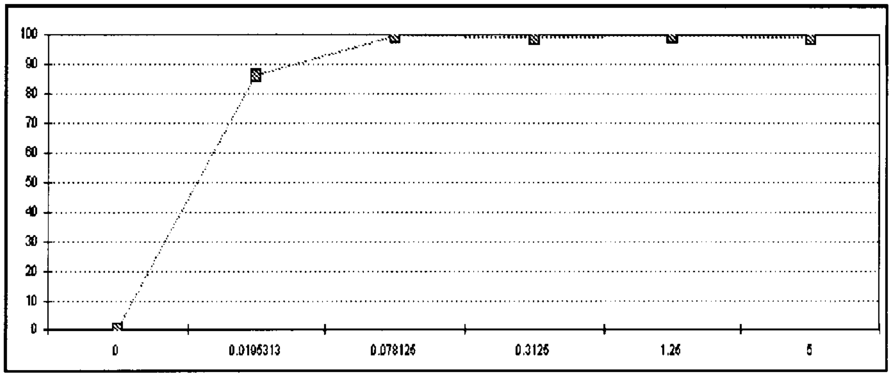
Figure 11L:
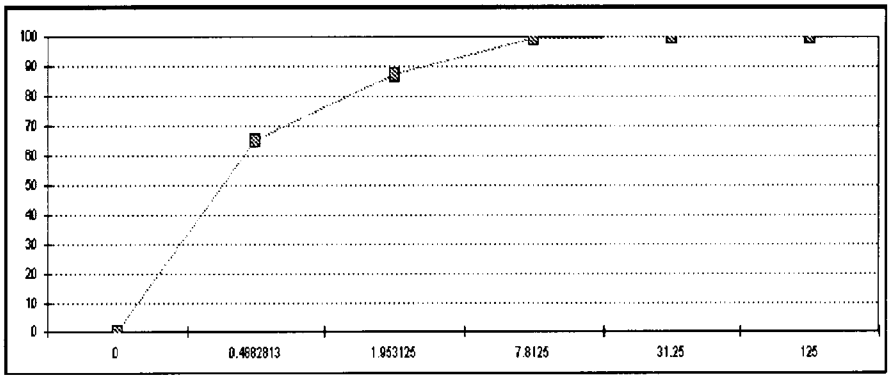
Figure 11M:
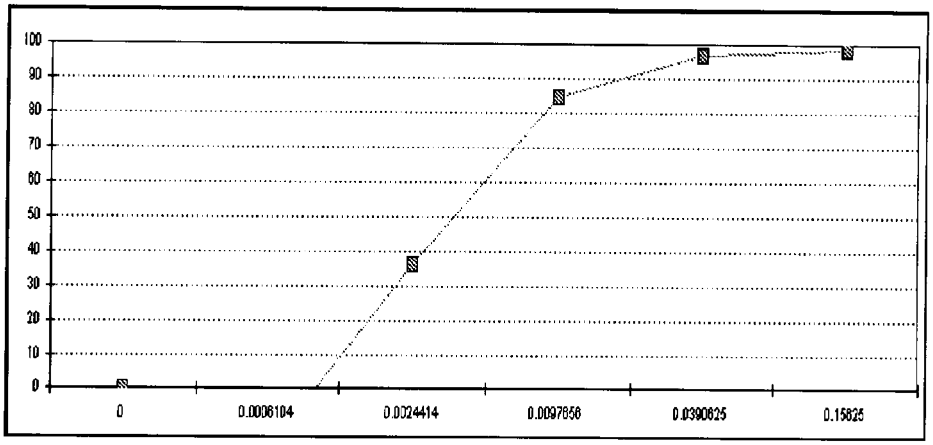
Figure 11N:
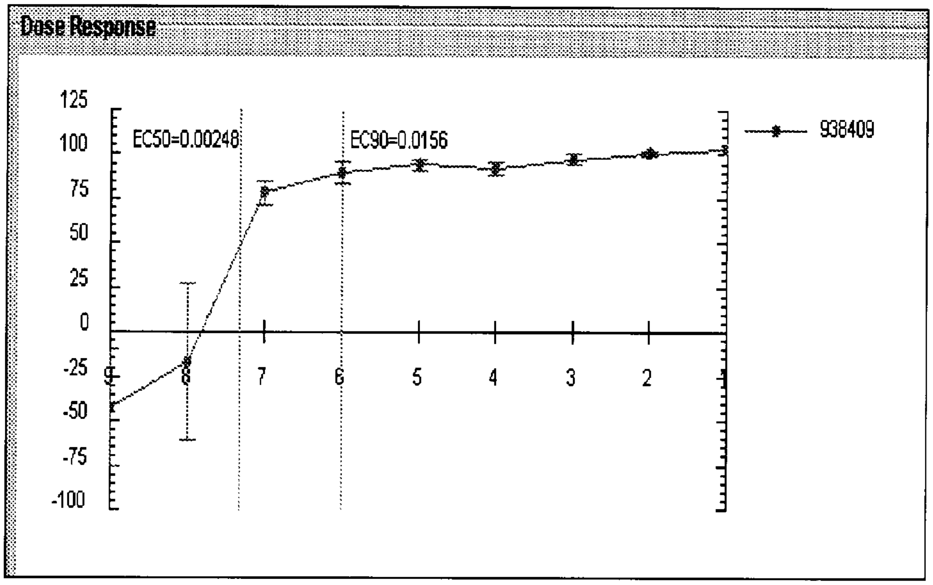
Figure 11O:
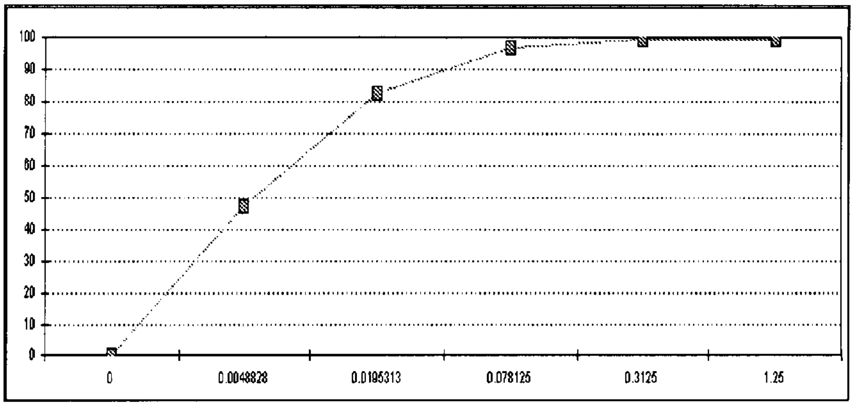
Figure 11P:
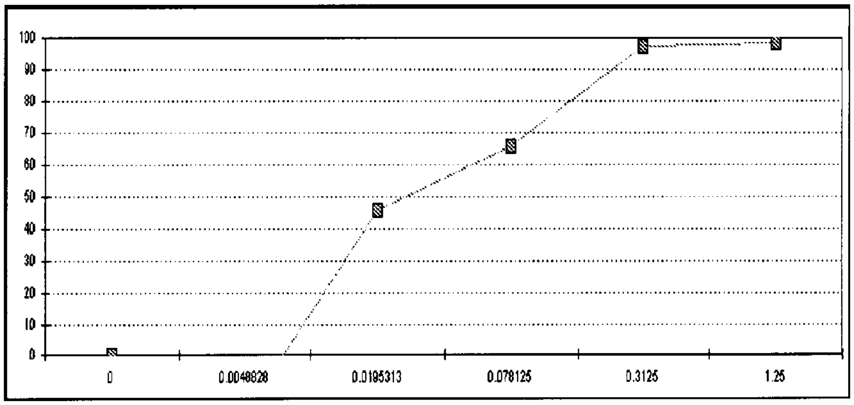
Figure 11Q:
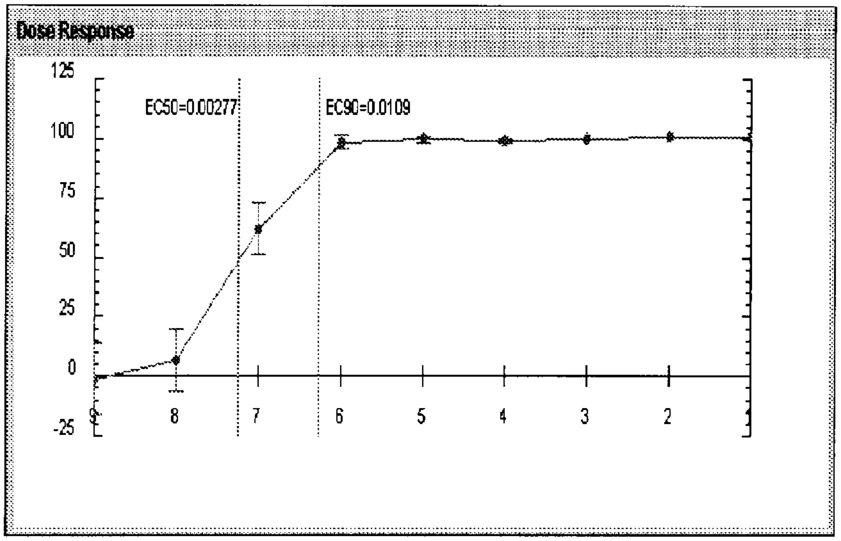
Figure 11R:
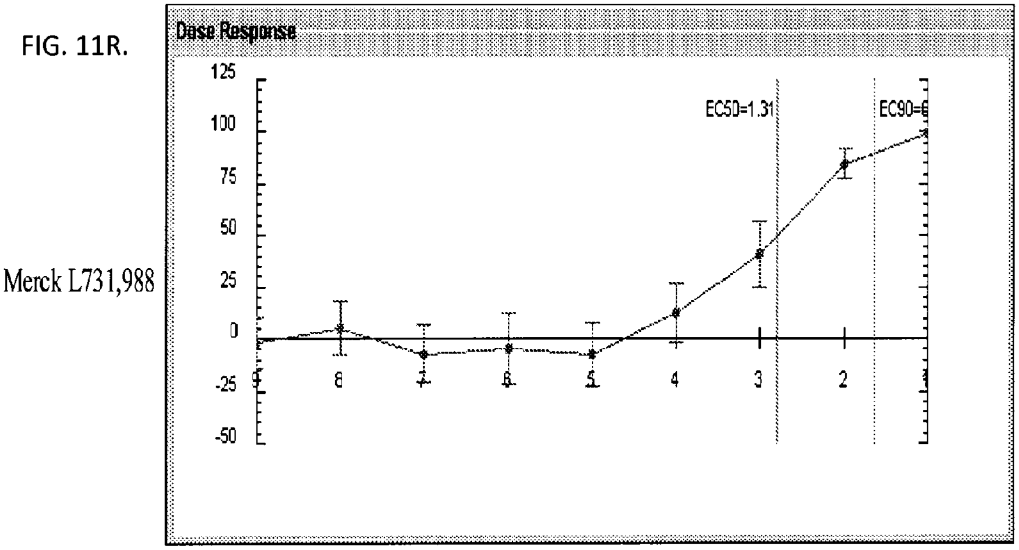

All recombinant clones (with a maximum of five per sample) were grown overnight in LB-ampicillin at 30° C. to prepare DNA from (27 in total). Miniprep DNA was prepared using the Qiaprep Spin miniprep (Qiagen) and checked by HindIII restriction digest. By comparison of the HindIII digestion pattern of the clones with that of the deletion backbones and that of the full-length parental HXB2D_eGFP vector, all 27 clones contained full-length HIV genomes. All 27 clones were transfected to MT4 cells using the Amaxa nucleofection technique and evaluated for their cythopathic effect (CPE). In total, 18 clones reached full CPE (cytopathogenic effect) during the time of evaluation (11 days) and were used for further infection experiments: 16 clones generated full CPE after 4 days, 1 clone after 5 days and 1 clone after 11 days. The other 9 clones did not show substantial infection after 11 days and were stopped for further analysis. The 18 harvested RVS (recombinant virus stock) were titrated and subjected to an antiviral experiment (AVE) at a standardized MOI (multiplicity of infection) using FDA-approved protease and RT inhibitors, and experimental maturation (PA-457) and integrase (GS-9137, L870,810 and L731,988) inhibitors. After 3 days of infection, GFP (green fluorescent protein) infection signals were quantified and dose-response curves were calculated. Only 1 out of 18 samples did not generate significant GFP expression above background, all other 17 RVS were successfully phenotyped for all drugs tested. As an example, FIG. 11 shows the dose-response curves 1 GAG-POL RVS for all drugs tested.

TABLE 11

Primer sequences of the primers used for the colony PCR and their position on the HXB2 reference.

| primer name | primer sequence from 5' to 3' | Position on HXB2 |
|---|---|---|
| SEQ ID NO 45: HXB2_5LTR_F_422 | CTG CAT ATA AGC AGC TGC TTT TTG | 422-445 |
| SEQ ID NO 46: GAG_R_895 | TCT AGC TCC CTG CTT GCC CA | 895-914 |
| SEQ ID NO 47: IN_F_5052 | ATG GCA GGT GAT GAT TGT GTG G | 5052-5073 |
| SEQ ID NO 48: HXB2_VIF_R_5247 | TTC TCC TGT ATG CAG ACC CCA A | 5247-5268 |

The invention claimed is:

1. An in vitro method for designing a drug regimen for an HIV-infected patient by determining the phenotypic susceptibility of HIV to at least one drug, comprising:

i) using at least one sample comprising HIV RNA from a patient, wherein the sample comprises the complete HIV gag-pol coding region;

ii) reverse-transcribing the HIV RNA and amplifying the resulting reverse transcript with primers specific for the complete HIV gag-pol coding region to obtain at least one amplicon comprising the complete HIV gag-pol coding region;

iii) obtaining a plasmid having the sequence of SEQ ID NO: 49;

iv) preparing at least one recombinant virus by recombination or ligation between at least one amplicon obtained in step ii) and the plasmid obtained in step iii); and v) monitoring at least one recombinant virus in the presence of at least one drug to determine the phenotypic susceptibility of said recombinant virus to at least one drug, wherein said susceptibility is determined by the cytopathogenicity of said recombinant virus to cells or by determining the replicative capacity of said recombinant virus in the presence of at least one drug.

* * * * *

SEQUENCE LISTING

<160> NUMBER OF SEQ ID NOS: 58

<210> SEQ ID NO 1
<211> LENGTH: 22
<212> TYPE: DNA
<213> ORGANISM: Artificial
<220> FEATURE:
<223> OTHER INFORMATION: Linear HIV-1 nucleic acid/primers

<400> SEQUENCE: 1
tggaaaatct ctagcagtgg cg 22

<210> SEQ ID NO 2
<211> LENGTH: 22
<212> TYPE: DNA
<213> ORGANISM: Artificial
<220> FEATURE:
<223> OTHER INFORMATION: Linear HIV-1 nucleic acid/primers

<400> SEQUENCE: 2
agtgggatgt gtacttctga ac 22

<210> SEQ ID NO 3
<211> LENGTH: 23
<212> TYPE: DNA
<213> ORGANISM: Artificial
<220> FEATURE:
<223> OTHER INFORMATION: Linear HIV-1 nucleic acid/primers

<400> SEQUENCE: 3
tctctagcag tggcgcccga aca 23

<210> SEQ ID NO 4
<211> LENGTH: 21
<212> TYPE: DNA
<213> ORGANISM: Artificial
<220> FEATURE:
<223> OTHER INFORMATION: Linear HIV-1 nucleic acid/primers

<400> SEQUENCE: 4
gggatgtgta cttctgaact t 21

<210> SEQ ID NO 5
<211> LENGTH: 26
<212> TYPE: DNA
<213> ORGANISM: Artificial
<220> FEATURE:
<223> OTHER INFORMATION: Linear HIV-1 nucleic acid/primers

<400> SEQUENCE: 5
ccctcaaatc actctttggc aacgac 26

<210> SEQ ID NO 6
<211> LENGTH: 24
<212> TYPE: DNA
<213> ORGANISM: Artificial
<220> FEATURE:
<223> OTHER INFORMATION: Linear HIV-1 nucleic acid/primers

<400> SEQUENCE: 6
ctcctgtatg cagaccccaa tatg 24

<210> SEQ ID NO 7
<211> LENGTH: 25
<212> TYPE: DNA

<213> ORGANISM: Artificial
<220> FEATURE:
<223> OTHER INFORMATION: Linear HIV-1 nucleic acid/primers

<400> SEQUENCE: 7
gctctattag atacaggagc agatg 25

<210> SEQ ID NO 8
<211> LENGTH: 22
<212> TYPE: DNA
<213> ORGANISM: Artificial
<220> FEATURE:
<223> OTHER INFORMATION: Linear HIV-1 nucleic acid/primers

<400> SEQUENCE: 8
caagtagtgt gtgcccgtct gt 22

<210> SEQ ID NO 9
<211> LENGTH: 25
<212> TYPE: DNA
<213> ORGANISM: Artificial
<220> FEATURE:
<223> OTHER INFORMATION: Linear HIV-1 nucleic acid/primers

<400> SEQUENCE: 9
ccattgttta acttttgggc catcc 25

<210> SEQ ID NO 10
<211> LENGTH: 25
<212> TYPE: DNA
<213> ORGANISM: Artificial
<220> FEATURE:
<223> OTHER INFORMATION: Linear HIV-1 nucleic acid/primers

<400> SEQUENCE: 10
ccattcctgg ctttaatttt actgg 25

<210> SEQ ID NO 11
<211> LENGTH: 19
<212> TYPE: DNA
<213> ORGANISM: Artificial
<220> FEATURE:
<223> OTHER INFORMATION: Linear HIV-1 nucleic acid/primers

<400> SEQUENCE: 11
agcagtggcg cccgaacag 19

<210> SEQ ID NO 12
<211> LENGTH: 23
<212> TYPE: DNA
<213> ORGANISM: Artificial
<220> FEATURE:
<223> OTHER INFORMATION: Linear HIV-1 nucleic acid/primers

<400> SEQUENCE: 12
tttgactagc gggaggctag aag 23

<210> SEQ ID NO 13
<211> LENGTH: 19
<212> TYPE: DNA
<213> ORGANISM: Artificial
<220> FEATURE:
<223> OTHER INFORMATION: Linear HIV-1 nucleic acid/primers

<400> SEQUENCE: 13
taaaagacac caaggaagc 19

-continued

<210> SEQ ID NO 14
<211> LENGTH: 16
<212> TYPE: DNA
<213> ORGANISM: Artificial
<220> FEATURE:
<223> OTHER INFORMATION: Linear HIV-1 nucleic acid/primers

<400> SEQUENCE: 14
aagacaccaa ggaagc 16

<210> SEQ ID NO 15
<211> LENGTH: 20
<212> TYPE: DNA
<213> ORGANISM: Artificial
<220> FEATURE:
<223> OTHER INFORMATION: Linear HIV-1 nucleic acid/primers

<400> SEQUENCE: 15
catagcagga actactagta 20

<210> SEQ ID NO 16
<211> LENGTH: 24
<212> TYPE: DNA
<213> ORGANISM: Artificial
<220> FEATURE:
<223> OTHER INFORMATION: Linear HIV-1 nucleic acid/primers

<400> SEQUENCE: 16
taaaatagta agaatgtata gccc 24

<210> SEQ ID NO 17
<211> LENGTH: 20
<212> TYPE: DNA
<213> ORGANISM: Artificial
<220> FEATURE:
<223> OTHER INFORMATION: Linear HIV-1 nucleic acid/primers

<400> SEQUENCE: 17
atgacagcat gtcagggagt 20

<210> SEQ ID NO 18
<211> LENGTH: 19
<212> TYPE: DNA
<213> ORGANISM: Artificial
<220> FEATURE:
<223> OTHER INFORMATION: Linear HIV-1 nucleic acid/primers

<400> SEQUENCE: 18
gagagcttca ggtttgggg 19

<210> SEQ ID NO 19
<211> LENGTH: 19
<212> TYPE: DNA
<213> ORGANISM: Artificial
<220> FEATURE:
<223> OTHER INFORMATION: Linear HIV-1 nucleic acid/primers

<400> SEQUENCE: 19
cactctttgg caacgaccc 19

<210> SEQ ID NO 20
<211> LENGTH: 20
<212> TYPE: DNA
<213> ORGANISM: Artificial
<220> FEATURE:
<223> OTHER INFORMATION: Linear HIV-1 nucleic acid/primers -continued

<400> SEQUENCE: 20
tggaaaccaa aaatgatagg 20

<210> SEQ ID NO 21
<211> LENGTH: 18
<212> TYPE: DNA
<213> ORGANISM: Artificial
<220> FEATURE:
<223> OTHER INFORMATION: Linear HIV-1 nucleic acid/primers

<400> SEQUENCE: 21
aattgggcct gaaaatcc 18

<210> SEQ ID NO 22
<211> LENGTH: 20
<212> TYPE: DNA
<213> ORGANISM: Artificial
<220> FEATURE:
<223> OTHER INFORMATION: Linear HIV-1 nucleic acid/primers

<400> SEQUENCE: 22
cctccattcc tttggatggg 20

<210> SEQ ID NO 23
<211> LENGTH: 19
<212> TYPE: DNA
<213> ORGANISM: Artificial
<220> FEATURE:
<223> OTHER INFORMATION: Linear HIV-1 nucleic acid/primers

<400> SEQUENCE: 23
gaaagcatag taatatggg 19

<210> SEQ ID NO 24
<211> LENGTH: 22
<212> TYPE: DNA
<213> ORGANISM: Artificial
<220> FEATURE:
<223> OTHER INFORMATION: Linear HIV-1 nucleic acid/primers

<400> SEQUENCE: 24
caaccagata aaagtgaatc ag 22

<210> SEQ ID NO 25
<211> LENGTH: 19
<212> TYPE: DNA
<213> ORGANISM: Artificial
<220> FEATURE:
<223> OTHER INFORMATION: Linear HIV-1 nucleic acid/primers

<400> SEQUENCE: 25
tagcaggaag atggccagt 19

<210> SEQ ID NO 26
<211> LENGTH: 21
<212> TYPE: DNA
<213> ORGANISM: Artificial
<220> FEATURE:
<223> OTHER INFORMATION: Linear HIV-1 nucleic acid/primers

<400> SEQUENCE: 26
gtagacataa tagcaacaga c 21

<210> SEQ ID NO 27
<211> LENGTH: 20
<212> TYPE: DNA

<213> ORGANISM: Artificial
<220> FEATURE:
<223> OTHER INFORMATION: Linear HIV-1 nucleic acid/primers

<400> SEQUENCE: 27
tcttgtgggg tggctccttc 20

<210> SEQ ID NO 28
<211> LENGTH: 22
<212> TYPE: DNA
<213> ORGANISM: Artificial
<220> FEATURE:
<223> OTHER INFORMATION: Linear HIV-1 nucleic acid/primers

<400> SEQUENCE: 28
tcttgtgggg tggctccttc tg 22

<210> SEQ ID NO 29
<211> LENGTH: 20
<212> TYPE: DNA
<213> ORGANISM: Artificial
<220> FEATURE:
<223> OTHER INFORMATION: Linear HIV-1 nucleic acid/primers

<400> SEQUENCE: 29
tctacatagt ctctaaaggg 20

<210> SEQ ID NO 30
<211> LENGTH: 23
<212> TYPE: DNA
<213> ORGANISM: Artificial
<220> FEATURE:
<223> OTHER INFORMATION: Linear HIV-1 nucleic acid/primers

<400> SEQUENCE: 30
actccctgac atgctgtcat cat 23

<210> SEQ ID NO 31
<211> LENGTH: 20
<212> TYPE: DNA
<213> ORGANISM: Artificial
<220> FEATURE:
<223> OTHER INFORMATION: Linear HIV-1 nucleic acid/primers

<400> SEQUENCE: 31
gtggggctgt tggctctggt 20

<210> SEQ ID NO 32
<211> LENGTH: 20
<212> TYPE: DNA
<213> ORGANISM: Artificial
<220> FEATURE:
<223> OTHER INFORMATION: Linear HIV-1 nucleic acid/primers

<400> SEQUENCE: 32
attcccccta tcatttttgg 20

<210> SEQ ID NO 33
<211> LENGTH: 18
<212> TYPE: DNA
<213> ORGANISM: Artificial
<220> FEATURE:
<223> OTHER INFORMATION: Linear HIV-1 nucleic acid/primers

<400> SEQUENCE: 33
gataaaacct ccaattcc 18

-continued

<210> SEQ ID NO 34
<211> LENGTH: 21
<212> TYPE: DNA
<213> ORGANISM: Artificial
<220> FEATURE:
<223> OTHER INFORMATION: Linear HIV-1 nucleic acid/primers

<400> SEQUENCE: 34
cttcccagaa gtcttgagtt c 21

<210> SEQ ID NO 35
<211> LENGTH: 19
<212> TYPE: DNA
<213> ORGANISM: Artificial
<220> FEATURE:
<223> OTHER INFORMATION: Linear HIV-1 nucleic acid/primers

<400> SEQUENCE: 35
ggaatattgc tggtgatcc 19

<210> SEQ ID NO 36
<211> LENGTH: 19
<212> TYPE: DNA
<213> ORGANISM: Artificial
<220> FEATURE:
<223> OTHER INFORMATION: Linear HIV-1 nucleic acid/primers

<400> SEQUENCE: 36
tgtatgtcat tgacagtcc 19

<210> SEQ ID NO 37
<211> LENGTH: 20
<212> TYPE: DNA
<213> ORGANISM: Artificial
<220> FEATURE:
<223> OTHER INFORMATION: Linear HIV-1 nucleic acid/primers

<400> SEQUENCE: 37
gggtcataat acactccatg 20

<210> SEQ ID NO 38
<211> LENGTH: 17
<212> TYPE: DNA
<213> ORGANISM: Artificial
<220> FEATURE:
<223> OTHER INFORMATION: Linear HIV-1 nucleic acid/primers

<400> SEQUENCE: 38
ctcccactca ggaatcc 17

<210> SEQ ID NO 39
<211> LENGTH: 18
<212> TYPE: DNA
<213> ORGANISM: Artificial
<220> FEATURE:
<223> OTHER INFORMATION: Linear HIV-1 nucleic acid/primers

<400> SEQUENCE: 39
cagtcttctg atttgttg 18

<210> SEQ ID NO 40
<211> LENGTH: 21
<212> TYPE: DNA
<213> ORGANISM: Artificial
<220> FEATURE:
<223> OTHER INFORMATION: Linear HIV-1 nucleic acid/primers -continued

<400> SEQUENCE: 40
ctttgtgtgc tggtacccat g 21

<210> SEQ ID NO 41
<211> LENGTH: 24
<212> TYPE: DNA
<213> ORGANISM: Artificial
<220> FEATURE:
<223> OTHER INFORMATION: Linear HIV-1 nucleic acid/primers

<400> SEQUENCE: 41
ggactacagt ctacttgtcc aatg 24

<210> SEQ ID NO 42
<211> LENGTH: 20
<212> TYPE: DNA
<213> ORGANISM: Artificial
<220> FEATURE:
<223> OTHER INFORMATION: Linear HIV-1 nucleic acid/primers

<400> SEQUENCE: 42
ctgccatttg tactgctgtc 20

<210> SEQ ID NO 43
<211> LENGTH: 22
<212> TYPE: DNA
<213> ORGANISM: Artificial
<220> FEATURE:
<223> OTHER INFORMATION: Linear HIV-1 nucleic acid/primers

<400> SEQUENCE: 43
atcacctgcc atctgttttc ca 22

<210> SEQ ID NO 44
<211> LENGTH: 18
<212> TYPE: DNA
<213> ORGANISM: Artificial
<220> FEATURE:
<223> OTHER INFORMATION: Linear HIV-1 nucleic acid/primers

<400> SEQUENCE: 44
atgtgtactt ctgaactt 18

<210> SEQ ID NO 45
<211> LENGTH: 24
<212> TYPE: DNA
<213> ORGANISM: Artificial
<220> FEATURE:
<223> OTHER INFORMATION: Linear HIV-1 nucleic acid/primers

<400> SEQUENCE: 45
ctgcatataa gcagctgctt tttg 24

<210> SEQ ID NO 46
<211> LENGTH: 20
<212> TYPE: DNA
<213> ORGANISM: Artificial
<220> FEATURE:
<223> OTHER INFORMATION: Linear HIV-1 nucleic acid/primers

<400> SEQUENCE: 46
tctagctccc tgcttgccca 20

<210> SEQ ID NO 47
<211> LENGTH: 22
<212> TYPE: DNA

<213> ORGANISM: Artificial
<220> FEATURE:
<223> OTHER INFORMATION: Linear HIV-1 nucleic acid/primers

<400> SEQUENCE: 47
atggcaggtg atgattgtgt gg 22

<210> SEQ ID NO 48
<211> LENGTH: 22
<212> TYPE: DNA
<213> ORGANISM: Artificial
<220> FEATURE:
<223> OTHER INFORMATION: Linear HIV-1 nucleic acid/primers

<400> SEQUENCE: 48
ttctcctgta tgcagacccc aa 22

<210> SEQ ID NO 49
<211> LENGTH: 10992
<212> TYPE: DNA
<213> ORGANISM: Artificial
<220> FEATURE:
<223> OTHER INFORMATION: Circular HIV-1 nucleic acid

<400> SEQUENCE: 49
tggaagggct aattcactcc caaagaagac aagatatcct tgatctgtgg atctaccaca 60
cacaaggcta cttccctgat tagcagaact acacaccagg gccagggtca gatatccact 120
gacctttgga tggtgctaca agctagtacc agttgagcca gataaggtag aagaggccaa 180
taaaggagag aacaccagct tgttacaccc tgtgagcctg catgggatgg atgacccgga 240
gagagaagtg ttagagtgga ggtttgacag ccgcctagca tttcatcacg tggcccgaga 300
gctgcatccg gagtacttca agaactgctg atatcgagct tgctacaagg gactttccgc 360
tggggacttt ccagggaggc gtggcctggg cgggactggg gagtggcgag ccctcagatc 420
ctgcatataa gcagctgctt tttgcctgta ctgggtctct ctggttagac cagatctgag 480
cctgggagct ctctggctaa ctagggaacc cactgcttaa gcctcaataa agcttgcctt 540
gagtgcttca agtagtgtgt gcccgtctgt tgtgtgactc tggtaactag agatccctca 600
gaccctttta gtcagtgtgg aaaatctcta gcagtggcgt taattaaccg tacgcgtact 660
acgtaagaag tacacatccc actaggggat gctagattgg taataacaac atattggggt 720
ctgcatacag gagaaagaga ctggcatttg ggtcagggag tctccataga atggaggaaa 780
aagagatata gcacacaagt agaccctgaa ctagcagacc aactaattca tctgtattac 840
tttgactgtt tttcagactc tgctataaga aaggccttat taggacacat agttagccct 900
aggtgtgaat atcaagcagg acataacaag gtaggatctc tacaatactt ggcactagca 960
gcattaataa caccaaaaaa gataaagcca cctttgccta gtgttacgaa actgacagag 1020
gatagatgga acaagcccca gaagaccaag ggccacagag ggagccacac aatgaatgga 1080
cactagagct tttagaggag cttaagaatg aagctgttag acattttcct aggatttggc 1140
tccatggctt agggcaacat atctatgaaa cttatgggga tacttgggca ggagtggaag 1200
ccataataag aattctgcaa caactgctgt ttatccattt tcagaattgg gtgtcgacat 1260
agcagaatag gcgttactcg acagaggaga gcaagaaatg gagccagtag atcctagact 1320
agagccctgg aagcatccag gaagtcagcc taaaactgct tgtaccaatt gctattgtaa 1380
aaagtgttgc tttcattgcc aagtttgttt cataacaaaa gccttaggca tctcctatgg 1440
caggaagaag cggagacagc gacgaagagc tcatcagaac agtcagactc atcaagcttc 1500

-continued

```
tctatcaaag cagtaagtag tacatgtaac gcaacctata ccaatagtag caatagtagc   1560
attagtagta gcaataataa tagcaatagt tgtgtggtcc atagtaatca tagaatatag   1620
gaaaatatta agacaaagaa aaatagacag gttaattgat agactaatag aaagagcaga   1680
agacagtggc aatgagagtg aaggagaaat atcagcactt gtggagatgg gggtggagat   1740
ggggcaccat gctccttggg atgttgatga tctgtagtgc tacagaaaaa ttgtgggtca   1800
cagtctatta tggggtacct gtgtggaagg aagcaaccac cactctattt tgtgcatcag   1860
atgctaaagc atatgataca gaggtacata atgtttgggc cacacatgcc tgtgtaccca   1920
cagaccccaa cccacaagaa gtagtattgg taaatgtgac agaaaatttt aacatgtgga   1980
aaaatgacat ggtagaacag atgcatgagg atataatcag tttatgggat caaagcctaa   2040
agccatgtgt aaaattaacc ccactctgtg ttagtttaaa gtgcactgat ttgaagaatg   2100
atactaatac caatagtagt agcgggagaa tgataatgga gaaaggagag ataaaaaact   2160
gctctttcaa tatcagcaca agcataagag gtaaggtgca gaaagaatat gcattttttt   2220
ataaacttga tataatacca atagataatg atactaccag ctataagttg acaagttgta   2280
acacctcagt cattacacag gcctgtccaa aggtatcctt tgagccaatt cccatacatt   2340
attgtgcccc ggctggtttt gcgattctaa aatgtaataa taagacgttc aatggaacag   2400
gaccatgtac aaatgtcagc acagtacaat gtacacatgg aattaggcca gtagtatcaa   2460
ctcaactgct gttaaatggc agtctagcag aagaagaggt agtaattaga tctgtcaatt   2520
tcacggacaa tgctaaaacc ataatagtac agctgaacac atctgtagaa attaattgta   2580
caagacccaa caacaataca agaaaaagaa tccgtatcca gagaggacca gggagagcat   2640
ttgttacaat aggaaaaata ggaaatatga gacaagcaca ttgtaacatt agtagagcaa   2700
aatggaataa cactttaaaa cagatagcta gcaaattaag agaacaattt ggaaataata   2760
aaacaataat ctttaagcaa tcctcaggag gggacccaga aattgtaacg cacagtttta   2820
attgtggagg ggaatttttc tactgtaatt caacacaact gtttaatagt acttggttta   2880
atagtacttg gagtactgaa gggtcaaata acactgaagg aagtgacaca atcaccctcc   2940
catgcagaat aaaacaaatt ataaacatgt ggcagaaagt aggaaaagca atgtatgccc   3000
ctcccatcag tggacaaatt agatgttcat caaatattac agggctgcta ttaacaagag   3060
atggtggtaa tagcaacaat gagtccgaga tcttcagacc tggaggagga gatatgaggg   3120
acaattggag aagtgaatta tataaatata aagtagtaaa aattgaacca ttaggagtag   3180
cacccaccaa ggcaaagaga agagtggtgc agagagaaaa aagagcagtg ggaataggag   3240
ctttgttcct tgggttcttg ggagcagcag gaagcactat gggcgcagcg tcaatgacgc   3300
tgacggtaca ggccagacaa ttattgtctg gtatagtgca gcagcagaac aatttgctga   3360
gggctattga ggcgcaacag catctgttgc aactcacagt ctggggcatc aagcagctcc   3420
aggcaagaat cctggctgtg gaaagatacc taaaggatca acagctcctg gggatttggg   3480
gttgctctgg aaaactcatt tgcaccactg ctgtgccttg gaatgctagt tggagtaata   3540
aatctctgga acagatttgg aatcacacga cctggatgga gtgggacaga gaaattaaca   3600
attacacaag cttaatacac tccttaattg aagaatcgca aaaccagcaa gaaaagaatg   3660
aacaagaatt attggaatta gataaatggg caagtttgtg gaattggttt aacataacaa   3720
attggctgtg gtatataaaa ttattcataa tgatagtagg aggcttggta ggtttaagaa   3780
tagtttttgc tgtactttct atagtgaata gagttaggca gggatattca ccattatcgt   3840
ttcagaccca cctcccaacc ccgaggggac ccgacaggcc cgaaggaata gaagaagaag   3900
```

-continued

```
gtggagagag agacagagac agatccattc gattagtgaa cggatcctta gcacttatct   3960
gggacgatct gcggagcctg tgcctcttca gctaccaccg cttgagagac ttactcttga   4020
ttgtaacgag gattgtggaa cttctgggac gcagggggtg ggaagccctc aaatattggt   4080
ggaatctcct acaatattgg agtcaggagc taaagaatag tgctgttagc ttgctcaatg   4140
ccacagccat agcagtagct gaggggacag atagggttat agaagtagta caaggagctt   4200
gtagagctat tcgccacata cctagaagaa taagacaggg cttggaaagg attttgctat   4260
aagatgggtg gcgcggccgc aatggtgagc aagggcgagg agctgttcac cggggtggtg   4320
cccatcctgg tcgagctgga cggcgacgta aacggccaca agttcagcgt gtccggcgag   4380
ggcgagggcg atgccaccta cggcaagctg accctgaagt tcatctgcac caccggcaag   4440
ctgcccgtgc cctggcccac cctcgtgacc accctgacct acggcgtgca gtgcttcagc   4500
cgctaccccg accacatgaa gcagcacgac ttcttcaagt ccgccatgcc cgaaggctac   4560
gtccaggagc gcaccatctt cttcaaggac gacggcaact acaagacccg cgccgaggtg   4620
aagttcgagg gcgacaccct ggtgaaccgc atcgagctga agggcatcga cttcaaggag   4680
gacggcaaca tcctggggca caagctggag tacaactaca acagccacaa cgtctatatc   4740
atggccgaca agcagaagaa cggcatcaag gcgaacttca agatccgcca caacatcgag   4800
gacggcagcg tgcagctcgc cgaccactac cagcagaaca cccccatcgg cgacggcccc   4860
gtgctgctgc ccgacaacca ctacctgagc acccagtccg ccctgagcaa agaccccaac   4920
gagaagcgcg atcacatggt cctgctggag ttcgtgaccg ccgccgggat cactctcggc   4980
atggacgagc tgtacaagta agaattctga ctcgagacct agaaaaacat ggagcaatca   5040
caagtagcaa tacagcagct accaatgctg attgtgcctg gctagaagca caagaggagg   5100
aggaggtggg ttttccagtc acacctcagg tacctttaag accaatgact tacaaggcag   5160
ctgtagatct tagccacttt ttaaaagaaa aggggggact ggaagggcta attcactccc   5220
aacgaagaca agatatcctt gatctgtgga tctaccacac acaaggctac ttccctgatt   5280
ggcagaacta cacaccaggg ccagggatca gatatccact gacctttgga tggtgctaca   5340
agctagtacc agttgagcaa gagaaggtag aagaagccaa tgaaggagag aacacccgct   5400
tgttacaccc tgtgagcctg catgggatgg atgacccgga gagagaagta ttagagtgga   5460
ggtttgacag ccgcctagca tttcatcaca tggcccgaga gctgcatccg gagtacttca   5520
agaactgctg acatcgagct tgctacaagg gactttccgc tggggacttt ccagggaggc   5580
gtggcctggg cgggactggg gagtggcgag ccctcagatg ctgcatataa gcagctgctt   5640
tttgcttgta ctgggtctct ctggttagac cagatctgag cctgggagct ctctggctaa   5700
ctagggaacc cactgcttaa gcctcaataa agcttgcctt gagtgcttca agtagtgtgt   5760
gcccgtctgt tgtgtgactc tggcgcgcct ctagaattaa ttccgtgtat tctatagtgt   5820
cacctaaatc gtatgtgtat gatacataag gttatgtatt aattgtagcc gcgttctaac   5880
gacaatatgt acaagcctaa ttgtgtagca tctggcttac tgaagcagac cctatcatct   5940
ctctcgtaaa ctgccgtcag agtcggtttg gttggacgaa ccttctgagt ttctggtaac   6000
gccgtcccgc acccggaaat ggtcagcgaa ccaatcagca gggtcatcgc tagccagatc   6060
ctctacgccg gacgcatcgt ggccggcatc accggcgcca caggtgcggt tgctggcgcc   6120
tatatcgccg acatcaccga tggggaagat cgggctcgcc acttcgggct catgagcgct   6180
tgtttcggcg tgggtatggt ggcaggcccc gtggccgggg gactgttggg cgccatctcc   6240
ttgcatgcac cattccttgc ggcggcggtg ctcaacggcc tcaacctact actgggctgc   6300
```

-continued

```
ttcctaatgc aggagtcgca taagggagag cgtcgaatgg tgcactctca gtacaatctg   6360
ctctgatgcc gcatagttaa gccagccccg acacccgcca acacccgctg acgcgccctg   6420
acgggcttgt ctgctcccgg catccgctta cagacaagct gtgaccgtct ccgggagctg   6480
catgtgtcag aggttttcac cgtcatcacc gaaacgcgcg agacgaaagg gcctcgtgat   6540
acgcctattt ttataggtta atgtcatgat aataatggtt tcttagacgt caggtggcac   6600
ttttcgggga aatgtgcgcg gaacccctat ttgtttattt ttctaaatac attcaaatat   6660
gtatccgctc atgagacaat aaccctgata aatgcttcaa taatattgaa aaaggaagag   6720
tatgagtatt caacatttcc gtgtcgccct tattcccttt tttgcggcat tttgccttcc   6780
tgtttttgct cacccagaaa cgctggtgaa agtaaaagat gctgaagatc agttgggtgc   6840
acgagtgggt tacatcgaac tggatctcaa cagcggtaag atccttgaga gttttcgccc   6900
cgaagaacgt tttccaatga tgagcacttt taaagttctg ctatgtggcg cggtattatc   6960
ccgtattgac gccgggcaag agcaactcgg tcgccgcata cactattctc agaatgactt   7020
ggttgagtac tcaccagtca cagaaaagca tcttacggat ggcatgacag taagagaatt   7080
atgcagtgct gccataacca tgagtgataa cactgcggcc aacttacttc tgacaacgat   7140
cggaggaccg aaggagctaa ccgctttttt gcacaacatg ggggatcatg taactcgcct   7200
tgatcgttgg gaaccggagc tgaatgaagc cataccaaac gacgagcgtg acaccacgat   7260
gcctgtagca atggcaacaa cgttgcgcaa actattaact ggcgaactac ttactctagc   7320
ttcccggcaa caattaatag actggatgga ggcggataaa gttgcaggac cacttctgcg   7380
ctcggccctt ccggctggct ggtttattgc tgataaatct ggagccggtg agcgtgggtc   7440
tcgcggtatc attgcagcac tggggccaga tggtaagccc tcccgtatcg tagttatcta   7500
cacgacgggg agtcaggcaa ctatggatga acgaaataga cagatcgctg agataggtgc   7560
ctcactgatt aagcattggt aactgtcaga ccaagtttac tcatatatac tttagattga   7620
tttaaaactt catttttaat ttaaaaggat ctaggtgaag atcctttttg ataatctcat   7680
gaccaaaatc ccttaacgtg agttttcgtt ccactgagcg tcagaccccg tagaaaagat   7740
caaaggatct tcttgagatc cttttttttct gcgcgtaatc tgctgcttgc aaacaaaaaa   7800
accaccgcta ccagcggtgg tttgtttgcc ggatcaagag ctaccaactc tttttccgaa   7860
ggtaactggc ttcagcagag cgcagatacc aaatactgtt cttctagtgt agccgtagtt   7920
aggccaccac ttcaagaact ctgtagcacc gcctacatac ctcgctctgc taatcctgtt   7980
accagtggct gctgccagtg gcgataagtc gtgtcttacc gggttggact caagacgata   8040
gttaccggat aaggcgcagc ggtcgggctg aacggggggt tcgtgcacac agcccagctt   8100
ggagcgaacg acctacaccg aactgagata cctacagcgt gagctatgag aaagcgccac   8160
gcttcccgaa gggagaaagg cggacaggta tccggtaagc ggcagggtcg gaacaggaga   8220
gcgcacgagg gagcttccag ggggaaacgc ctggtatctt tatagtcctg tcgggtttcg   8280
ccacctctga cttgagcgtc gatttttgtg atgctcgtca ggggggcgga gcctatggaa   8340
aaacgccagc aacgcggcct ttttacggtt cctggccttt tgctggcctt ttgctcacat   8400
gttctttcct gcgttatccc ctgattctgt ggataaccgt attaccgcct ttgagtgagc   8460
tgataccgct cgccgcagcc gaacgaccga gcgcagcgag tcagtgagcg aggaagcgga   8520
agagcgccca atacgcaaac cgcctctccc cgcgcgttgg ccgattcatt aatgcagctg   8580
tggaatgtgt gtcagttagg gtgtggaaag tccccaggct ccccagcagg cagaagtatg   8640
caaagcatgc atctcaatta gtcagcaacc aggtgtggaa agtccccagg ctccccagca   8700
```

-continued

```
ggcagaagta tgcaaagcat gcatctcaat tagtcagcaa ccatagtccc gcccctaact   8760
ccgcccatcc cgcccctaac tccgcccagt tccgcccatt ctccgcccca tggctgacta   8820
attttttttta tttatgcaga ggccgaggcc gcctcggcct ctgagctatt ccagaagtag   8880
tgaggaggct tttttggagg cctaggcttt tgcaaaaagc ttggacacaa gacaggcttg   8940
cgagatatgt ttgagaatac cactttatcc cgcgtcaggg agaggcagtg cgtaaaaaga   9000
cgcggactca tgtgaaatac tggtttttag tgcgccagat ctctataatc tcgcgcaacc   9060
tattttcccc tcgaacactt tttaagccgt agataaacag gctgggacac ttcacatgag   9120
cgaaaaatac atcgtcacct gggacatgtt gcagatccat gcacgtaaac tcgcaagccg   9180
actgatgcct tctgaacaat ggaaaggcat tattgccgta agccgtggcg gtctggtacc   9240
gggtgcgtta ctggcgcgtg aactgggtat tcgtcatgtc gataccgttt gtatttccag   9300
ctacgatcac gacaaccagc gcgagcttaa agtgctgaaa cgcgcagaag gcgatggcga   9360
aggcttcatc gttattgatg acctggtgga taccggtggt actgcggttg cgattcgtga   9420
aatgtatcca aaagcgcact ttgtcaccat cttcgcaaaa ccggctggtc gtccgctggt   9480
tgatgactat gttgttgata tcccgcaaga tacctggatt gaacagccgt gggatatggg   9540
cgtcgtattc gtcccgccaa tctccggtcg ctaatctttt caacgcctgg cactgccggg   9600
cgttgttctt tttaacttca ggcgggttac aatagtttcc agtaagtatt ctggaggctg   9660
catccatgac acaggcaaac ctgagcgaaa ccctgttcaa accccgcttt aaacatcctg   9720
aaacctcgac gctagtccgc cgctttaatc acggcgcaca accgcctgtg cagtcggccc   9780
ttgatggtaa aaccatccct cactggtatc gcatgattaa ccgtctgatg tggatctggc   9840
gcggcattga cccacgcgaa atcctcgacg tccaggcacg tattgtgatg agcgatgccg   9900
aacgtaccga cgatgattta tacgatacgg tgattggcta ccgtggcggc aactggattt   9960
atgagtgggc cccggatctt tgtgaaggaa ccttacttct gtggtgtgac ataattggac  10020
aaactaccta cagagattta aagctctaag gtaaatataa aatttttaag tgtataatgt  10080
gttaaactac tgattctaat tgtttgtgta ttttagattc caacctatgg aactgatgaa  10140
tgggagcagt ggtggaatgc ctttaatgag gaaaacctgt tttgctcaga agaaatgcca  10200
tctagtgatg atgaggctac tgctgactct caacattcta ctcctccaaa aaagaagaga  10260
aaggtagaag accccaagga ctttccttca gaattgctaa gtttttttgag tcatgctgtg  10320
tttagtaata gaactcttgc ttgctttgct atttacacca caaaggaaaa agctgcactg  10380
ctatacaaga aaattatgga aaaatattct gtaaccttta taagtaggca taacagttat  10440
aatcataaca tactgttttt tcttactcca cacaggcata gagtgtctgc tattaataac  10500
tatgctcaaa aattgtgtac ctttagcttt ttaatttgta aaggggttaa taaggaatat  10560
ttgatgtata gtgccttgac tagagatcat aatcagccat accacatttg tagaggtttt  10620
acttgcttta aaaaacctcc cacacctccc cctgaacctg aaacataaaa tgaatgcaat  10680
tgttgttgtt aacttgttta ttgcagctta taatggttac aaataaagca atagcatcac  10740
aaatttcaca aataaagcat ttttttcact gcattctagt tgtggtttgt ccaaactcat  10800
caatgtatct tatcatgtct ggatcaactg gataactcaa gctaaccaaa atcatcccaa  10860
acttcccacc ccataccta ttaccactgc caattacctg tggtttcatt tactctaaac  10920
ctgtgattcc tctgaattat tttcatttta aagaaattgt atttgttaaa tatgtactac  10980
aaacttagta gt                                                      10992
```

<210> SEQ ID NO 50

<211> LENGTH: 13600
<212> TYPE: DNA
<213> ORGANISM: Artificial
<220> FEATURE:
<223> OTHER INFORMATION: Circular HIV-1 nucleic acid

<400> SEQUENCE: 50

```
tggaagggct aattcactcc caaagaagac aagatatcct tgatctgtgg atctaccaca     60
cacaaggcta cttccctgat tagcagaact acacaccagg gccagggtca gatatccact    120
gacctttgga tggtgctaca agctagtacc agttgagcca gataaggtag aagaggccaa    180
taaaggagag aacaccagct tgttacaccc tgtgagcctg catgggatgg atgacccgga    240
gagagaagtg ttagagtgga ggtttgacag ccgcctagca tttcatcacg tggcccgaga    300
gctgcatccg gagtacttca agaactgctg atatcgagct tgctacaagg gactttccgc    360
tggggacttt ccagggaggc gtggcctggg cgggactggg gagtggcgag ccctcagatc    420
ctgcatataa gcagctgctt tttgcctgta ctgggtctct ctggttagac cagatctgag    480
cctgggagct ctctggctaa ctagggaacc cactgcttaa gcctcaataa agcttgcctt    540
gagtgcttca agtagtgtgt gcccgtctgt tgtgtgactc tggtaactag agatccctca    600
gaccctttta gtcagtgtgg aaaatctcta gcttaattaa ccgtacgcgt actacgtata    660
aagccaggaa tggatggccc aaaagttaaa caatggccat tgacagaaga aaaaataaaa    720
gcattagtag aaatttgtac agagatggaa aaggaaggga aaatttcaaa aattgggcct    780
gaaaatccat acaatactcc agtatttgcc ataaagaaaa aagacagtac taaatggaga    840
aaattagtag atttcagaga acttaataag agaactcaag acttctggga agttcaatta    900
ggaataccac atcccgcagg gttaaaaaag aaaaaatcag taacagtact ggatgtgggt    960
gatgcatatt tttcagttcc cttagatgaa gacttcagga aatatactgc atttaccata   1020
cctagtataa acaatgagac accagggatt agatatcagt acaatgtgct tccacaggga   1080
tggaaaggat caccagcaat attccaaagt agcatgacaa aaatcttaga gccttttaga   1140
aaacaaaatc cagacatagt tatctatcaa tacatggatg atttgtatgt aggatctgac   1200
ttagaaatag ggcagcatag aacaaaaata gaggagctga gacaacatct gttgaggtgg   1260
ggacttacca caccagacaa aaaacatcag aaagaacctc cattcctttg gatgggttat   1320
gaactccatc ctgataaatg gacagtacag cctatagtgc tgccagaaaa agacagctgg   1380
actgtcaatg acatacagaa gttagtgggg aaattgaatt gggcaagtca gatttaccca   1440
gggattaaag taaggcaatt atgtaaactc cttagaggaa ccaaagcact aacagaagta   1500
ataccactaa cagaagaagc agagctagaa ctggcagaaa acagagagat tctaaaagaa   1560
ccagtacatg gagtgtatta tgacccatca aaagacttaa tagcagaaat acagaagcag   1620
gggcaaggcc aatggacata tcaaatttat caagagccat ttaaaaatct gaaaacagga   1680
aaatatgcaa gaatgagggg tgcccacact aatgatgtaa aacaattaac agaggcagtg   1740
caaaaaataa ccacagaaag catagtaata tggggaaaga ctcctaaatt taaactgccc   1800
atacaaaagg aaacatggga aacatggtgg acagagtatt ggcaagccac ctggattcct   1860
gagtgggagt ttgttaatac ccctcccttta gtgaaattat ggtaccagtt agagaaagaa   1920
cccatagtag gagcagaaac cttctatgta gatggggcag ctaacaggga gactaaatta   1980
ggaaaagcag gatatgttac taatagagga agacaaaaag ttgtcaccct aactgacaca   2040
acaaatcaga agactgagtt acaagcaatt tatctagctt tgcaggattc gggattagaa   2100
gtaaacatag taacagactc acaatatgca ttaggaatca ttcaagcaca accagatcaa   2160
```

-continued agtgaatcag agttagtcaa tcaaataata gagcagttaa taaaaaagga aaaggtctat 2220
ctggcatggg taccagcaca caaaggaatt ggaggaaatg aacaagtaga taaattagtc 2280
agtgctggaa tcaggaaagt actatttta gatggaatag ataaggccca agatgaacat 2340
gagaaatatc acagtaattg gagagcaatg gctagtgatt ttaacctgcc acctgtagta 2400
gcaaaagaaa tagtagccag ctgtgataaa tgtcagctaa aaggagaagc catgcatgga 2460
caagtagact gtagtccagg aatatggcaa ctagattgta cacatttaga aggaaaagtt 2520
atcctggtag cagttcatgt agccagtgga tatatagaag cagaagttat tccagcagaa 2580
acagggcagg aaacagcata ttttctttta aaattagcag gaagatggcc agtaaaaaca 2640
atacatacag acaatggcag caatttcacc agtgctacgg ttaaggccgc ctgttggtgg 2700
gcgggaatca agcaggaatt tggaattccc tacaatcccc aaagtcaagg agtagtagaa 2760
tctatgaata aagaattaaa gaaaattata ggacaggtaa gagatcaggc tgaacatctt 2820
aagacagcag tacaaatggc agtattcatc cacaatttta aaagaaaagg ggggattggg 2880
gggtacagtg caggggaaag aatagtagac ataatagcaa cagacataca aactaaagaa 2940
ttacaaaaac aaattacaaa aattcaaaat tttcgggttt attacaggga cagcagaaat 3000
ccactttgga aaggaccagc aaagctcctc tggaaaggtg aaggggcagt agtaatacaa 3060
gataatagtg acataaaagt agtgccaaga agaaaagcaa agatcattag ggattatgga 3120
aaacagatgg caggtgatga ttgtgtggca agtagacagg atgaggatta gaacatggaa 3180
aagtttagta aaacaccata tgtatgtttc agggaaagct aggggatggt tttatagaca 3240
tcactatgaa agccctcatc caagaataag ttcagaagta cacatcccac taggggatgc 3300
tagattggta ataacaacat attggggtct gcatacagga gaaagagact ggcatttggg 3360
tcagggagtc tccatagaat ggaggaaaaa gagatatagc acacaagtag accctgaact 3420
agcagaccaa ctaattcatc tgtattactt tgactgtttt tcagactctg ctataagaaa 3480
ggccttatta ggacacatag ttagccctag gtgtgaatat caagcaggac ataacaaggt 3540
aggatctcta caatacttgg cactagcagc attaataaca ccaaaaaaga taaagccacc 3600
tttgcctagt gttacgaaac tgacagagga tagatggaac aagccccaga agaccaaggg 3660
ccacagaggg agccacacaa tgaatggaca ctagagcttt tagaggagct taagaatgaa 3720
gctgttagac attttcctag gatttggctc catggcttag ggcaacatat ctatgaaact 3780
tatggggata cttgggcagg agtggaagcc ataataagaa ttctgcaaca actgctgttt 3840
atccattttc agaattgggt gtcgacatag cagaataggc gttactcgac agaggagagc 3900
aagaaatgga gccagtagat cctagactag agccctggaa gcatccagga agtcagccta 3960
aaactgcttg taccaattgc tattgtaaaa agtgttgctt tcattgccaa gtttgtttca 4020
taacaaaagc cttaggcatc tcctatggca ggaagaagcg gagacagcga cgaagagctc 4080
atcagaacag tcagactcat caagcttctc tatcaaagca gtaagtagta catgtaacgc 4140
aacctatacc aatagtagca atagtagcat tagtagtagc aataataata gcaatagttg 4200
tgtggtccat agtaatcata gaatatagga aaatattaag acaaagaaaa atagacaggt 4260
taattgatag actaatagaa agagcagaag acagtggcaa tgagagtgaa ggagaaatat 4320
cagcacttgt ggagatgggg gtggagatgg ggcaccatgc tccttgggat gttgatgatc 4380
tgtagtgcta cagaaaaatt gtgggtcaca gtctattatg gggtacctgt gtggaaggaa 4440
gcaaccacca ctctattttg tgcatcagat gctaaagcat atgatacaga ggtacataat 4500
gtttgggcca cacatgcctg tgtacccaca gaccccaacc cacaagaagt agtattggta 4560

-continued

```
aatgtgacag aaaattttaa catgtggaaa aatgacatgg tagaacagat gcatgaggat   4620
ataatcagtt tatgggatca aagcctaaag ccatgtgtaa aattaacccc actctgtgtt   4680
agtttaaagt gcactgattt gaagaatgat actaatacca atagtagtag cgggagaatg   4740
ataatggaga aaggagagat aaaaaactgc tctttcaata tcagcacaag cataagaggt   4800
aaggtgcaga aagaatatgc atttttttat aaacttgata taataccaat agataatgat   4860
actaccagct ataagttgac aagttgtaac acctcagtca ttacacaggc ctgtccaaag   4920
gtatcctttg agccaattcc catacattat tgtgccccgg ctggttttgc gattctaaaa   4980
tgtaataata agacgttcaa tggaacagga ccatgtacaa atgtcagcac agtacaatgt   5040
acacatggaa ttaggccagt agtatcaact caactgctgt taaatggcag tctagcagaa   5100
gaagaggtag taattagatc tgtcaatttc acggacaatg ctaaaaccat aatagtacag   5160
ctgaacacat ctgtagaaat taattgtaca agacccaaca acaatacaag aaaaagaatc   5220
cgtatccaga gaggaccagg gagagcattt gttacaatag gaaaaatagg aaatatgaga   5280
caagcacatt gtaacattag tagagcaaaa tggaataaca ctttaaaaca gatagctagc   5340
aaattaagag aacaatttgg aaataataaa acaataatct ttaagcaatc ctcaggaggg   5400
gacccagaaa ttgtaacgca cagttttaat tgtggagggg aatttttcta ctgtaattca   5460
acacaactgt ttaatagtac ttggtttaat agtacttgga gtactgaagg gtcaaataac   5520
actgaaggaa gtgacacaat caccctccca tgcagaataa aacaaattat aaacatgtgg   5580
cagaaagtag gaaaagcaat gtatgcccct cccatcagtg gacaaattag atgttcatca   5640
aatattacag ggctgctatt aacaagagat ggtggtaata gcaacaatga gtccgagatc   5700
ttcagacctg gaggaggaga tatgagggac aattggagaa gtgaattata taaatataaa   5760
gtagtaaaaa ttgaaccatt aggagtagca cccaccaagg caaagagaag agtggtgcag   5820
agagaaaaaa gagcagtggg aataggagct ttgttccttg ggttcttggg agcagcagga   5880
agcactatgg gcgcagcgtc aatgacgctg acggtacagg ccagacaatt attgtctggt   5940
atagtgcagc agcagaacaa tttgctgagg gctattgagg cgcaacagca tctgttgcaa   6000
ctcacagtct ggggcatcaa gcagctccag gcaagaatcc tggctgtgga aagataccta   6060
aaggatcaac agctcctggg gatttggggt tgctctggaa aactcatttg caccactgct   6120
gtgccttgga atgctagttg gagtaataaa tctctggaac agatttggaa tcacacgacc   6180
tggatggagt gggacagaga aattaacaat tacacaagct taatacactc cttaattgaa   6240
gaatcgcaaa accagcaaga aaagaatgaa caagaattat tggaattaga taaatgggca   6300
agtttgtgga attggtttaa cataacaaat tggctgtggt atataaaatt attcataatg   6360
atagtaggag gcttggtagg tttaagaata gtttttgctg tactttctat agtgaataga   6420
gttaggcagg gatattcacc attatcgttt cagacccacc tcccaacccc gaggggaccc   6480
gacaggcccg aaggaataga agaagaaggt ggagagagag acagagacag atccattcga   6540
ttagtgaacg gatccttagc acttatctgg gacgatctgc ggagcctgtg cctcttcagc   6600
taccaccgct tgagagactt actcttgatt gtaacgagga ttgtggaact tctgggacgc   6660
agggggtggg aagccctcaa atattggtgg aatctcctac aatattggag tcaggagcta   6720
aagaatagtg ctgttagctt gctcaatgcc acagccatag cagtagctga ggggacagat   6780
agggttatag aagtagtaca aggagcttgt agagctattc gccacatacc tagaagaata   6840
agacagggct tggaaaggat tttgctataa gatgggtggc gcggccgcaa tggtgagcaa   6900
gggcgaggag ctgttcaccg ggtggtgcc catcctggtc gagctggacg gcgacgtaaa   6960
```

-continued cggccacaag ttcagcgtgt ccggcgaggg cgagggcgat gccacctacg gcaagctgac 7020
cctgaagttc atctgcacca ccggcaagct gcccgtgccc tggcccaccc tcgtgaccac 7080
cctgacctac ggcgtgcagt gcttcagccg ctaccccgac cacatgaagc agcacgactt 7140
cttcaagtcc gccatgcccg aaggctacgt ccaggagcgc accatcttct tcaaggacga 7200
cggcaactac aagacccgcg ccgaggtgaa gttcgagggc gacaccctgg tgaaccgcat 7260
cgagctgaag ggcatcgact tcaaggagga cggcaacatc ctggggcaca agctggagta 7320
caactacaac agccacaacg tctatatcat ggccgacaag cagaagaacg gcatcaaggc 7380
gaacttcaag atccgccaca acatcgagga cggcagcgtg cagctcgccg accactacca 7440
gcagaacacc cccatcggcg acggccccgt gctgctgccc gacaaccact acctgagcac 7500
ccagtccgcc ctgagcaaag accccaacga gaagcgcgat cacatggtcc tgctggagtt 7560
cgtgaccgcc gccgggatca ctctcggcat ggacgagctg tacaagtaag aattctgact 7620
cgagacctag aaaaacatgg agcaatcaca agtagcaata cagcagctac caatgctgat 7680
tgtgcctggc tagaagcaca agaggaggag gaggtgggtt ttccagtcac acctcaggta 7740
cctttaagac caatgactta caaggcagct gtagatctta gccacttttt aaaagaaaag 7800
gggggactgg aagggctaat tcactcccaa cgaagacaag atatccttga tctgtggatc 7860
taccacacac aaggctactt ccctgattgg cagaactaca caccagggcc agggatcaga 7920
tatccactga cctttggatg gtgctacaag ctagtaccag ttgagcaaga gaaggtagaa 7980
gaagccaatg aaggagagaa cacccgcttg ttacaccctg tgagcctgca tgggatggat 8040
gacccggaga gagaagtatt agagtggagg tttgacagcc gcctagcatt tcatcacatg 8100
gcccgagagc tgcatccgga gtacttcaag aactgctgac atcgagcttg ctacaaggga 8160
ctttccgctg gggactttcc agggaggcgt ggcctgggcg ggactgggga gtggcgagcc 8220
ctcagatgct gcatataagc agctgctttt tgcttgtact gggtctctct ggttagacca 8280
gatctgagcc tgggagctct ctggctaact agggaaccca ctgcttaagc ctcaataaag 8340
cttgccttga gtgcttcaag tagtgtgtgc ccgtctgttg tgtgactctg gcgcgcctct 8400
agaattaatt ccgtgtattc tatagtgtca cctaaatcgt atgtgtatga tacataaggt 8460
tatgtattaa ttgtagccgc gttctaacga caatatgtac aagcctaatt gtgtagcatc 8520
tggcttactg aagcagaccc tatcatctct ctcgtaaact gccgtcagag tcggtttggt 8580
tggacgaacc ttctgagttt ctggtaacgc cgtcccgcac ccggaaatgg tcagcgaacc 8640
aatcagcagg gtcatcgcta gccagatcct ctacgccgga cgcatcgtgg ccggcatcac 8700
cggcgccaca ggtgcggttg ctggcgccta tatcgccgac atcaccgatg gggaagatcg 8760
ggctcgccac ttcgggctca tgagcgcttg tttcggcgtg ggtatggtgg caggccccgt 8820
ggccggggga ctgttgggcg ccatctcctt gcatgcacca ttccttgcgg cggcggtgct 8880
caacggcctc aacctactac tgggctgctt cctaatgcag gagtcgcata agggagagcg 8940
tcgaatggtg cactctcagt acaatctgct ctgatgccgc atagttaagc cagccccgac 9000
acccgccaac acccgctgac gcgccctgac gggcttgtct gctcccggca tccgcttaca 9060
gacaagctgt gaccgtctcc gggagctgca tgtgtcagag gttttcaccg tcatcaccga 9120
aacgcgcgag acgaaagggc ctcgtgatac gcctattttt ataggttaat gtcatgataa 9180
taatggtttc ttagacgtca ggtggcactt ttcggggaaa tgtgcgcgga acccctattt 9240
gtttattttt ctaaatacat tcaaatatgt atccgctcat gagacaataa ccctgataaa 9300
tgcttcaata atattgaaaa aggaagagta tgagtattca acatttccgt gtcgccctta 9360

-continued ttcccttttt tgcggcattt tgccttcctg tttttgctca cccagaaacg ctggtgaaag 9420
taaaagatgc tgaagatcag ttgggtgcac gagtgggtta catcgaactg gatctcaaca 9480
gcggtaagat ccttgagagt tttcgccccg aagaacgttt tccaatgatg agcactttta 9540
aagttctgct atgtggcgcg gtattatccc gtattgacgc cgggcaagag caactcggtc 9600
gccgcataca ctattctcag aatgacttgg ttgagtactc accagtcaca gaaaagcatc 9660
ttacggatgg catgacagta agagaattat gcagtgctgc cataaccatg agtgataaca 9720
ctgcggccaa cttacttctg acaacgatcg gaggaccgaa ggagctaacc gcttttttgc 9780
acaacatggg ggatcatgta actcgccttg atcgttggga accggagctg aatgaagcca 9840
taccaaacga cgagcgtgac accacgatgc ctgtagcaat ggcaacaacg ttgcgcaaac 9900
tattaactgg cgaactactt actctagctt cccggcaaca attaatagac tggatggagg 9960
cggataaagt tgcaggacca cttctgcgct cggcccttcc ggctggctgg tttattgctg 10020
ataaatctgg agccggtgag cgtgggtctc gcggtatcat tgcagcactg gggccagatg 10080
gtaagccctc ccgtatcgta gttatctaca cgacggggag tcaggcaact atggatgaac 10140
gaaatagaca gatcgctgag ataggtgcct cactgattaa gcattggtaa ctgtcagacc 10200
aagtttactc atatatactt tagattgatt taaaacttca tttttaattt aaaaggatct 10260
aggtgaagat cctttttgat aatctcatga ccaaaatccc ttaacgtgag ttttcgttcc 10320
actgagcgtc agaccccgta gaaaagatca aaggatcttc ttgagatcct ttttttctgc 10380
gcgtaatctg ctgcttgcaa acaaaaaaac caccgctacc agcggtggtt tgtttgccgg 10440
atcaagagct accaactctt tttccgaagg taactggctt cagcagagcg cagataccaa 10500
atactgttct tctagtgtag ccgtagttag gccaccactt caagaactct gtagcaccgc 10560
ctacatacct cgctctgcta atcctgttac cagtggctgc tgccagtggc gataagtcgt 10620
gtcttaccgg gttggactca agacgatagt taccggataa ggcgcagcgg tcgggctgaa 10680
cggggggttc gtgcacacag cccagcttgg agcgaacgac ctacaccgaa ctgagatacc 10740
tacagcgtga gctatgagaa agcgccacgc ttcccgaagg gagaaaggcg gacaggtatc 10800
cggtaagcgg cagggtcgga acaggagagc gcacgaggga gcttccaggg ggaaacgcct 10860
ggtatcttta tagtcctgtc gggtttcgcc acctctgact tgagcgtcga tttttgtgat 10920
gctcgtcagg ggggcggagc ctatggaaaa acgccagcaa cgcggccttt ttacggttcc 10980
tggccttttg ctggcctttt gctcacatgt tctttcctgc gttatcccct gattctgtgg 11040
ataaccgtat taccgccttt gagtgagctg ataccgctcg ccgcagccga acgaccgagc 11100
gcagcgagtc agtgagcgag gaagcggaag agcgcccaat acgcaaaccg cctctccccg 11160
cgcgttggcc gattcattaa tgcagctgtg gaatgtgtgt cagttagggt gtggaaagtc 11220
cccaggctcc ccagcaggca gaagtatgca aagcatgcat ctcaattagt cagcaaccag 11280
gtgtggaaag tccccaggct ccccagcagg cagaagtatg caaagcatgc atctcaatta 11340
gtcagcaacc atagtcccgc ccctaactcc gcccatcccg cccctaactc cgcccagttc 11400
cgcccattct ccgccccatg gctgactaat tttttttatt tatgcagagg ccgaggccgc 11460
ctcggcctct gagctattcc agaagtagtg aggaggcttt tttggaggcc taggcttttg 11520
caaaaagctt ggacacaaga caggcttgcg agatatgttt gagaatacca ctttatcccg 11580
cgtcagggag aggcagtgcg taaaaagacg cggactcatg tgaaatactg gtttttagtg 11640
cgccagatct ctataatctc gcgcaaccta ttttcccctc gaacactttt taagccgtag 11700
ataaacaggc tgggacactt cacatgagcg aaaaatacat cgtcacctgg gacatgttgc 11760

-continued

```
agatccatgc acgtaaactc gcaagccgac tgatgccttc tgaacaatgg aaaggcatta  11820

ttgccgtaag ccgtggcggt ctggtaccgg gtgcgttact ggcgcgtgaa ctgggtattc  11880

gtcatgtcga taccgtttgt atttccagct acgatcacga caaccagcgc gagcttaaag  11940

tgctgaaacg cgcagaaggc gatggcgaag gcttcatcgt tattgatgac ctggtggata  12000

ccggtggtac tgcggttgcg attcgtgaaa tgtatccaaa agcgcacttt gtcaccatct  12060

tcgcaaaacc ggctggtcgt ccgctggttg atgactatgt tgttgatatc ccgcaagata  12120

cctggattga acagccgtgg gatatgggcg tcgtattcgt cccgccaatc tccggtcgct  12180

aatcttttca acgcctggca ctgccgggcg ttgttctttt taacttcagg cgggttacaa  12240

tagtttccag taagtattct ggaggctgca tccatgacac aggcaaacct gagcgaaacc  12300

ctgttcaaac cccgctttaa acatcctgaa acctcgacgc tagtccgccg ctttaatcac  12360

ggcgcacaac cgcctgtgca gtcggccctt gatggtaaaa ccatccctca ctggtatcgc  12420

atgattaacc gtctgatgtg gatctggcgc ggcattgacc cacgcgaaat cctcgacgtc  12480

caggcacgta ttgtgatgag cgatgccgaa cgtaccgacg atgatttata cgatacggtg  12540

attggctacc gtggcggcaa ctggatttat gagtgggccc cggatctttg tgaaggaacc  12600

ttacttctgt ggtgtgacat aattggacaa actacctaca gagatttaaa gctctaaggt  12660

aaatataaaa tttttaagtg tataatgtgt taaactactg attctaattg tttgtgtatt  12720

ttagattcca acctatggaa ctgatgaatg ggagcagtgg tggaatgcct ttaatgagga  12780

aaacctgttt tgctcagaag aaatgccatc tagtgatgat gaggctactg ctgactctca  12840

acattctact cctccaaaaa agaagagaaa ggtagaagac cccaaggact ttccttcaga  12900

attgctaagt tttttgagtc atgctgtgtt tagtaataga actcttgctt gctttgctat  12960

ttacaccaca aaggaaaaag ctgcactgct atacaagaaa attatggaaa aatattctgt  13020

aacctttata agtaggcata acagttataa tcataacata ctgttttttc ttactccaca  13080

caggcataga gtgtctgcta ttaataacta tgctcaaaaa ttgtgtacct ttagcttttt  13140

aatttgtaaa ggggttaata aggaatattt gatgtatagt gccttgacta gagatcataa  13200

tcagccatac cacatttgta gaggttttac ttgctttaaa aaacctccca cacctccccc  13260

tgaacctgaa acataaaatg aatgcaattg ttgttgttaa cttgtttatt gcagcttata  13320

atggttacaa ataaagcaat agcatcacaa atttcacaaa taaagcattt ttttcactgc  13380

attctagttg tggtttgtcc aaactcatca atgtatctta tcatgtctgg atcaactgga  13440

taactcaagc taaccaaaat catcccaaac ttcccacccc ataccctatt accactgcca  13500

attacctgtg gtttcattta ctctaaacct gtgattcctc tgaattattt tcattttaaa  13560

gaaattgtat ttgttaaata tgtactacaa acttagtagt                        13600
```

<210> SEQ ID NO 51
<211> LENGTH: 12682
<212> TYPE: DNA
<213> ORGANISM: Artificial
<220> FEATURE:
<223> OTHER INFORMATION: Circular HIV-1 nucleic acid

<400> SEQUENCE: 51

```
tggaagggct aattcactcc caaagaagac aagatatcct tgatctgtgg atctaccaca     60

cacaaggcta cttccctgat tagcagaact acacaccagg gccagggtca gatatccact    120

gacctttgga tggtgctaca agctagtacc agttgagcca gataaggtag aagaggccaa    180

taaaggagag aacaccagct tgttacaccc tgtgagcctg catgggatgg atgacccgga    240
```

-continued

```
gagagaagtg ttagagtgga ggtttgacag ccgcctagca tttcatcacg tggcccgaga    300
gctgcatccg gagtacttca agaactgctg atatcgagct tgctacaagg gactttccgc    360
tggggacttt ccagggaggc gtggcctggg cgggactggg gagtggcgag ccctcagatc    420
ctgcatataa gcagctgctt tttgcctgta ctgggtctct ctggttagac cagatctgag    480
cctgggagct ctctggctaa ctagggaacc cactgcttaa gcctcaataa agcttgcctt    540
gagtgcttca agtagtgtgt gcccgtctgt tgtgtgactc tggtaactag agatccctca    600
gaccctttta gtcagtgtgg aaaatctcta gcagtggcgc ccgaacaggg acttgaaagc    660
gaaagggaaa ccagaggagc tctctcgacg caggactcgg cttgctgaag cgcgcacggc    720
aagaggcgag gggcggcgac tggtgagtac gccaaaaatt ttgactagcg gaggctagaa    780
ggagagagat gggtgcgaga gcgtcagtat taagcggggg agaattagat cgatgggaaa    840
aaattcggtt aaggccaggg ggaaagaaaa aatataaatt aaaacatata gtatgggcaa    900
gcagggagct agaacgattc gcagttaatc ctggcctgtt agaaacatca gaaggctgta    960
gacaaatact gggacagcta caaccatccc ttcagacagg atcagaagaa cttagatcat   1020
tatataatac agtagcaacc ctctattgtg tgcatcaaag gatagagata aaagacacca   1080
aggaagcttt agacaagata gaggaagagc aaaacaaaag taagaaaaaa gcacagcaag   1140
cagcagctga cacaggacac agcaatcagg tcagccaaaa ttaccctata gtgcagaaca   1200
tccaggggca aatggtacat caggccatat cacctagaac tttaaatgca tgggtaaaag   1260
tagtagaaga gaaggctttc agcccagaag tgatacccat gttttcagca ttatcagaag   1320
gagccacccc acaagattta aacaccatgc taaacacagt ggggggacat caagcagcca   1380
tgcaaatgtt aaaagagacc atcaatgagg aagctgcaga atgggataga gtgcatccag   1440
tgcatgcagg gcctattgca ccaggccaga tgagagaacc aaggggaagt gacatagcag   1500
gaactactag tacccttcag gaacaaatag gatggatgac aaataatcca cctatcccag   1560
taggagaaat ttataaaaga tggataatcc tgggattaaa taaaatagta agaatgtata   1620
gccctaccag cattctggac ataagacaag gaccaaaaga accctttaga gactatgtag   1680
accggttcta taaaactcta agagccgagc aagcttcaca ggaggtaaaa aattggatga   1740
cagaaacctt gttggtccaa aatgcgaacc cagattgtaa gactatttta aaagcattgg   1800
gaccagcggc tacactagaa gaaatgatga cagcatgtca gggagtagga ggacccggcc   1860
ataaggcaag agttttggct gaagcaatga gccaagtaac aaattcagct accataatga   1920
tgcagagagg caattttagg aaccaaagaa agattgttaa gtgtttcaat tgtggcaaag   1980
aagggcacac agccagaaat tgcagggccc ctaggaaaaa gggctgttgg aaatgtggaa   2040
aggaaggaca ccaaatgaaa gattgtactg agagacaggc taattttttta gggaagatct   2100
ggccttccta caagggaagg ccagggaatt ttcttcagag cagaccagag ccaacagccc   2160
caccagaaga gagcttcagg tctggggtag agacaacaac tccccctcag aagcaggagc   2220
cgatagacaa ggaactgtat cctttaactt ccctcagatc actctttggc aacgacccct   2280
cgtcacaata aagatagggg ggcaactaaa ggaagctcta ttagatacat taattaaccg   2340
tacgcgtact acgtaagaag tacacatccc actaggggat gctagattgg taataacaac   2400
atattggggt ctgcatacag gagaaagaga ctggcatttg ggtcagggag tctccataga   2460
atggaggaaa aagagatata gcacacaagt agaccctgaa ctagcagacc aactaattca   2520
tctgtattac tttgactgtt tttcagactc tgctataaga aaggccttat taggacacat   2580
agttagccct aggtgtgaat atcaagcagg acataacaag gtaggatctc tacaatactt   2640
```

-continued

```
ggcactagca gcattaataa caccaaaaaa gataaagcca cctttgccta gtgttacgaa   2700
actgacagag gatagatgga acaagcccca gaagaccaag ggccacagag ggagccacac   2760
aatgaatgga cactagagct tttagaggag cttaagaatg aagctgttag acattttcct   2820
aggatttggc tccatggctt agggcaacat atctatgaaa cttatgggga tacttgggca   2880
ggagtggaag ccataataag aattctgcaa caactgctgt ttatccattt tcagaattgg   2940
gtgtcgacat agcagaatag gcgttactcg acagaggaga gcaagaaatg gagccagtag   3000
atcctagact agagccctgg aagcatccag gaagtcagcc taaaactgct tgtaccaatt   3060
gctattgtaa aaagtgttgc tttcattgcc aagtttgttt cataacaaaa gccttaggca   3120
tctcctatgg caggaagaag cggagacagc gacgaagagc tcatcagaac agtcagactc   3180
atcaagcttc tctatcaaag cagtaagtag tacatgtaac gcaacctata ccaatagtag   3240
caatagtagc attagtagta gcaataataa tagcaatagt tgtgtggtcc atagtaatca   3300
tagaatatag gaaaatatta agacaaagaa aaatagacag gttaattgat agactaatag   3360
aaagagcaga agacagtggc aatgagagtg aaggagaaat atcagcactt gtggagatgg   3420
gggtggagat ggggcaccat gctccttggg atgttgatga tctgtagtgc tacagaaaaa   3480
ttgtgggtca cagtctatta tggggtacct gtgtggaagg aagcaaccac cactctattt   3540
tgtgcatcag atgctaaagc atatgataca gaggtacata atgtttgggc cacacatgcc   3600
tgtgtaccca cagaccccaa cccacaagaa gtagtattgg taaatgtgac agaaaatttt   3660
aacatgtgga aaaatgacat ggtagaacag atgcatgagg atataatcag tttatgggat   3720
caaagcctaa agccatgtgt aaaattaacc ccactctgtg ttagtttaaa gtgcactgat   3780
ttgaagaatg atactaatac caatagtagt agcgggagaa tgataatgga gaaaggagag   3840
ataaaaaact gctctttcaa tatcagcaca agcataagag gtaaggtgca gaaagaatat   3900
gcattttttt ataaacttga tataatacca atagataatg atactaccag ctataagttg   3960
acaagttgta acacctcagt cattacacag gcctgtccaa aggtatcctt tgagccaatt   4020
cccatacatt attgtgcccc ggctggtttt gcgattctaa aatgtaataa taagacgttc   4080
aatggaacag gaccatgtac aaatgtcagc acagtacaat gtacacatgg aattaggcca   4140
gtagtatcaa ctcaactgct gttaaatggc agtctagcag aagaagaggt agtaattaga   4200
tctgtcaatt tcacggacaa tgctaaaacc ataatagtac agctgaacac atctgtagaa   4260
attaattgta caagacccaa caacaataca agaaaaagaa tccgtatcca gagaggacca   4320
gggagagcat ttgttacaat aggaaaaata ggaaatatga gacaagcaca ttgtaacatt   4380
agtagagcaa aatggaataa cactttaaaa cagatagcta gcaaattaag agaacaattt   4440
ggaaataata aaacaataat ctttaagcaa tcctcaggag gggacccaga aattgtaacg   4500
cacagtttta attgtggagg ggaatttttc tactgtaatt caacacaact gtttaatagt   4560
acttggttta atagtacttg gagtactgaa gggtcaaata acactgaagg aagtgacaca   4620
atcaccctcc catgcagaat aaaacaaatt ataaacatgt ggcagaaagt aggaaaagca   4680
atgtatgccc ctcccatcag tggacaaatt agatgttcat caaatattac agggctgcta   4740
ttaacaagag atggtggtaa tagcaacaat gagtccgaga tcttcagacc tggaggagga   4800
gatatgaggg acaattggag aagtgaatta tataaatata aagtagtaaa aattgaacca   4860
ttaggagtag cacccaccaa ggcaaagaga agagtggtgc agagagaaaa aagagcagtg   4920
ggaataggag ctttgttcct tgggttcttg ggagcagcag gaagcactat gggcgcagcg   4980
tcaatgacgc tgacggtaca ggccagacaa ttattgtctg gtatagtgca gcagcagaac   5040
```

-continued

```
aatttgctga gggctattga ggcgcaacag catctgttgc aactcacagt ctggggcatc   5100
aagcagctcc aggcaagaat cctggctgtg gaaagatacc taaaggatca acagctcctg   5160
gggatttggg gttgctctgg aaaactcatt tgcaccactg ctgtgccttg gaatgctagt   5220
tggagtaata aatctctgga acagatttgg aatcacacga cctggatgga gtgggacaga   5280
gaaattaaca attacacaag cttaatacac tccttaattg aagaatcgca aaaccagcaa   5340
gaaaagaatg aacaagaatt attggaatta gataaatggg caagtttgtg gaattggttt   5400
aacataacaa attggctgtg gtatataaaa ttattcataa tgatagtagg aggcttggta   5460
ggtttaagaa tagtttttgc tgtactttct atagtgaata gagttaggca gggatattca   5520
ccattatcgt ttcagaccca cctcccaacc ccgaggggac ccgacaggcc cgaaggaata   5580
gaagaagaag gtggagagag agacagagac agatccattc gattagtgaa cggatcctta   5640
gcacttatct gggacgatct gcggagcctg tgcctcttca gctaccaccg cttgagagac   5700
ttactcttga ttgtaacgag gattgtggaa cttctgggac gcagggggtg ggaagccctc   5760
aaatattggt ggaatctcct acaatattgg agtcaggagc taaagaatag tgctgttagc   5820
ttgctcaatg ccacagccat agcagtagct gaggggacag atagggttat agaagtagta   5880
caaggagctt gtagagctat tcgccacata cctagaagaa taagacaggg cttggaaagg   5940
attttgctat aagatgggtg gcgcggccgc aatggtgagc aagggcgagg agctgttcac   6000
cggggtggtg cccatcctgg tcgagctgga cggcgacgta aacggccaca agttcagcgt   6060
gtccggcgag ggcgagggcg atgccaccta cggcaagctg accctgaagt tcatctgcac   6120
caccggcaag ctgcccgtgc cctggcccac cctcgtgacc accctgacct acggcgtgca   6180
gtgcttcagc cgctaccccg accacatgaa gcagcacgac ttcttcaagt ccgccatgcc   6240
cgaaggctac gtccaggagc gcaccatctt cttcaaggac gacggcaact acaagacccg   6300
cgccgaggtg aagttcgagg gcgacaccct ggtgaaccgc atcgagctga agggcatcga   6360
cttcaaggag gacggcaaca tcctggggca caagctggag tacaactaca acagccacaa   6420
cgtctatatc atggccgaca agcagaagaa cggcatcaag gcgaacttca agatccgcca   6480
caacatcgag gacggcagcg tgcagctcgc cgaccactac cagcagaaca cccccatcgg   6540
cgacggcccc gtgctgctgc ccgacaacca ctacctgagc acccagtccg ccctgagcaa   6600
agaccccaac gagaagcgcg atcacatggt cctgctggag ttcgtgaccg ccgccgggat   6660
cactctcggc atggacgagc tgtacaagta agaattctga ctcgagacct agaaaaacat   6720
ggagcaatca caagtagcaa tacagcagct accaatgctg attgtgcctg gctagaagca   6780
caagaggagg aggaggtggg ttttccagtc acacctcagg tacctttaag accaatgact   6840
tacaaggcag ctgtagatct tagccacttt ttaaaagaaa aggggggact ggaagggcta   6900
attcactccc aacgaagaca agatatcctt gatctgtgga tctaccacac acaaggctac   6960
ttccctgatt ggcagaacta cacaccaggg ccagggatca gatatccact gacctttgga   7020
tggtgctaca agctagtacc agttgagcaa gagaaggtag aagaagccaa tgaaggagag   7080
aacacccgct tgttacaccc tgtgagcctg catgggatgg atgacccgga gagagaagta   7140
ttagagtgga ggtttgacag ccgcctagca tttcatcaca tggcccgaga gctgcatccg   7200
gagtacttca agaactgctg acatcgagct tgctacaagg gactttccgc tggggacttt   7260
ccagggaggc gtggcctggg cgggactggg gagtggcgag ccctcagatg ctgcatataa   7320
gcagctgctt tttgcttgta ctgggtctct ctggttagac cagatctgag cctgggagct   7380
ctctggctaa ctagggaacc cactgcttaa gcctcaataa agcttgcctt gagtgcttca   7440
```

-continued

```
agtagtgtgt gcccgtctgt tgtgtgactc tggcgcgcct ctagaattaa ttccgtgtat   7500
tctatagtgt cacctaaatc gtatgtgtat gatacataag gttatgtatt aattgtagcc   7560
gcgttctaac gacaatatgt acaagcctaa ttgtgtagca tctggcttac tgaagcagac   7620
cctatcatct ctctcgtaaa ctgccgtcag agtcggtttg gttggacgaa ccttctgagt   7680
ttctggtaac gccgtcccgc acccggaaat ggtcagcgaa ccaatcagca gggtcatcgc   7740
tagccagatc ctctacgccg gacgcatcgt ggccggcatc accggcgcca caggtgcggt   7800
tgctggcgcc tatatcgccg acatcaccga tggggaagat cgggctcgcc acttcgggct   7860
catgagcgct tgtttcggcg tgggtatggt ggcaggcccc gtggccgggg gactgttggg   7920
cgccatctcc ttgcatgcac cattccttgc ggcggcggtg ctcaacggcc tcaacctact   7980
actgggctgc ttcctaatgc aggagtcgca taagggagag cgtcgaatgg tgcactctca   8040
gtacaatctg ctctgatgcc gcatagttaa gccagccccg acacccgcca acacccgctg   8100
acgcgccctg acgggcttgt ctgctcccgg catccgctta cagacaagct gtgaccgtct   8160
ccgggagctg catgtgtcag aggttttcac cgtcatcacc gaaacgcgcg agacgaaagg   8220
gcctcgtgat acgcctattt ttataggtta atgtcatgat aataatggtt tcttagacgt   8280
caggtggcac ttttcgggga aatgtgcgcg gaacccctat ttgtttattt ttctaaatac   8340
attcaaatat gtatccgctc atgagacaat aaccctgata aatgcttcaa taatattgaa   8400
aaaggaagag tatgagtatt caacatttcc gtgtcgccct tattcccttt tttgcggcat   8460
tttgccttcc tgtttttgct cacccagaaa cgctggtgaa agtaaaagat gctgaagatc   8520
agttgggtgc acgagtgggt tacatcgaac tggatctcaa cagcggtaag atccttgaga   8580
gttttcgccc cgaagaacgt tttccaatga tgagcacttt taaagttctg ctatgtggcg   8640
cggtattatc ccgtattgac gccgggcaag agcaactcgg tcgccgcata cactattctc   8700
agaatgactt ggttgagtac tcaccagtca cagaaaagca tcttacggat ggcatgacag   8760
taagagaatt atgcagtgct gccataacca tgagtgataa cactgcggcc aacttacttc   8820
tgacaacgat cggaggaccg aaggagctaa ccgctttttt gcacaacatg ggggatcatg   8880
taactcgcct tgatcgttgg gaaccggagc tgaatgaagc cataccaaac gacgagcgtg   8940
acaccacgat gcctgtagca atggcaacaa cgttgcgcaa actattaact ggcgaactac   9000
ttactctagc ttcccggcaa caattaatag actggatgga ggcggataaa gttgcaggac   9060
cacttctgcg ctcggccctt ccggctggct ggtttattgc tgataaatct ggagccggtg   9120
agcgtgggtc tcgcggtatc attgcagcac tggggccaga tggtaagccc tcccgtatcg   9180
tagttatcta cacgacgggg agtcaggcaa ctatggatga acgaaataga cagatcgctg   9240
agataggtgc ctcactgatt aagcattggt aactgtcaga ccaagtttac tcatatatac   9300
tttagattga tttaaaactt catttttaat ttaaaaggat ctaggtgaag atcctttttg   9360
ataatctcat gaccaaaatc ccttaacgtg agttttcgtt ccactgagcg tcagaccccg   9420
tagaaaagat caaaggatct tcttgagatc cttttttttct gcgcgtaatc tgctgcttgc   9480
aaacaaaaaa accaccgcta ccagcggtgg tttgtttgcc ggatcaagag ctaccaactc   9540
tttttccgaa ggtaactggc ttcagcagag cgcagatacc aaatactgtt cttctagtgt   9600
agccgtagtt aggccaccac ttcaagaact ctgtagcacc gcctacatac ctcgctctgc   9660
taatcctgtt accagtggct gctgccagtg gcgataagtc gtgtcttacc gggttggact   9720
caagacgata gttaccggat aaggcgcagc ggtcgggctg aacggggggt tcgtgcacac   9780
agcccagctt ggagcgaacg acctacaccg aactgagata cctacagcgt gagctatgag   9840
```

-continued

```
aaagcgccac gcttcccgaa gggagaaagg cggacaggta tccggtaagc ggcagggtcg   9900
gaacaggaga gcgcacgagg gagcttccag ggggaaacgc ctggtatctt tatagtcctg   9960
tcgggtttcg ccacctctga cttgagcgtc gatttttgtg atgctcgtca ggggggcgga  10020
gcctatggaa aaacgccagc aacgcggcct ttttacggtt cctggccttt tgctggcctt  10080
ttgctcacat gttctttcct gcgttatccc ctgattctgt ggataaccgt attaccgcct  10140
ttgagtgagc tgataccgct cgccgcagcc gaacgaccga gcgcagcgag tcagtgagcg  10200
aggaagcgga agagcgccca atacgcaaac cgcctctccc cgcgcgttgg ccgattcatt  10260
aatgcagctg tggaatgtgt gtcagttagg gtgtggaaag tccccaggct ccccagcagg  10320
cagaagtatg caaagcatgc atctcaatta gtcagcaacc aggtgtggaa agtccccagg  10380
ctccccagca ggcagaagta tgcaaagcat gcatctcaat tagtcagcaa ccatagtccc  10440
gcccctaact ccgcccatcc cgcccctaac tccgcccagt tccgcccatt ctccgcccca  10500
tggctgacta atttttttta tttatgcaga ggccgaggcc gcctcggcct ctgagctatt  10560
ccagaagtag tgaggaggct tttttggagg cctaggcttt tgcaaaaagc ttggacacaa  10620
gacaggcttg cgagatatgt ttgagaatac cactttatcc cgcgtcaggg agaggcagtg  10680
cgtaaaaaga cgcggactca tgtgaaatac tggtttttag tgcgccagat ctctataatc  10740
tcgcgcaacc tattttcccc tcgaacactt tttaagccgt agataaacag gctgggacac  10800
ttcacatgag cgaaaaatac atcgtcacct gggacatgtt gcagatccat gcacgtaaac  10860
tcgcaagccg actgatgcct tctgaacaat ggaaaggcat tattgccgta agccgtggcg  10920
gtctggtacc gggtgcgtta ctggcgcgtg aactgggtat tcgtcatgtc gataccgttt  10980
gtatttccag ctacgatcac gacaaccagc gcgagcttaa agtgctgaaa cgcgcagaag  11040
gcgatggcga aggcttcatc gttattgatg acctggtgga taccggtggt actgcggttg  11100
cgattcgtga aatgtatcca aaagcgcact ttgtcaccat cttcgcaaaa ccggctggtc  11160
gtccgctggt tgatgactat gttgttgata tcccgcaaga tacctggatt gaacagccgt  11220
gggatatggg cgtcgtattc gtcccgccaa tctccggtcg ctaatctttt caacgcctgg  11280
cactgccggg cgttgttctt tttaacttca ggcgggttac aatagtttcc agtaagtatt  11340
ctggaggctg catccatgac acaggcaaac ctgagcgaaa ccctgttcaa accccgcttt  11400
aaacatcctg aaacctcgac gctagtccgc cgctttaatc acggcgcaca accgcctgtg  11460
cagtcggccc ttgatggtaa aaccatccct cactggtatc gcatgattaa ccgtctgatg  11520
tggatctggc gcggcattga cccacgcgaa atcctcgacg tccaggcacg tattgtgatg  11580
agcgatgccg aacgtaccga cgatgattta tacgatacgg tgattggcta ccgtggcggc  11640
aactggattt atgagtgggc cccggatctt tgtgaaggaa ccttacttct gtggtgtgac  11700
ataattggac aaactaccta cagagattta aagctctaag gtaaatataa aatttttaag  11760
tgtataatgt gttaaactac tgattctaat tgtttgtgta ttttagattc caacctatgg  11820
aactgatgaa tgggagcagt ggtggaatgc ctttaatgag gaaaacctgt tttgctcaga  11880
agaaatgcca tctagtgatg atgaggctac tgctgactct caacattcta ctcctccaaa  11940
aaagaagaga aaggtagaag accccaagga ctttccttca gaattgctaa gttttttgag  12000
tcatgctgtg tttagtaata gaactcttgc ttgctttgct atttacacca caaaggaaaa  12060
agctgcactg ctatacaaga aaattatgga aaaatattct gtaaccttta taagtaggca  12120
taacagttat aatcataaca tactgttttt tcttactcca cacaggcata gagtgtctgc  12180
tattaataac tatgctcaaa aattgtgtac ctttagcttt ttaatttgta aaggggttaa  12240
```

```
taaggaatat ttgatgtata gtgccttgac tagagatcat aatcagccat accacatttg  12300

tagaggtttt acttgcttta aaaaacctcc cacacctccc cctgaacctg aaacataaaa  12360

tgaatgcaat tgttgttgtt aacttgttta ttgcagctta taatggttac aaataaagca  12420

atagcatcac aaatttcaca aataaagcat ttttttcact gcattctagt tgtggtttgt  12480

ccaaactcat caatgtatct tatcatgtct ggatcaactg gataactcaa gctaaccaaa  12540

atcatcccaa acttcccacc ccatacccta ttaccactgc caattacctg tggtttcatt  12600

tactctaaac ctgtgattcc tctgaattat tttcatttta aagaaattgt atttgttaaa  12660

tatgtactac aaacttagta gt                                            12682
```

<210> SEQ ID NO 52
<211> LENGTH: 12378
<212> TYPE: DNA
<213> ORGANISM: Artificial
<220> FEATURE:
<223> OTHER INFORMATION: Circular HIV-1 nucleic acid

<400> SEQUENCE: 52

```
gaatgcaatt gttgttgtta acttgtttat tgcagcttat aatggttaca aataaagcaa     60

tagcatcaca aatttcacaa ataaagcatt tttttcactg cattctagtt gtggtttgtc    120

caaactcatc aatgtatctt atcatgtctg gatcaactgg ataactcaag ctaaccaaaa    180

tcatcccaaa cttcccaccc cataccctat taccactgcc aattacctgt ggtttcattt    240

actctaaacc tgtgattcct ctgaattatt ttcattttaa agaaattgta tttgttaaat    300

atgtactaca aacttagtag ttggaagggc taattcactc ccaaagaaga caagatatcc    360

ttgatctgtg gatctaccac acacaaggct acttccctga ttagcagaac tacacaccag    420

ggccagggtc agatatccac tgacctttgg atggtgctac aagctagtac cagttgagcc    480

agataaggta gaagaggcca ataaaggaga gaacaccagc ttgttacacc ctgtgagcct    540

gcatgggatg gatgacccgg agagagaagt gttagagtgg aggtttgaca gccgcctagc    600

atttcatcac gtggcccgag agctgcatcc ggagtacttc aagaactgct gatatcgagc    660

ttgctacaag ggactttccg ctggggactt tccagggagg cgtggcctgg gcgggactgg    720

ggagtggcga gccctcagat cctgcatata agcagctgct ttttgcctgt actgggtctc    780

tctggttaga ccagatctga gcctgggagc tctctggcta actagggaac ccactgctta    840

agcctcaata aagcttgcct tgagtgcttc aagtagtgtg tgcccgtctg ttgtgtgact    900

ctggtaacta gagatccctc agaccctttt agtcagtgtg gaaaatctct agcagtggcg    960

cccgaacagg gacttgaaag cgaaagggaa accagaggag ctctctcgac gcaggactcg   1020

gcttgctgaa gcgcgcacgg caagaggcga ggggcggcga ctggtgagta cgccaaaaat   1080

tttgactagc ggaggctaga aggagagaga tgggtgcgag agcgtcagta ttaagcgggg   1140

gagaattaga tcgatgggaa aaaattcggt taaggccagg gggaaagaaa aaatataaat   1200

taaaacatat agtatgggca agcagggagc tagaacgatt cgcagttaat cctggcctgt   1260

tagaaacatc agaaggctgt agacaaatac tgggacagct acaaccatcc cttcagacag   1320

gatcagaaga acttagatca ttatataata cagtagcaac cctctattgt gtgcatcaaa   1380

ggatagagat aaaagacacc aaggaagctt tagacaagat agaggaagag caaaacaaaa   1440

gtaagaaaaa agcacagcaa gcagcagctg acacaggaca cagcaatcag gtcagccaaa   1500

attaccctat agtgcagaac atccaggggc aaatggtaca tcaggccata tcacctagaa   1560

ctttaaatgc atgggtaaaa gtagtagaag agaaggcttt cagcccagaa gtgataccca   1620
```

```
tgttttcagc attatcagaa ggagccaccc cacaagattt aaacaccatg ctaaacacag   1680
tggggggaca tcaagcagcc atgcaaatgt taaaagagac catcaatgag gaagctgcag   1740
aatgggatag agtgcatcca gtgcatgcag ggcctattgc accaggccag atgagagaac   1800
caaggggaag tgacatagca ggaactacta gtacccttca ggaacaaata ggatggatga   1860
caaataatcc acctatccca gtaggagaaa tttataaaag atggataatc ctgggattaa   1920
ataaaatagt aagaatgtat agccctacca gcattctgga cataagacaa ggaccaaaag   1980
aaccctttag agactatgta gaccggttct ataaaactct aagagccgag caagcttcac   2040
aggaggtaaa aaattggatg acagaaacct tgttggtcca aaatgcgaac ccagattgta   2100
agactatttt aaaagcattg ggaccagcgg ctacactaga agaaatgatg acagcatgtc   2160
agggagtagg aggacccggc cataaggcaa gagttttggc tgaagcaatg agccaagtaa   2220
caaattcagc taccataatg atgcagagag gcaattttag gaaccaaaga aagattgtta   2280
agtgtttcaa ttgtggcaaa gaagggcaca cagccagaaa ttgcagggcc cctaggaaaa   2340
agggctttaa ttaaccgtac gcgtactacg taagaagtac acatcccact aggggatgct   2400
agattggtaa taacaacata ttggggtctg catacaggag aaagagactg gcatttgggt   2460
cagggagtct ccatagaatg gaggaaaaag agatatagca cacaagtaga ccctgaacta   2520
gcagaccaac taattcatct gtattacttt gactgttttt cagactctgc tataagaaag   2580
gccttattag gacacatagt tagccctagg tgtgaatatc aagcaggaca taacaaggta   2640
ggatctctac aatacttggc actagcagca ttaataacac caaaaaagat aaagccacct   2700
ttgcctagtg ttacgaaact gacagaggat agatggaaca agccccagaa gaccaagggc   2760
cacagaggga gccacacaat gaatggacac tagagctttt agaggagctt aagaatgaag   2820
ctgttagaca ttttcctagg atttggctcc atggcttagg gcaacatatc tatgaaactt   2880
atggggatac ttgggcagga gtggaagcca taataagaat tctgcaacaa ctgctgttta   2940
tccattttca gaattgggtg tcgacatagc agaataggcg ttactcgaca gaggagagca   3000
agaaatggag ccagtagatc ctagactaga gccctggaag catccaggaa gtcagcctaa   3060
aactgcttgt accaattgct attgtaaaaa gtgttgcttt cattgccaag tttgtttcat   3120
aacaaaagcc ttaggcatct cctatggcag gaagaagcgg agacagcgac gaagagctca   3180
tcagaacagt cagactcatc aagcttctct atcaaagcag taagtagtac atgtaacgca   3240
acctatacca atagtagcaa tagtagcatt agtagtagca ataataatag caatagttgt   3300
gtggtccata gtaatcatag aatataggaa aatattaaga caaagaaaaa tagacaggtt   3360
aattgataga ctaatagaaa gagcagaaga cagtggcaat gagagtgaag gagaaatatc   3420
agcacttgtg gagatggggg tggagatggg gcaccatgct ccttgggatg ttgatgatct   3480
gtagtgctac agaaaaattg tgggtcacag tctattatgg ggtacctgtg tggaaggaag   3540
caaccaccac tctattttgt gcatcagatg ctaaagcata tgatacagag gtacataatg   3600
tttgggccac acatgcctgt gtacccacag accccaaccc acaagaagta gtattggtaa   3660
atgtgacaga aaattttaac atgtggaaaa atgacatggt agaacagatg catgaggata   3720
taatcagttt atgggatcaa agcctaaagc catgtgtaaa attaacccca ctctgtgtta   3780
gtttaaagtg cactgatttg aagaatgata ctaataccaa tagtagtagc gggagaatga   3840
taatggagaa aggagagata aaaaactgct ctttcaatat cagcacaagc ataagaggta   3900
aggtgcagaa agaatatgca ttttttata aacttgatat aataccaata gataatgata   3960
ctaccagcta taagttgaca agttgtaaca cctcagtcat tacacaggcc tgtccaaagg   4020
```

-continued tatcctttga gccaattccc atacattatt gtgccccggc tggttttgcg attctaaaat 4080
gtaataataa gacgttcaat ggaacaggac catgtacaaa tgtcagcaca gtacaatgta 4140
cacatggaat taggccagta gtatcaactc aactgctgtt aaatggcagt ctagcagaag 4200
aagaggtagt aattagatct gtcaatttca cggacaatgc taaaaccata atagtacagc 4260
tgaacacatc tgtagaaatt aattgtacaa gacccaacaa caatacaaga aaaagaatcc 4320
gtatccagag aggaccaggg agagcatttg ttacaatagg aaaaatagga aatatgagac 4380
aagcacattg taacattagt agagcaaaat ggaataacac tttaaaacag atagctagca 4440
aattaagaga acaatttgga aataataaaa caataatctt taagcaatcc tcaggagggg 4500
acccagaaat tgtaacgcac agttttaatt gtggaggggga atttttctac tgtaattcaa 4560
cacaactgtt taatagtact tggtttaata gtacttggag tactgaaggg tcaaataaca 4620
ctgaaggaag tgacacaatc accctcccat gcagaataaa acaaattata aacatgtggc 4680
agaaagtagg aaaagcaatg tatgcccctc ccatcagtgg acaaattaga tgttcatcaa 4740
atattacagg gctgctatta acaagagatg gtggtaatag caacaatgag tccgagatct 4800
tcagacctgg aggaggagat atgagggaca attggagaag tgaattatat aaatataaag 4860
tagtaaaaat tgaaccatta ggagtagcac ccaccaaggc aaagagaaga gtggtgcaga 4920
gagaaaaaag agcagtggga ataggagctt tgttccttgg gttcttggga gcagcaggaa 4980
gcactatggg cgcagcgtca atgacgctga cggtacaggc cagacaatta ttgtctggta 5040
tagtgcagca gcagaacaat ttgctgaggg ctattgaggc gcaacagcat ctgttgcaac 5100
tcacagtctg gggcatcaag cagctccagg caagaatcct ggctgtggaa agatacctaa 5160
aggatcaaca gctcctgggg atttggggtt gctctggaaa actcatttgc accactgctg 5220
tgccttggaa tgctagttgg agtaataaat ctctggaaca gatttggaat cacacgacct 5280
ggatggagtg ggacagagaa attaacaatt acacaagctt aatacactcc ttaattgaag 5340
aatcgcaaaa ccagcaagaa aagaatgaac aagaattatt ggaattagat aaatgggcaa 5400
gtttgtggaa ttggtttaac ataacaaatt ggctgtggta tataaaatta ttcataatga 5460
tagtaggagg cttggtaggt ttaagaatag tttttgctgt actttctata gtgaatagag 5520
ttaggcaggg atattcacca ttatcgtttc agacccacct cccaaccccg aggggacccg 5580
acaggcccga aggaatagaa gaagaaggtg gagagagaga cagagacaga tccattcgat 5640
tagtgaacgg atccttagca cttatctggg acgatctgcg gagcctgtgc ctcttcagct 5700
accaccgctt gagagactta ctcttgattg taacgaggat tgtggaactt ctgggacgca 5760
gggggtggga agccctcaaa tattggtgga atctcctaca atattggagt caggagctaa 5820
agaatagtgc tgttagcttg ctcaatgcca cagccatagc agtagctgag gggacagata 5880
gggttataga agtagtacaa ggagcttgta gagctattcg ccacatacct agaagaataa 5940
gacagggctt ggaaaggatt ttgctataag atgggtggcg cggccgcaat ggtgagcaag 6000
ggcgaggagc tgttcaccgg ggtggtgccc atcctggtcg agctggacgg cgacgtaaac 6060
ggccacaagt tcagcgtgtc cggcgagggc gagggcgatg ccacctacgg caagctgacc 6120
ctgaagttca tctgcaccac cggcaagctg cccgtgccct ggcccaccct cgtgaccacc 6180
ctgacctacg gcgtgcagtg cttcagccgc taccccgacc acatgaagca gcacgacttc 6240
ttcaagtccg ccatgcccga aggctacgtc caggagcgca ccatcttctt caaggacgac 6300
ggcaactaca agacccgcgc cgaggtgaag ttcgagggcg acaccctggt gaaccgcatc 6360
gagctgaagg gcatcgactt caaggaggac ggcaacatcc tggggcacaa gctggagtac 6420

-continued

```
aactacaaca gccacaacgt ctatatcatg gccgacaagc agaagaacgg catcaaggcg   6480
aacttcaaga tccgccacaa catcgaggac ggcagcgtgc agctcgccga ccactaccag   6540
cagaacaccc ccatcggcga cggccccgtg ctgctgcccg acaaccacta cctgagcacc   6600
cagtccgccc tgagcaaaga ccccaacgag aagcgcgatc acatggtcct gctggagttc   6660
gtgaccgccg ccgggatcac tctcggcatg gacgagctgt acaagtaaga attctgactc   6720
gagacctaga aaaacatgga gcaatcacaa gtagcaatac agcagctacc aatgctgatt   6780
gtgcctggct agaagcacaa gaggaggagg aggtgggttt tccagtcaca cctcaggtac   6840
ctttaagacc aatgacttac aaggcagctg tagatcttag ccacttttta aaagaaaagg   6900
ggggactgga agggctaatt cactcccaac gaagacaaga tatccttgat ctgtggatct   6960
accacacaca aggctacttc cctgattggc agaactacac accagggcca gggatcagat   7020
atccactgac ctttggatgg tgctacaagc tagtaccagt tgagcaagag aaggtagaag   7080
aagccaatga aggagagaac acccgcttgt tacaccctgt gagcctgcat gggatggatg   7140
acccggagag agaagtatta gagtggaggt ttgacagccg cctagcattt catcacatgg   7200
cccgagagct gcatccggag tacttcaaga actgctgaca tcgagcttgc tacaagggac   7260
tttccgctgg ggactttcca gggaggcgtg gcctgggcgg gactggggag tggcgagccc   7320
tcagatgctg catataagca gctgcttttt gcttgtactg ggtctctctg gttagaccag   7380
atctgagcct gggagctctc tggctaacta gggaacccac tgcttaagcc tcaataaagc   7440
ttgccttgag tgcttcaagt agtgtgtgcc cgtctgttgt gtgactctgg cgcgcctcta   7500
gaattaattc cgtgtattct atagtgtcac ctaaatcgta tgtgtatgat acataaggtt   7560
atgtattaat tgtagccgcg ttctaacgac aatatgtaca agcctaattg tgtagcatct   7620
ggcttactga agcagaccct atcatctctc tcgtaaactg ccgtcagagt cggtttggtt   7680
ggacgaacct tctgagtttc tggtaacgcc gtcccgcacc cggaaatggt cagcgaacca   7740
atcagcaggg tcatcgctag ccagatcctc tacgccggac gcatcgtggc cggcatcacc   7800
ggcgccacag gtgcggttgc tggcgcctat atcgccgaca tcaccgatgg ggaagatcgg   7860
gctcgccact tcgggctcat gagcgcttgt ttcggcgtgg gtatggtggc aggccccgtg   7920
gccgggggac tgttgggcgc catctccttg catgcaccat tccttgcggc ggcggtgctc   7980
aacggcctca acctactact gggctgcttc ctaatgcagg agtcgcataa gggagagcgt   8040
cgaatggtgc actctcagta caatctgctc tgatgccgca tagttaagcc agccccgaca   8100
cccgccaaca cccgctgacg cgccctgacg ggcttgtctg ctcccggcat ccgcttacag   8160
acaagctgtg accgtctccg ggagctgcat gtgtcagagg ttttcaccgt catcaccgaa   8220
acgcgcgaga cgaaagggcc tcgtgatacg cctattttta taggttaatg tcatgataat   8280
aatggtttct tagacgtcag gtggcacttt tcggggaaat gtgcgcggaa cccctatttg   8340
tttatttttc taaatacatt caaatatgta tccgctcatg agacaataac cctgataaat   8400
gcttcaataa tattgaaaaa ggaagagtat gagtattcaa catttccgtg tcgcccttat   8460
tccctttttt gcggcatttt gccttcctgt ttttgctcac ccagaaacgc tggtgaaagt   8520
aaaagatgct gaagatcagt tgggtgcacg agtgggttac atcgaactgg atctcaacag   8580
cggtaagatc cttgagagtt ttcgccccga agaacgtttt ccaatgatga gcacttttaa   8640
agttctgcta tgtggcgcgg tattatcccg tattgacgcc gggcaagagc aactcggtcg   8700
ccgcatacac tattctcaga atgacttggt tgagtactca ccagtcacag aaaagcatct   8760
tacggatggc atgacagtaa gagaattatg cagtgctgcc ataaccatga gtgataacac   8820
```

-continued

```
tgcggccaac ttacttctga caacgatcgg aggaccgaag gagctaaccg cttttttgca   8880
caacatgggg gatcatgtaa ctcgccttga tcgttgggaa ccggagctga atgaagccat   8940
accaaacgac gagcgtgaca ccacgatgcc tgtagcaatg gcaacaacgt tgcgcaaact   9000
attaactggc gaactactta ctctagcttc ccggcaacaa ttaatagact ggatggaggc   9060
ggataaagtt gcaggaccac ttctgcgctc ggcccttccg gctggctggt ttattgctga   9120
taaatctgga gccggtgagc gtgggtctcg cggtatcatt gcagcactgg ggccagatgg   9180
taagccctcc cgtatcgtag ttatctacac gacggggagt caggcaacta tggatgaacg   9240
aaatagacag atcgctgaga taggtgcctc actgattaag cattggtaac tgtcagacca   9300
agtttactca tatatacttt agattgattt aaaacttcat ttttaattta aaaggatcta   9360
ggtgaagatc ctttttgata atctcatgac caaaatccct taacgtgagt tttcgttcca   9420
ctgagcgtca gaccccgtag aaaagatcaa aggatcttct tgagatcctt tttttctgcg   9480
cgtaatctgc tgcttgcaaa caaaaaaacc accgctacca gcggtggttt gtttgccgga   9540
tcaagagcta ccaactcttt ttccgaaggt aactggcttc agcagagcgc agataccaaa   9600
tactgttctt ctagtgtagc cgtagttagg ccaccacttc aagaactctg tagcaccgcc   9660
tacatacctc gctctgctaa tcctgttacc agtggctgct gccagtggcg ataagtcgtg   9720
tcttaccggg ttggactcaa gacgatagtt accggataag gcgcagcggt cgggctgaac   9780
ggggggttcg tgcacacagc ccagcttgga gcgaacgacc tacaccgaac tgagatacct   9840
acagcgtgag ctatgagaaa gcgccacgct tcccgaaggg agaaaggcgg acaggtatcc   9900
ggtaagcggc agggtcggaa caggagagcg cacgagggag cttccagggg gaaacgcctg   9960
gtatctttat agtcctgtcg ggtttcgcca cctctgactt gagcgtcgat ttttgtgatg  10020
ctcgtcaggg gggcggagcc tatggaaaaa cgccagcaac gcggcctttt tacggttcct  10080
ggccttttgc tggccttttg ctcacatgtt ctttcctgcg ttatcccctg attctgtgga  10140
taaccgtatt accgcctttg agtgagctga taccgctcgc cgcagccgaa cgaccgagcg  10200
cagcgagtca gtgagcgagg aagcggaaga gcgcccaata cgcaaaccgc ctctccccgc  10260
gcgttggccg attcattaat gcagctgtgg aatgtgtgtc agttagggtg tggaaagtcc  10320
ccaggctccc cagcaggcag aagtatgcaa agcatgcatc tcaattagtc agcaaccagg  10380
tgtggaaagt ccccaggctc cccagcaggc agaagtatgc aaagcatgca tctcaattag  10440
tcagcaacca tagtcccgcc cctaactccg cccatcccgc ccctaactcc gcccagttcc  10500
gcccattctc cgccccatgg ctgactaatt ttttttattt atgcagaggc cgaggccgcc  10560
tcggcctctg agctattcca gaagtagtga ggaggctttt ttggaggcct aggcttttgc  10620
aaaaagcttg gacacaagac aggcttgcga gatatgtttg agaataccac tttatcccgc  10680
gtcagggaga ggcagtgcgt aaaaagacgc ggactcatgt gaaatactgg tttttagtgc  10740
gccagatctc tataatctcg cgcaacctat tttcccctcg aacacttttt aagccgtaga  10800
taaacaggct gggacacttc acatgagcga aaaatacatc gtcacctggg acatgttgca  10860
gatccatgca cgtaaactcg caagccgact gatgccttct gaacaatgga aaggcattat  10920
tgccgtaagc cgtggcggtc tggtaccggg tgcgttactg gcgcgtgaac tgggtattcg  10980
tcatgtcgat accgtttgta tttccagcta cgatcacgac aaccagcgcg agcttaaagt  11040
gctgaaacgc gcagaaggcg atggcgaagg cttcatcgtt attgatgacc tggtggatac  11100
cggtggtact gcggttgcga ttcgtgaaat gtatccaaaa gcgcactttg tcaccatctt  11160
cgcaaaaccg gctggtcgtc cgctggttga tgactatgtt gttgatatcc cgcaagatac  11220
```

ctggattgaa cagccgtggg atatgggcgt cgtattcgtc ccgccaatct ccggtcgcta 11280
atcttttcaa cgcctggcac tgccgggcgt tgttcttttt aacttcaggc gggttacaat 11340
agtttccagt aagtattctg gaggctgcat ccatgacaca ggcaaacctg agcgaaaccc 11400
tgttcaaacc ccgctttaaa catcctgaaa cctcgacgct agtccgccgc tttaatcacg 11460
gcgcacaacc gcctgtgcag tcggcccttg atggtaaaac catccctcac tggtatcgca 11520
tgattaaccg tctgatgtgg atctggcgcg gcattgaccc acgcgaaatc ctcgacgtcc 11580
aggcacgtat tgtgatgagc gatgccgaac gtaccgacga tgatttatac gatacggtga 11640
ttggctaccg tggcggcaac tggatttatg agtgggcccc ggatctttgt gaaggaacct 11700
tacttctgtg gtgtgacata attggacaaa ctacctacag agatttaaag ctctaaggta 11760
aatataaaat ttttaagtgt ataatgtgtt aaactactga ttctaattgt ttgtgtattt 11820
tagattccaa cctatggaac tgatgaatgg gagcagtggt ggaatgcctt taatgaggaa 11880
aacctgtttt gctcagaaga aatgccatct agtgatgatg aggctactgc tgactctcaa 11940
cattctactc ctccaaaaaa gaagagaaag gtagaagacc ccaaggactt tccttcagaa 12000
ttgctaagtt ttttgagtca tgctgtgttt agtaatagaa ctcttgcttg ctttgctatt 12060
tacaccacaa aggaaaaagc tgcactgcta tacaagaaaa ttatggaaaa atattctgta 12120
acctttataa gtaggcataa cagttataat cataacatac tgtttttttct tactccacac 12180 aggcatagag tgtctgctat taataactat gctcaaaaat tgtgtacctt tagcttttta 12240
atttgtaaag ggggttaataa ggaatatttg atgtatagtg ccttgactag agatcataat 12300
cagccatacc acatttgtag aggttttact tgctttaaaa aacctcccac acctcccccct 12360 gaacctgaaa cataaaat 12378

<210> SEQ ID NO 53
<211> LENGTH: 24
<212> TYPE: DNA
<213> ORGANISM: Artificial
<220> FEATURE:
<223> OTHER INFORMATION: Linear HIV-1 nucleic acid/primers

<400> SEQUENCE: 53
gcccctagga aaaagggctg ttgg 24

<210> SEQ ID NO 54
<211> LENGTH: 25
<212> TYPE: DNA
<213> ORGANISM: Artificial
<220> FEATURE:
<223> OTHER INFORMATION: Linear HIV-1 nucleic acid/primers

<400> SEQUENCE: 54
ctaggaaaaa gggctgttgg aaatg 25

<210> SEQ ID NO 55
<211> LENGTH: 20
<212> TYPE: DNA
<213> ORGANISM: Artificial
<220> FEATURE:
<223> OTHER INFORMATION: Linear HIV-1 nucleic acid/primers

<400> SEQUENCE: 55
gtactggatg tgggtgatgc 20

<210> SEQ ID NO 56
<211> LENGTH: 19
<212> TYPE: DNA

-continued

```
<213> ORGANISM: Artificial
<220> FEATURE:
<223> OTHER INFORMATION: Linear HIV-1 nucleic acid/primers

<400> SEQUENCE: 56

gtgggaaaat tgaattggg                                                19


<210> SEQ ID NO 57
<211> LENGTH: 20
<212> TYPE: DNA
<213> ORGANISM: Artificial
<220> FEATURE:
<223> OTHER INFORMATION: Linear HIV-1 nucleic acid/primers

<400> SEQUENCE: 57

gccacctgga ttcctgagtg                                               20


<210> SEQ ID NO 58
<211> LENGTH: 24
<212> TYPE: DNA
<213> ORGANISM: Artificial
<220> FEATURE:
<223> OTHER INFORMATION: Linear HIV-1 nucleic acid/primers

<400> SEQUENCE: 58

ctccttttag ctgacattta tcac                                          24
```